US007153947B2

(12) United States Patent
Ribeiro et al.

(10) Patent No.: US 7,153,947 B2

(45) Date of Patent: Dec. 26, 2006

(54) IXODES SALIVARY ANTICOMPLEMENT PROTEIN

(75) Inventors: José M. C. Ribeiro, Rockville, MD (US); Jesus G. Valenzuela, Gaithersburg, MD (US); Rosane Charlab, Rockville, MD (US); Thomas N. Mather, Wakefield, RI (US)

(73) Assignees: The United States of America as represented by the Department of Health and Human Services, Washington, DC (US); University of Rhode Island, Kingston, RI (US)

( * ) Notice: Subject to any disclaimer, the term of this patent is extended or adjusted under 35 U.S.C. 154(b) by 398 days.

(21) Appl. No.: 10/403,182

(22) Filed: Mar. 28, 2003

(65) Prior Publication Data

US 2004/0019194 A1 Jan. 29, 2004

Related U.S. Application Data

(63) Continuation of application No. PCT/US00/26746, filed on Sep. 28, 2000.

(51) Int. Cl.
*C07H 21/04* (2006.01)
*C12P 21/04* (2006.01)

(52) U.S. Cl. .................................... 536/23.1; 435/71.1

(58) Field of Classification Search ................ 536/23.1
See application file for complete search history.

(56) References Cited

OTHER PUBLICATIONS

Anderson et al. Novel *Borrelia burgdorferi* Isolates from *Ixodes scapularis* and *Ixodes dentatus* Ticks Feeding on Humans. Journal of Clinical Microbiology. Mar. 1996. vol. 34, No. 3, pp. 524-529.*

Urioste et al. Saliva of the Lyme Disease Vector, *Ixodes dammini*, Blocks Cell Activation by a Nonprostaglandin E2-dependent Mechanism. Journal of Experimental Medicine. Sep. 1994. vol. 180, No. 3, pp. 1077-1085.*

Altschul, S.F. et al. 1990 *Basic local alignment search tool. J. Mol. Biol.* 215:403-410.

Damerau, B. 1987 *Biological activities of complement-derived peptides Rev. Physiol. Biochem. Pharmacol.* 108:152-206.

Davidar, P. et al. 1989 *Differential distribution of immature Ixodes dammini (Acari: Ixodidae) on rodent hosts J. Parasitol.* 75:898-904.

Hugli, T.E. & Muller-Eberhard, H.J. 1978 *Anaphylatoxins: C3a and C5a Adv. Immunol.* 26:1-53.

Joiner, K.A. 1988 *Complement evasion by bacteria and parasites Annu. Rev. Microbiol.* 42:201-230.

Jokiranta, T.S. et al. 1995 *Complement resistance of parasites Scand. J. Immunol.* 42:9-20.

Kirschfink, M. 1997 *Controlling the complement system in inflammation Immunopharmacology* 38:51-62.

Lawrie, C.H. et al. 1999 *Ixodes ticks: serum species sensitivity of anticomplement activity Exp. Parasitol.* 93:207-214.

Mather T.N. et al. 1996 *Ixodes saliva: vector competence for Borrelia burgdorferi and potential vaccine strategies. 7th International Congress on Lyme Borreliosis* (abstr. # A029), San Francisco, CA.

Mather T.N. et al. 1999 *Tick and host associated determinants of tick-borne pathogen infection risk. 8th International Congress on Lyme Borreliosis and other Emerging Tick-borne Diseases* (Abstr. # O20), Munich, Germany.

Nielsen, H. et al. 1997 *Identification of prokaryotic and eukaryotic signal peptides and prediction of their cleavage sites Protein Eng.* 10:1-6.

Platts-Mills, T. A. E. & Ishizaka, K. 1974 *Activation of the alternate pathway of human complements by rabbit cells J. Immunol.* 113:348-358.

Ribeiro, J.M.C. 1987 *Ixodes dammini: salivary anti-complement activity Exp. Parasitol.* 64:347-353.

Ribeiro, J.M.C. 1989 *Role of saliva in tick/host interactions Exp. Appl. Acarol.* 7:15-20.

Ribeiro, J.M.C. & Spielman, A. 1986 *Ixodes dammini: salivary anaphylatoxin inactivating activity Exp. Parasitol.* 62:292-297.

Rosengard, A.M. & Ahearn, J. M. 1999 *Viral complement regulatory proteins Immunopharmacology* 42:99-106.

Tatchell, R.J. 1967 *A modified method for obtaining tick oral secretion J. Parasitol.* 53:1106-1107.

Trager, W. 1939 *Acquired immunity to ticks J. Parasitol.* 25:57-81.

Valenzuela J.G. et al. 2000 *Purification, cloning, and expression of a novel salivary anticomplement protein from the tick, Ixodes scapularis. J Biol Chem.* 275(25):18717-23.

Valenzuela, J.G. et al. 1998 *Purification, Cloning, and Expression of an Apyrase from the Bed Bug Cimex lectularius A New Type of Nucleotide-Binding Enzyme J. Biol. Chem.* 273-30583-30590.

Vogt, W. 1974 *Activation, activities and pharmacologically active products of complement Pharmacol. Rev.* 26:125-169.

Wikel, S.K. 1979 *Acquired resistance to ticks: expression of resistance by C4-deficient guinea pigs Am. J. Trop. Med. Hyg.* 28:586-590.

Wikel, S.K. 1996 *Host immunity to ticks Annu. Rev. Entomol.* 41:1-22.

Wikel, S.K. & Allen, J.R. 1977 *Acquired resistance to ticks. iii. Cobra venom factor and the resistance response. Immunology* 32:457-465.

Willadsen, P & Riding, G.A. 1980 *On the biological role of a proteolytic-enzyme inhibitor from the ectoparasitic tick Boophilus microplus Biochem. J.* 189:295-303.

Wurzner, R. 1999 *Evasion of pathogens by avoiding recognition or eradication by complement, in part via molecular mimicry Mol. Immunol.* 36:249-260.

Zipfel, P.F. et al. 1999 *Factor H and disease: a complement regulator affects vital body functions Mol. Immunol.* 36:241-248.

Zipfel, P.F. et al. 1999 *The factor H protein family Immunopharmacology* 42:53-60.

* cited by examiner

*Primary Examiner*—Robert A. Wax
*Assistant Examiner*—Suzanne M. Noakes
(74) *Attorney, Agent, or Firm*—Knobbe, Martens, Olson & Bear, LLP

(57) ABSTRACT

Isac, a novel protein with anticomplement activity is disclosed. Isac can be isolated from the salivary glands of ticks or made by recombinant methods using various DNA expression techniques.

7 Claims, 20 Drawing Sheets

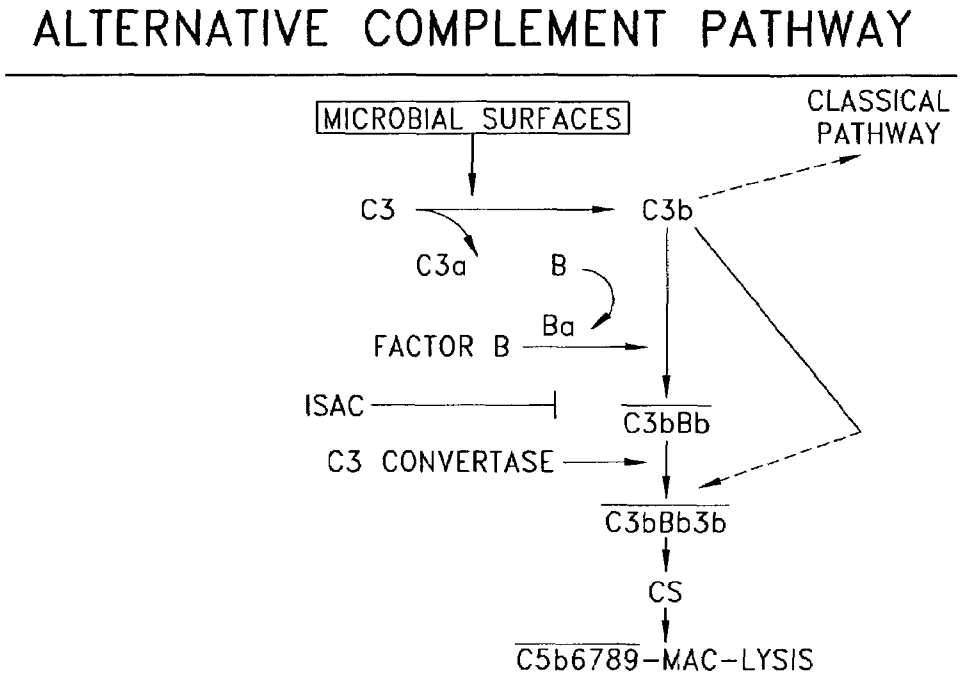
FIG. A

```
  1 - ACGGTTGCTCACAGCACTGAGGTTTCAGAGCAAGGGTCTACCAGCCATGAGGACTGCGTT
    -                                               M  R  T  A  F
 61 - TACCTGTGCTCTTTTGGCGATTTCGTTTCTAGGAAGCCCGTGTTCGTCCAGCGAAGACGG
    -  T  C  A  L  L  A  I  S  F  L  G  S  P  C  S  S  S  E  D  G
121 - TCTCGAGCAAGATACCATAGTGGAAACTACTACACAAAATCTCTACGAACGTCATTATAG
    -  L  E  Q  D  T  I  V  E  T  T  T  Q  N  L  Y  E  R  H  Y  R
181 - AAATCATTCTGGATTGTGCGGGGCACAGTATAGGAATTCAAGCCATGCGGAAGCCGTTTA
    -  N  H  S  G  L  C  G  A  Q  Y  R  N  S  S  H  A  E  A  V  Y
241 - CAACTGCACGCTCAATCATTTGCCCCCAGTCGTGAATGCAACCTGGGAAGGAATTAGGCA
    -  N  C  T  L  N  H  L  P  P  V  V  N  A  T  W  E  G  I  R  H
301 - TCGAATTAATAAAACCATACCTCAGTTTGTAAAATTGATTTGCAACTTTACTGTTGCGAT
    -  R  I  N  K  T  I  P  Q  F  V  K  L  I  C  N  F  T  V  A  M
361 - GCCTCAAGAATTCTACTTAGTTTATATGGGGTCAGATGGAAACTCAGACTTTGAAGAGGA
    -  P  Q  E  F  Y  L  V  Y  M  G  S  D  G  N  S  D  F  E  E  D
421 - CAAAGAGAGCACAGGCACTGATGAAGACAGTAACACGGGATCTTCTGCTGCAGCTAAAGT
    -  K  E  S  T  G  T  D  E  D  S  N  T  G  S  S  A  A  A  K  V
481 - TACAGAAGCGCTAATAATAGAAGCAGAGGAAAACTGCACGGCGCATATAACTGGTTGGAC
    -  T  E  A  L  I  I  E  A  E  E  N  C  T  A  H  I  T  G  W  T
541 - CACTGAAACCCCGACCACGCTGGAACCTACGACAGAGTCTCAATTTGAGGCAATTCCCTG
    -  T  E  T  P  T  T  L  E  P  T  T  E  S  Q  F  E  A  I  P  *
601 - AGGCATCGTGTGCCGATCTATCACCCGGTTATTTCACCGCGTGGTTTTGATGCCCGTGCA

661 - AGCACAGTTCTGATACGGGTGGCGAGGTGCTTTGCCGAGATTGATTTAAATAAAATTCGA

721 - TAAAGAAAAAAAAAAAAAAAAAAAAAAAAAAA
```

IXODES SALIVARY ANTICOMPLEMENT PROTEIN

RELATED APPLICATIONS

This application is a continuation and claims the benefit of priority of International Application No. PCT/US00/26746 filed Sep. 28, 2000, designating the United States of America and published in English, which is hereby expressly incorporated by reference in its entirety.

BACKGROUND OF THE INVENTION

1. Field of the Invention

The present invention relates to the field of molecular biology. The present invention discloses the discovery of the novel protein Isac. Isac has anticomplement activity and can be isolated and purified from the salivary glands of ticks or made by recombinant methods using various DNA expression techniques.

2. Description of the Related Art

The alternative pathway of complement is an evolutionarily old first line of defense against pathogens (Joiner, K. A. (1988) Ann. Rev. Microbiol. 42, 201–230). Complement activation leads to production of inflammatory anaphylatoxins (Hugli, T. E., and Muller-Eberhard, H. J. (1978) Adv. Immunol. 26, 1–53, Damerau, B. (1987) Rev. Physiol. Biochem. Pharmacol. 108, 152–206), and to the formation of a membrane attack complex leading to the lysis of the invading organism (Joiner, K. A. (1988) Ann. Rev. Microbiol. 42, 201–230). Endogenous regulators exist to prevent pathology associated with unconfined or inadvertent complement activation (Zipfel, P. F., Hellwage, J., Friese, M. A., Hegasy, G., Jokiranta, S. T., and Meri, S. (1999) Mol. Immunol. 36(4–5), 241–248, Kirschfink, M. (1997) Immunopharmacology 38(1–2), 51–62). Successful pathogens have developed several mechanisms to evade the host complement system (Joiner, K. A. (1988) Ann. Rev. Microbiol. 42, 201–230, Jokiranta, T. S., Jokipii, L., and Meri, S. (1995) Scand. J. Immunol. 42, 9–20, Wurzner, R. (1999) Mol. Immunol. 36(4–5), 249–260). In several of these evasion mechanisms, pathogens may recruit host complement regulatory molecules to their own surface or produce inhibitors of complement activation, which are either secreted or remain associated with their surfaces (Joiner, K. A. (1988) Ann. Rev. Microbiol. 42, 201–230, Jokiranta, T. S., Jokipii, L., and Meri, S. (1995) Scand. J. Immunol. 42, 9–20, Wurzner, R. (1999) Mol. Immunol. 36(4–5), 249–260, Rosengard, A. M., and Ahearn, J. M. (1999) Immunopharmacology 42(1–3), 99–106)

Ticks are ectoparasites that may feed for several days or even weeks with their mouthparts embedded into their vertebrate hosts. Although unnatural hosts can mount an effective immune response against ticks (Trager, W. (1939) J. Parasitol. 25, 57–81, Wikel, S. K. (1996) Ann. Rev. Entomol. 41, 1–22), only minor rejection reactions are observed when ticks feed on their natural hosts (Trager, W. (1939) J. Parasitol. 25, 57–81, Ribeiro, J. M. C. (1989) Exp. Appl. Acarol. 7, 15–20). The alternative pathway of complement was implicated in rejection reactions of guinea pigs against the tick *Dermacentor andersoni* (Wikel, S. K., and Allen, J. R. (1977) Immunology 32, 457–465, Wikel, S. K. (1979) Am. J. trop. Med. Hyg. 28, 586–590). The tick vector of Lyme disease in Eastern North America, *Ixodes scapularis*, can successfully feed repeatedly on its natural host, the white-footed mouse, *Peromyscus leucopus* (Trager, W. (1939) J. Parasitol. 25, 57–81, Davidar, P., Wilson, M., and Ribeiro, J. M. (1989) J. Parasitol. 75(6), 898–904), perhaps because it has salivary compounds that deactivate anaphylatoxins (Ribeiro, J. M. C., and Spielman, A. (1986) Exp. Parasitol. 62, 292–297) and inhibit the alternative pathway of complement (Ribeiro, J. M. C. (1987) Exp. Parasitol. 64, 347–353). Indeed, the host range of Ixodes correlates with their ability to counteract the alternative complement pathway of their most common hosts (Lawrie, C. H., Randolph, S. E., and Nuttall, P. A. (1999) Exp. Parasitol. 93(4), 207–214).

SEGUE TO THE DESCRIPTION

*I. scapularis* saliva has an inhibitor of the alternative pathway of complement activation (Ribeiro, J. M. C. (1987) Exp. Parasitol. 64, 347–353), as shown by inhibition of the lysis of rabbit erythrocytes by human sera in the presence of EGTA and $Mg^{++}$ ions. This saliva also prevents deposition of C3 to agarose-coated plates and inhibits release of C3a by the C3 convertase formed by the alternative pathway of complement activation (Ribeiro, J. M. C. (1987) Exp. Parasitol. 64, 347–353). Because the molecular nature of this inhibitor remained unknown, we purified, obtained amino terminal sequence, cloned, and expressed Isac, which is a novel molecule behaving as a regulator of complement activation (RCA). Isac is one of the smallest proteins known to have RCA activity and may serve as a tool to understand C3 convertase regulation.

SUMMARY OF THE INVENTION

The alternative pathway of complement is an important defense against pathogens and in tick rejection reactions. The tick *Ixodes scapularis* is able to feed repeatedly on its natural host and has a salivary anticomplement activity that presumably facilitates feeding. In this disclosure, we purified and then obtained the amino terminal sequence of the *I. scapularis* salivary anticomplement (Isac). We found a full-length clone coding for Isac by random screening of a salivary gland cDNA library. Expressing Isac cDNA in COS cells reproduced the activity found in tick saliva, namely, inhibition of rabbit erythrocyte lysis by human serum in the presence of $Mg^{++}$ and EGTA, inhibition of C3b binding to agarose in the presence of $Mg^{++}$ and EGTA, and acceleration of factor Bb uncoupling from the C3 convertase generated by the alternative pathway. Recombinant Isac had no effect on the recalcification time of human platelet-poor plasma or in the classical complement pathway, indicating that it is a specific inhibitor similar to the regulators of complement activation of the alternative pathway such as factor H. Isac, however, has no similarity to any protein in the GenBank database, indicating that it is a novel and relatively small (18.5 kDa) anticomplement molecule.

SUMMARY OF SEQUENCES

Appendix A depicts Isac and its carboxy truncations. Appendix B depicts Isac and its amino truncations.

BRIEF DESCRIPTION OF THE DRAWINGS

FIG A. Alternative Complement Pathway. Isac disrupts the alternative complement pathway by inhibiting factor Bb and/or C3b (C3 convertase). By inhibiting factor Bb and/or C3b (C3 convertase), Isac prevents cell lysis and anaphylatoxin production.

FIG. 3. Nucleotide (SEQ ID NO: 401) and predicted translated protein sequences (SEQ ID NO: 402) from Isac cDNA (A). The amino acids in [bold] were obtained by Edman degradation (SEQ ID NO: 402, amino acids #22–41) (B). (S/G) indicates equal signal of serine and glycine, whereas X indicates that no amino acid could be identified. This is GenBank accession number AF270496.

DETAILED DESCRIPTION OF THE PREFERRED EMBODIMENT

Figure 1A:
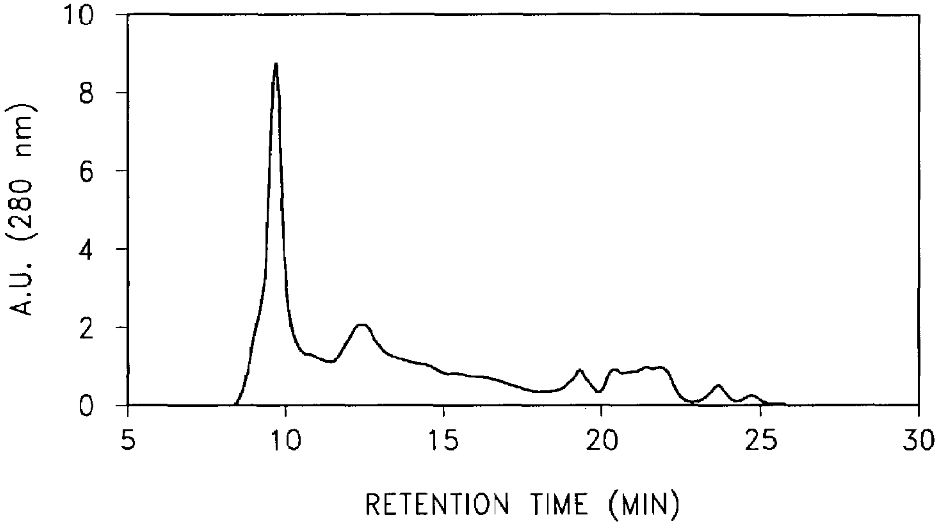
FIG. 1. Molecular sieving chromatography of homogenized *I. scapularis* tick salivary glands. (A) Cumulative UV (280 nm) absorbance tracings of 10 chromatograms representing 500 homogenized pairs of glands. Inset: Log of $M_r$ standards plotted against their retention times. The arrow indicates retention time of the salivary anticomplement activity. (B) Anticomplement activity was measured in 12.5 μl aliquots of each fraction by their ability to inhibit lysis of rabbit erythrocytes by human serum in the presence of $MgCl_2$.

The blood complement system in mammals is a first line of defense against invasion by pathogens, from viruses and bacteria to tick attachment and feeding. Its activation leads to bacterial lysis and defensive inflammatory reactions at the site of its activation. The alternative pathway is mostly independent of antibody and thus serves as a defense mechanism for non-immune people. Not surprisingly, most successful pathogens have developed mechanisms to inactivate this pathway. The tick vector of Lyme disease has an inhibitor of the C3 convertase of the alternate pathway, a key enzyme for complement activation. In this disclosure we purified, cloned and expressed this tick's anticomplement protein, named Isac. Isac is a novel anticomplement protein as it has no homologies to other known anticomplement molecules. Because inactivation of Isac by antibodies will make transmission of *Borrelia burgdorferi* (the bacteria responsible for Lyme disease) to humans more difficult, Isac is envisioned as a vaccine to protect humans (and their pets) against Lyme disease. Additionally, Isac can be used as an anticomplement molecule in acute syndromes where activation of the alternative pathway of complement is implicated. For example, in some surgeries where blood comes in contact with foreign surfaces, such as cardio-pulmonary surgery (Gu, Y. John, Mariani, Massimo A., Boonstra, Piet W., Grandjean, Jan G., and van Oeveren, Willem (1999) Chest 116(4): 892–8, Tarnok, A., Hambsch, J., Emmrich, F., Sack, U., van Son, J., Bellinghausen, W., Borte, M., and Scheider, P. (1999) Pediatr. Cardiol. 20(2): 113–25), administration of Isac is envisioned as ameliorating attendant complications. The same situation occurs in patients being submitted to hemodialysis, where the dialysis membrane may trigger activation of the complement pathway (Kormoczi, G. F., Rosenkranz, A. R., and Zlabinger, G. J. (1999) Clin. Chem. Lab. Med. 37(3):351–5). Administration of Isac is envisioned as preventing the amplification of the complement deposition, and as reverting the activation of the C3 convertase, thus stopping the production of anaphylatoxins. Other uses are envisioned as being in rheumatoid conditions such as lupus erythematosus or juvenile arthritis, where alternative complement activation is implicated (Aggarwal, A., Bhardwaj, A., Alam, S., and Misra R. (2000) Rheumatology 39(2):189–92).

Definitions

The term "isolated" requires that a material be removed from its original environment (e.g., the natural environment if it is naturally occurring). For example, a naturally occurring polynucleotide or polypeptide present in a living cell is not isolated, but the same polynucleotide or polypeptide, separated from some or all of the coexisting materials in the natural system, is isolated.

The term "purified" does not require absolute purity; rather it is intended as a relative definition, with reference to the purity of the material in its natural state. Purification of natural material to at least one order of magnitude, preferably two or three magnitudes, and more preferably four or five orders of magnitude is expressly contemplated.

The term "enriched" means that the concentration of the material is at least about 2, 5, 10, 100, or 1000 times its natural concentration (for example), advantageously 0.01% by weight. Enriched preparations of about 0.5%, 1%, 5%, 10%, and 20% by weight are also contemplated.

The Isac Gene

The cDNA sequence (SEQ. ID. NO. 401) and deduced amino acid sequence (SEQ. ID. NO. 402) of Isac are shown in FIG. 3A. The signal sequence extends from amino acid residue 1 to 21. The mature protein contains 163 amino acids.

The Isac nucleotide sequences of the invention include: (a) the cDNA sequence shown in FIG. 3A; (b) nucleotide sequence that encodes the amino acid sequence shown in FIG. 3A, its functional domains, truncations thereof, as well as substitutions, insertions, and deletions (including fusion proteins) thereof; (c) any nucleotide sequence that hybridizes to the complement of the cDNA sequence shown in FIG. 3A under highly stringent conditions, e.g., hybridization to filter-bound DNA in 0.5 M NaHPO4, 7% sodium dodecyl sulfate (SDS), 1 mM EDTA at 65 C., and washing in 0.1 times SSC/0.1% SDS at 68 C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product; and (d) any nucleotide sequence that hybridizes to the complement of the cDNA sequence shown in FIG. 3A under less stringent conditions, such as moderately stringent conditions, e.g., washing in 0.2 times SSC/0.1% SDS at 42 C. (Ausubel et al., 1989, supra), yet which still encodes a functionally equivalent gene product. Functional equivalents of Isac include those naturally occurring and engineered, as judged by any of a number of criteria, including, but not limited to, the binding affinity for factor Bb and/or C3b, the resulting biological effect of factor Bb and/or C3b binding, anticomplement activity, generation of antibodies that specifically bind Isac, and identification of compounds that can be used to modulate the alternative complement pathway.

The invention also includes nucleic acid molecules, preferably DNA molecules, that hybridize to, and are therefore the complements of, the nucleotide sequences (a) through (d), in the preceding paragraph.

In addition to the Isac nucleotide sequences described above, full or partial length Isac cDNA present in the same species and/or homologs of the Isac gene present in other species can be identified and readily isolated, without undue experimentation, by molecular biological techniques well known in the art. For example, expression libraries of cDNAs synthesized from salivary gland mRNA derived from the organism of interest can be screened using labeled factor Bb and/or C3b derived from that species, e.g., a factor Bb and/or C3b fusion protein. Alternatively, such cDNA libraries, or genomic DNA libraries derived from the organism of interest can be screened by hybridization using the nucleotides described herein as hybridization or amplification probes. Furthermore, genes at other genetic loci within the genome that encode proteins which have extensive homology to one or more domains of the Isac gene product can also be identified via similar techniques. In the case of cDNA libraries, such screening techniques can identify clones derived from alternatively spliced transcripts in the same or different species.

Screening can be by filter hybridization, using duplicate filters. The labeled probe can contain at least 15–30 base pairs of the Isac nucleotide sequence, as shown in FIG. 3A. The hybridization washing conditions used should be of a lower stringency when the cDNA library is derived from an organism different from the type of organism from which the labeled sequence was derived. With respect to the cloning of a human Isac homolog, using tick Isac probes, for example, hybridization can, for example, be performed at 65 C overnight in Church's buffer (7% SDS, 250 mM NaHPO4, 2 uM EDTA, 1% BSA). Washes can be done with 2 times SSC, 0.1% SDS at 65 C. and then at 0.1 times SSC, 0.1% SDS at 65 C.

Low stringency conditions are well known to those of skill in the art, and will vary predictably depending on the specific organisms from which the library and the labeled sequences are derived. For guidance regarding these and other hybridization conditions see, for example, Sambrook et al., 1989, Molecular Cloning, A Laboratory Manual, Cold Springs Harbor Press, N.Y.; and Ausubel et al, 1989, Current Protocols in Molecular Biology, Green Publishing Associates and Wiley Interscience, N.Y.

Alternatively, the labeled Isac nucleotide probe may be used to screen a genomic library derived from the organism of interest, again, using appropriately stringent conditions.

Further, a full or partial length Isac cDNA present in the same species and/or homologs of the Isac gene present in other species may be isolated from nucleic acid of the organism of interest by performing PCR using two degenerate oligonucleotide primer pools designed on the basis of amino acid sequences within the Isac gene product disclosed herein. The template for the reaction may be cDNA obtained by reverse transcription of mRNA prepared from, for example, cell lines or tissue, such as salivary gland, known or suspected to express an Isac gene allele.

The PCR product may be subcloned and sequenced to ensure that the amplified sequences represent the sequences of an Isac gene. The PCR fragment may then be used to isolate a full length cDNA clone by a variety of methods. For example, the amplified fragment may be labeled and used to screen a cDNA library, such as a bacteriophage cDNA library. Alternatively, the labeled fragment may be used to isolate genomic clones via the screening of a genomic library.

PCR technology may also be utilized to isolate full length cDNA sequences. For example, RNA may be isolated, following standard procedures, from an appropriate cellular or tissue source (i.e., one known, or suspected, to express the Isac gene, such as, for example, salivary gland). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, supra.

In addition to nucleotide sequences encoding the full-length Isac protein 163-mer, other embodiments of the invention may include nucleotide sequences encoding truncations of the Isac protein which exhibit binding affinity for factor Bb and/or C3b, the resulting biological effect of factor Bb and/or C3b binding, anticomplement activity, generation of antibodies that specifically bind Isac, or identification of compounds that can be used to modulate the alternative complement pathway. Truncations of Isac peptides may comprise peptides of between 3 and 163 amino acid residues (i.e., peptides ranging in size from a tripeptide to a 163-mer polypeptide), as shown in Appendix A (Table I) and Appendix B (Table II), infra. Peptide sequences in these tables are listed from amino (left) to carboxy (right) terminus. "X" may represent an amino group (—$NH_2$) and "Z" may represent a carboxyl (—COOH) group. Alternatively, "X" may represent a hydrophobic group, including but not limited to carbobenzyl, dansyl, or T-butoxycarbonyl; an acetyl group; a 9-fluorenylmethoxy-carbonyl (FMOC) group; or a covalently attached macromolecular group, including but not limited to a lipid-fatty acid conjugate, polyethylene glycol, carbohydrate or peptide group. Further, "Z" may represent an amino group; a T-butoxycarbonyl group; or a covalently attached macromolecular group, including but not limited to a lipid-fatty acid conjugate, polyethylene glycol, carbohydrate or peptide group. A preferred "X" or "Z" macromolecular group is a peptide group.

The invention encompasses nucleotide sequences that encode not only Isac but also its functional domains, besides truncations thereof, as well as substitutions, insertions, and deletions (including fusion proteins) thereof.

Amino acid substitutions may be of a conserved or non-conserved nature. Conserved amino acid substitutions consist of replacing one or more amino acids of the Isac or Isac-related sequence with amino acids of similar charge, size, and/or hydrophobicity characteristics, such as, for example, a glutamic acid (E) to aspartic acid (D) amino acid substitution. Non-conserved substitutions consist of replacing one or more amino acids of the Isac or Isac-related sequence with amino acids possessing dissimilar charge, size, and/or hydrophobicity characteristics, such as, for example, a glutamic acid (E) to valine (V) substitution. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. One or more such substitutions may be introduced into the Isac or Isac-related sequence, as long as such substitutions result in variants which exhibit binding affinity for factor Bb and/or C3b, the resulting biological effect of factor Bb and/or C3b binding, anticomplement activity, generation of antibodies that specifically bind Isac, or identification of compounds that can be used to modulate the alternative complement pathway.

Amino acid insertions may consist of single amino acid residues or stretches of residues. The insertions may be made at the carboxy or amino terminal end of the Isac or Isac-related sequence, as well as at a position internal to the sequence. Such insertions made at either the carboxy or amino terminus of the sequence of interest may be of a broader size range. One or more such insertions may be introduced into the Isac or Isac-related sequence, as long as such insertions result in variants which exhibit binding affinity for factor Bb and/or C3b, the resulting biological effect of factor Bb and/or C3b binding, anticomplement activity, generation of antibodies that specifically bind Isac, or identification of compounds that can be used to modulate the alternative complement pathway.

Deletions of Isac or Isac-related sequences are also within the scope of the invention. Such deletions consist of the removal of one or more amino acids from the Isac or Isac-related sequence. Such deletions may involve a single contiguous or greater than one discrete portion of the original sequences. One or more such deletions may be introduced into the Isac or Isac-related sequence, as long as such deletions result in variants which exhibit binding affinity for factor Bb and/or C3b, the resulting biological effect of factor Bb and/or C3b binding, anticomplement activity, generation of antibodies that specifically bind Isac, or identification of compounds that can be used to modulate the alternative complement pathway.

The invention also encompasses (a) DNA vectors that contain any of the foregoing Isac or Isac-related coding sequences and/or their complements; (b) DNA expression vectors that contain any of the foregoing Isac or Isac-related coding sequences operatively associated with a regulatory element that directs the expression of the coding sequences; and (c) genetically engineered host cells that contain any of the foregoing Isac or Isac-related coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast alpha-mating factors.

Isac Proteins, Polypeptides and Peptides

The Isac protein, its functional domains, truncations thereof, as well as substitutions, insertions, and deletions (including fusion proteins) thereof can be prepared for a number of uses, including, but not limited to, binding factor Bb and/or C3b, the resulting biological effect of factor Bb and/or C3b binding, anticomplement activity, generation of antibodies that specifically bind Isac, and identification of compounds that can be used to modulate the alternative complement pathway.

The amino acid sequences of the invention include the amino acid sequence shown in FIG. 3A (SEQ. ID. NO: 402). Further, Isac and Isac-related amino acid sequences are encompassed by the invention, including mature Isac protein, its functional domains, truncations thereof, as well as substitutions, insertions, and deletions thereof. In fact, any Isac or Isac-related protein, polypeptide or peptide encoded by the Isac or Isac-related nucleotide sequences described in the section above are within the scope of the invention.

The preferred isolated Isac and Isac-related amino acid sequences of the present invention may be isolated and purified from natural sources. Preferred as natural sources are ticks; suitable ticks include *Ixodes scapularis, Ixodes ricinus*, and *Ornithodorus moubatta*. Especially preferred as a natural source is *Ixodes scapularis*.

The preferred amino acid sequences of the present invention are isolated from their natural source by methods known in the biochemical arts. These methods include preparing a soluble extract and enriching the extract using chromatographic methods on different solid support matrices. An example of a preferred method of purification of an isolated protein of the present invention would include that as disclosed in the Example.

The preferred isolated Isac and Isac-related amino acid sequences of the present invention may be synthesized by standard methods known in the chemical arts.

The isolated amino acid sequences of the present invention may be prepared using solid-phase synthesis, such as that described by Merrifield, J. Amer. Chem. Soc., 85:2149 (1964) or other equivalent methods known in the chemical arts, such as the method described by Houghten in Proc. Natl. Acad. Sci., 82:5132 (1985).

Alternatively, the preferred isolated Isac and Isac-related amino acid sequences of the present invention may be made by recombinant DNA methods taught herein and well known in the biological arts. Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y. Such methods can be used to construct expression vectors containing the cDNA and other nucleotide sequences described in the section above and appropriate transcriptional and translational control signals. These methods include, for example, in vitro recombinant DNA techniques, synthetic techniques, and in vivo genetic recombination.

A variety of host-expression vector systems may be utilized to express the cDNA and other nucleotide sequences of the invention. The expression systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing Isac and Isac-related nucleotide sequences; yeast (e.g., *Saccharomyces, Pichia*) transformed with recombinant yeast expression vectors containing Isac and Isac-related nucleotide sequences; insect cell systems infected with recombinant virus expression vectors (e.g., baculovirus) containing Isac and Isac-related nucleotide sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing Isac and Isac-related nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the Isac and Isac-related gene product being expressed. For example, when a large quantity of such a protein is to be produced, for the generation of pharmaceutical compositions of Isac and Isac-related amino acid sequences or for raising antibodies that specifically bind to the Isac and Isac-related amino acid sequences, for example, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the Isac and Isac-related coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors may also be used to express foreign sequences as fusion proteins with glutathione S-transferase (GST). In general; such fusion proteins are soluble and can easily be purified from lysed cells by adsorption to glutathione-agarose beads followed by elution in the presence of free glutathione. The PGEX vectors are designed to include protease cleavage sites so that the cloned target gene product can be released from the GST moiety.

In an insect system, *Autographa californica* nuclear polyhidrosis virus (AcNPV) is used as a vector to express foreign genes. The virus grows in *Spodoptera frugiperda* cells. The Isac and Isac-related gene coding sequence may be cloned individually into non-essential regions (for example the polyhedrin gene) of the virus and placed under control of an AcNPV promoter (for example the polyhedrin promoter). Successful insertion of Isac and Isac-related gene coding sequence will result in inactivation of the polyhedrin gene and production of non-occluded recombinant virus, (i.e., virus lacking the proteinaceous coat coded for by the polyhedrin gene). These recombinant viruses are then used to infect *Spodoptera frugiperda* cells in which the inserted gene is expressed. (E.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the Isac and Isac-related nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the Isac and Isac-related gene product in infected hosts. (E.g., See Logan & Shenk, 1984, Proc. Natl. Acad. Sci. USA 81:3655–3659). Specific initiation signals may also be required for efficient translation of inserted Isac and Isac-related nucleotide sequences. These signals include the ATG initiation codon and adjacent sequences. In cases where an entire Isac gene or cDNA, including its own initiation codon and adjacent sequences, is inserted into the appropriate expression vector, no additional translational control signals may be needed. However, in cases where only a portion of the Isac coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, W138, and in particular, salivary gland cell lines.

For long-term, high-yield production of recombinant proteins, stable expression is preferred. For example, cell lines which stably express the Isac and Isac-related nucleotide sequences described above may be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the Isac and Isac-related gene product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk-, hgprt- or aprt-cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol.

Biol. 150:1); and hygro, which confers resistance to hygromycin (Santerre, et al., 1984, Gene 30:147).

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88: 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

Antibodies to Isac Proteins

Antibodies that specifically recognize one or more epitopes of Isac, or epitopes of conserved variants of Isac, or peptide fragments of Isac are also encompassed by the invention. Such antibodies include but are not limited to polyclonal antibodies, monoclonal antibodies (mAbs), humanized or chimeric antibodies, single chain antibodies, Fab fragments, F(ab')2 fragments, fragments produced by a Fab expression library, anti-idiotypic (anti-Id) antibodies, and epitope-binding fragments of any of the above.

The antibodies of the invention may be used, for example, for diagnostic purposes and for the identification of concentration levels of Isac in various biological fluids. Immunoassays utilizing these antibodies may be used as a diagnostic test, such as to detect infection of a mammalian host by a tick or to detect Isac from a tick in a tissue of the mammalian host. Also, such immunoassays may be used in the detection and isolation of Isac from tissue homogenates, cloned cells, and the like. Alternatively, antibodies against Isac can be used as a vaccine against tick infections in mammals. Or, antibodies can be used in conjunction with drug screening schemes.

For the production of antibodies, various host animals may be immunized by injection with Isac, an Isac peptide (e.g., one corresponding to a functional domain), truncated Isac proteins, polypeptides, or peptides, functional equivalents of Isac or variants of Isac. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Polyclonal antibodies are heterogeneous populations of antibody molecules derived from the sera of the immunized animals.

Monoclonal antibodies, which are homogeneous populations of antibodies to a particular antigen, may be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al, 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against Isac gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')2 fragments which can be produced by pepsin digestion of the antibody molecule and the Fab fragments which can be generated by reducing the disulfide bridges of the F(ab')2 fragments. Alternatively, Fab expression libraries may be constructed (Huse et al., 1989, Science, 246:1275–1281) to allow rapid and easy identification of monoclonal Fab fragments with the desired specificity.

Antibodies to Isac can, in turn, be utilized to generate anti-idiotype antibodies that "mimic" Isac, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a specific domain and competitively inhibit the binding of factor Bb and/or C3b can be used to generate anti-idiotypes that "mimic" the domain and, therefore, bind and neutralize Isac. Such neutralizing anti-idiotypes or Fab fragments of such anti-idiotypes can be used in regimens to neutralize Isac.

Diagnostic and Prognostic Assays of Isac

A variety of methods can be employed for the diagnostic and prognostic evaluation of Isac and Isac gene specific nucleic acid molecules for the identification and concentration levels of Isac and Isac gene specific nucleic acid molecules in various biological tissues and fluids. These assays may be used to detect infection of a mammalian host by a tick or to detect Isac from a tick in a tissue of a mammalian host. Also, such assays may be used in the detection of Isac expression patterns to aid in diagnosis and prognosis of pathological states associated with Isac.

Such methods may, for example, utilize reagents such as the Isac nucleotide sequences described above, Isac amino acid sequences described above, and Isac antibodies described above. Specifically, such reagents may be used, for example, for: (1) the detection of the presence of Isac expression or the detection of either an over- or under-expression of Isac mRNA; (2) the detection of the presence of Isac gene product or the detection of either an over- or under-abundance of Isac gene product; and (3) the detection of the presence of Isac antibodies.

The methods described herein may be performed, for example, by utilizing pre-packaged diagnostic kits comprising at least one specific Isac nucleotide sequence, Isac amino acid sequence or Isac antibody reagent described herein, which may be conveniently used, e.g., in clinical settings, to diagnose patients exhibiting a pathological state associated with Isac.

Information about Isac gene specific nucleic acid molecules can be detected by utilizing a number of techniques. Nucleic acid from any nucleated cell can be used as the starting point for such assay techniques, and may be isolated according to standard nucleic acid preparation procedures which are well known to those of skill in the art. The use of microarrays to determine gene expression requires DNA from the Isac gene that can serve as a probe for detecting which genes in the microarray are active in different types of cells.

DNA may be used in hybridization or amplification assays. Such assays may include, but are not limited to, Southern analyses, dot blots, single stranded conformational polymorphism analyses (SSCP), restriction fragment length polymorphisms (RFLPs) and PCR analyses.

Such diagnostic methods for the detection of Isac gene specific nucleic acid molecules can involve for example, contacting and incubating nucleic acids, including recombinant DNA molecules, cloned genes or degenerate variants thereof, obtained from a sample, e.g., derived from a patient sample or other appropriate cellular source, with one or more labeled nucleic acid reagents, including recombinant DNA molecules, cloned genes or degenerate variants thereof under conditions favorable for the specific annealing of these reagents to their complementary sequences within the Isac gene. Preferably, the lengths of these nucleic acid reagents are at least 15 to 30 nucleotides. After incubation, all non-annealed nucleic acids are removed from the nucleic acid:Isac molecule hybrid. The presence of nucleic acids which have hybridized, if any such molecules exist, is then detected. Using such a detection scheme, the nucleic acid from the cell type or tissue of interest can be immobilized, for example, to a solid support, such as a membrane, or a plastic surface such as that on a microtiter plate or polystyrene beads. In this case, after incubation, non-annealed, labeled nucleic acid reagents are easily removed. Detection of the remaining, annealed, labeled Isac nucleic acid reagents is accomplished using standard techniques well-known to those in the art. The Isac gene sequences to which the nucleic acid reagents have annealed can be compared to the annealing pattern expected from a control gene sequence in order to detect Isac gene specific nucleic acid molecules.

Alternative diagnostic methods for the detection of Isac gene specific nucleic acid molecules, in patient samples or other appropriate cell sources, may involve their amplification, e.g., by PCR (the experimental embodiment set forth in Mullis, K. B., 1987, U.S. Pat. No. 4,683,202), followed by the detection of the amplified molecules using techniques well known to those of skill in the art. The resulting amplified sequences can be compared to those which would be expected if the nucleic acid being amplified contained control gene copies in order to detect Isac gene specific nucleic acid molecules.

The level of Isac gene expression can also be assayed by detecting and measuring Isac transcription. For example, RNA from a cell type or tissue known, or suspected to express the Isac gene, such as salivary gland, may be isolated and tested utilizing hybridization or PCR techniques such as are described, above. The isolated cells can be derived from cell culture or from a patient. The analysis of cells taken from culture may be a necessary step in the assessment of cells to be used as part of a cell-based therapy or, alternatively, to test the effect of compounds on the expression of the Isac gene. Such analyses may reveal both quantitative and qualitative aspects of the expression pattern of the Isac gene, including activation or inactivation of Isac gene expression.

In one embodiment of such a detection scheme, cDNAs are synthesized from the RNAs of interest (e.g., by reverse transcription of the RNA molecule into cDNA). A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the Isac nucleic acid reagents described above. The preferred lengths of such nucleic acid reagents are at least 9–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Additionally, it is possible to perform such Isac gene expression assays "in situ", i.e., directly upon tissue sections (fixed and/or frozen) of patient tissue obtained from biopsies or resections, such that no nucleic acid purification is necessary. Nucleic acid reagents such as those described above may be used as probes and/or primers for such in situ procedures (See, for example, Nuovo, G. J., 1992, "PCR In Situ Hybridization: Protocols And Applications", Raven Press, NY).

Alternatively, if a sufficient quantity of the appropriate cells can be obtained, standard Northern analysis can be performed to determine the level of mRNA expression of the Isac gene.

Immunoassays and non-immunoassays for Isac gene products or conserved variants or peptide fragments thereof will typically comprise incubating a sample, such as a biological fluid, a tissue extract, freshly harvested cells, or lysates of cells which have been incubated in cell culture, in the presence of a detectably labeled antibody capable of identifying Isac gene products or conserved variants or peptide fragments thereof, and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled Isac antibody or Isac gene product. The solid phase support may then be washed with the buffer a second time to remove unbound antibody or gene product. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of Isac antibody or Isac gene product may be determined according to well known methods. Those skilled in the art will be able to determine operative and optimal assay conditions for each determination by employing routine experimentation.

With respect to antibodies, one of the ways in which the Isac antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2:1–7, Microbiological Associates Quarterly Publication, Walkersville, Md.); Voller, A. et al., 1978, J. Clin. Pathol. 31:507–520; Butler, J. E., 1981, Meth. Enzymol. 73:482–523; Maggio, E. (ed.), 1980, Enzyme Immunoassay, CRC Press, Boca Raton, Fla.; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alphaglycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect Isac through the use of a radioimmunoassay (RIA) (see, for example, Weintraub, B., Principles of Radioimmunoassays, Seventh Training Course on Radioligand Assay Techniques, The Endocrine Society, March, 1986). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}Eu$, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Screening Assays for Compounds that Bind Isac

The following assays are designed to identify compounds that interact with (e.g., bind to) Isac.

Such compounds may include, but are not limited to, peptides such as, for example, soluble peptides, including but not limited to members of random peptide libraries; (see, e.g., Lam, K. S. et al., 1991, Nature 354:82–84; Houghten, R. et al., 1991, Nature 354:84–86), and combinatorial chemistry-derived molecular library made of D- and/or L-configuration amino acids, phosphopeptides (including, but not limited to, members of random or partially degenerate, directed phosphopeptide libraries; see, e.g., Songyang, Z. et al., 1993, Cell 72:767–778), antibodies (including, but not limited to, polyclonal, monoclonal, humanized, anti-idiotypic, chimeric or single chain antibodies, and FAb, F(ab')2 and FAb expression library fragments, and epitope-binding fragments thereof), and small organic or inorganic molecules.

Computer modeling and searching technologies permit identification of compounds, or the improvement of already identified compounds, that can modulate Isac activity. Having identified such a compound or composition, the active sites or regions are identified. Such active sites might typically be ligand binding sites. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found. Next, the three dimensional geometric structure of the active site is determined. This can be done by known methods, including X-ray crystallography, which can determine a complete molecular structure. On the other hand, solid or liquid phase NMR can be used to determine certain intramolecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential Isac modulating compounds.

Alternatively, these methods can be used to identify improved modulating compounds from an already known modulating compound or ligand. The composition of the known compound can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active sites of Isac will be apparent to those of skill in the art.

Examples of molecular modeling systems are the CHARMM and QUANTA programs (Polygen Corporation, Waltham, Mass.). CHARMM performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific-proteins, such as Rotivinen, et al., 1988, Acta Pharmaceutical Fennica 97:159–166; Ripka, New Scientist 54–57 (Jun. 16, 1988); McKinaly and Rossmann, 1989, Annu. Rev. Pharmacol. Toxicol. 29:111–122; Perry and Davies, OSAR: Quantitative Structure-Activity Relationships in Drug Design pp. 189–193 (Alan R. Liss, Inc. 1989); Lewis and Dean, 1989 Proc. R. Soc. Lond. 236:125–140 and 141–162; and, with respect to a model receptor for nucleic acid components, Askew, et al., 1989, J. Am. Chem. Soc. 111:1082–1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although described above with reference to design and generation of compounds which could alter binding, one could also screen libraries of known compounds, including natural products or synthetic chemicals, and biologically active materials, including proteins, for compounds which are inhibitors or activators.

Compounds identified via assays such as those described herein may be useful, for example, in modulating the alternative complement pathway.

In Vitro Screening Assays

In vitro systems may be designed to identify compounds capable of interacting with (e.g., binding to) Isac. The principle of the assays used to identify compounds that bind to Isac involves preparing a reaction mixture of Isac and the test compound under conditions and for a time sufficient to allow the two components to interact and bind, thus forming a complex which can be removed and/or detected in the reaction mixture. The Isac species used can vary depending upon the goal of the screening assay.

The screening assays can be conducted in a variety of ways. For example, one method to conduct such an assay would involve anchoring the Isac protein, polypeptide, peptide or fusion protein or the test substance onto a solid phase and detecting Isac/test compound complexes anchored on the solid phase at the end of the reaction. In one embodiment of such a method, the Isac reactant may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for Isac protein, polypeptide, peptide or fusion protein or the test compound to anchor any complexes formed in solution, and a labeled antibody specific for the other component of the possible complex to detect anchored complexes.

In Vivo Screening Assays

In vivo systems may be designed to identify compounds capable of interacting with (e.g., binding to) Isac. One method which detects protein interactions in vivo, the two-hybrid system, is described in detail for illustration only and not by way of limitation. One version of this system has been described (Chien et al., 1991, Proc. Natl. Acad. Sci. USA, 88:9578–9582) and is commercially available from Clontech (Palo Alto, Calif.).

Briefly, utilizing such a system, plasmids are constructed that encode two hybrid proteins: one plasmid consists of nucleotides encoding the DNA-binding domain of a transcription activator protein fused to an Isac nucleotide sequence encoding Isac, an Isac polypeptide, peptide or fusion protein, and the other plasmid consists of nucleotides encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, Isac may be used as the bait gene product. Total genomic or cDNA sequences are fused to the DNA encoding an activation domain. This library and a plasmid encoding a hybrid of a bait Isac gene product fused to the DNA-binding domain are cotransformed into a yeast reporter strain, and the resulting transformants are screened for those that express the reporter gene. For example, and not by way of limitation, a bait Isac gene sequence, such as the open reading frame of Isac, can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait Isac gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait Isac gene-GAL4 fusion plasmid into a yeast strain which contains a lacZ gene driven by a promoter which contains GAL4 activation sequence. A cDNA encoded protein, fused to GAL4 transcriptional activation domain, that interacts with bait Isac gene product will reconstitute an active GAL4 protein and thereby drive expression of the HIS3 gene. Colonies which express HIS3 can be detected by their growth on Petri dishes containing semi-solid agar based media lacking histidine. The cDNA can then be purified from these strains, and used to produce and isolate the bait Isac gene-interacting protein using techniques routinely practiced in the art.

Assays for Compounds that Modulate the Interaction of Binding Partners with Isac The macromolecules that interact with Isac are referred to, for purposes of this discussion, as "binding partners". These binding partners are likely to be involved in the Isac mediated alternative complement pathway. Therefore, it is desirable to identify compounds that modulate the interaction of such binding partners with Isac.

The basic principle of the assay systems used to identify compounds that modulate the interaction between Isac and its binding partner (e.g., factor Bb, C3b, or C3b/Bb complex) involves preparing a reaction mixture containing Isac protein, polypeptide, peptide or fusion protein as described above, and the binding partner under conditions and for a time sufficient to allow the two to interact and bind, thus forming a complex. In order to test a compound for modulating activity, the reaction mixture is prepared in the presence and absence of the test compound. The test compound may be initially included in the reaction mixture, or may be added at a time subsequent to the addition of the Isac moiety and its binding partner. Control reaction mixtures are incubated without the test compound or with a placebo. The formation of any complexes between the Isac moiety and the binding partner is then detected. The formation of a complex in the control reaction, but not in the reaction mixture containing the test compound, indicates that the compound modulates the interaction of Isac and the interactive binding partner.

The assay for compounds that modulate the interaction of Isac and binding partners can be conducted in a heterogeneous or homogeneous format. Heterogeneous assays involve anchoring either the Isac moiety product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that inhibit the interaction by competition can be identified by conducting the reaction in the presence of the test substance; i.e., by adding the test substance to the reaction mixture prior to or simultaneously with the Isac moiety and interactive binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the Isac moiety or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the Isac gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment, a homogeneous assay can be used. In this approach, a preformed complex of the Isac moiety and the interactive binding partner is prepared in which either the Isac or its binding partners is labeled, but the signal generated by the label is quenched due to formation of the complex (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt Isac/binding partner interaction can be identified.

In a particular embodiment, an Isac fusion can be prepared for immobilization. For example, Isac or a peptide fragment, can be fused to a glutathione-S-transferase (GST) gene using a fusion vector, such as pGEX-5X-1, in such a manner that its binding activity is maintained in the resulting fusion protein. The interactive binding partner can be purified and used to raise a monoclonal antibody, using methods routinely practiced in the art and described above. This antibody can be labeled with the radioactive isotope 125I, for example, by methods routinely practiced in the art. In a heterogeneous assay, e.g., the GST-Isac fusion protein can be anchored to glutathione-agarose beads. The interactive binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the Isac gene product and the interactive binding partner can be detected by measuring the amount of radioactivity that remains associated with the glutathione-agarose beads. A successful inhibition of the interaction by the test compound will result in a decrease in measured radioactivity.

Alternatively, the GST-Isac fusion protein and the interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the Isac/binding partner interaction can be detected by adding the labeled antibody and measuring the radioactivity associated with the beads.

In another embodiment, these same techniques can be employed using peptide fragments that correspond to a specific domain of Isac and/or the interactive binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the binding partner is obtained, short gene segments can be engineered to express peptide fragments of the protein, which can then be tested for binding activity and purified or synthesized.

Assays for Identification of Compounds that Modulate Alternative Complement Pathway Compounds, including but not limited to binding compounds identified via assay techniques such as those described in the sections can be tested for the ability to modulate the alternative complement pathway. The assays described above can identify compounds which affect Isac activity (e.g., compounds that bind to Isac, inhibit binding of the natural ligand, and either activate signal transduction (agonists) or block activation (antagonists), and compounds that bind to the natural ligand of Isac and neutralize ligand activity). Such compounds can be used as part of a therapeutic regimen.

The invention encompasses cell-based and animal model-based assays for the identification of compounds exhibiting such an ability to modulate the alternative complement pathway.

Cell-based systems can be used to identify compounds which may act to modulate the alternative complement pathway. Such cell systems can include, for example, recombinant or non-recombinant cells, such as cell lines, which express microbial surfaces or other foreign surfaces. In addition, expression host cells (e.g., COS cells, CHO cells, fibroblasts) genetically engineered to express microbial surfaces or other foreign surfaces and to respond to activation by Isac, e.g., as measured by a chemical or phenotypic change, induction of another host cell gene, change in ion flux, tyrosine phosphorylation of host cell proteins, etc., can be used as an end point in the assay.

In addition, animal-based systems may be used to identify compounds capable of modulating the alternative complement pathway. Such animal models may be used as test substrates for the identification of pharmaceuticals, therapies and interventions which may be effective in such modulation. For example, animal models may be exposed to a compound, suspected of exhibiting an ability to modulate the alternative complement pathway, at a sufficient concentration and for a time sufficient to elicit such a modulation in the exposed animals. The response of the animals to the exposure may be monitored by assessing the responses associated with activation or deactivation of the alternative complement pathway.

Vaccine and Pharmaceutical Preparations and Methods of Administration and Other Uses The nucleic acid and amino acid compounds of the present invention are useful as pharmaceutical agents for modulating the alternative complement pathway in a mammal. This modulation of the alternative complement pathway includes facilitating or inhibiting complement activity. Preferred is inhibiting.

The nucleic acid and amino acid compounds can alternatively be used, with suitable adjuvants, as a gene or component vaccine against tick and tick-borne infections in mammals. Immunization with tick vaccine may be used in both the prophylaxis and therapy of parasitic infections. Disease conditions caused and transmitted by ticks may be treated by administering to an animal infected with these parasites anti-Isac antibody.

The vaccine or pharmaceutical compositions of the present invention are administered in vivo, ordinarily in a mammal, preferably in a human. In employing them in vivo, the vaccine or pharmaceutical compositions can be administered to a mammal in a variety of ways, including orally, parenterally, intravenously, subcutaneously, intramuscularly, colonically, rectally, nasally or intraperitoneally, employing a variety of dosage forms. Administration is preferably parenteral, such as intravenous on a daily basis. Alternatively, administration is preferably oral, such as by tablets, capsules or elixers taken on a daily basis.

In addition to the active ingredients, these vaccine and pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

Pharmaceutical formulations suitable for parenteral administration may be formulated in aqueous solutions, preferably in physiologically compatible buffers such as Hanks'solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

After pharmaceutical compositions have been prepared, they can be placed in an appropriate container and labeled for treatment of an indicated condition.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of cell lines, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example Isac or fragments thereof, antibodies of Isac, agonists, antagonists or etc of Isac, which ameliorates the symptoms or condition. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. For the present invention, alone or as part of a pharmaceutical composition, such doses are between about 0.01 mg/kg and 100 mg/kg body weight, preferably between about 0.01 and 10 mg/kg, body weight.

Purification, Cloning, and Expression

Figure 1B:
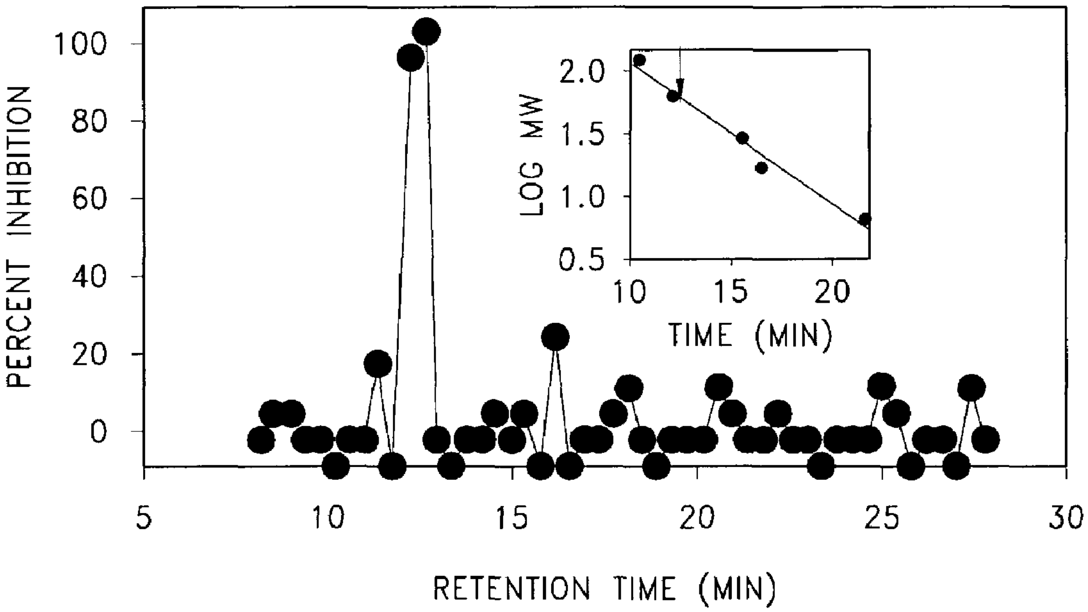

We initially attempted to purify *I. scapularis* salivary anticomplement from a 550 μl sample of pilocarpine-induced tick saliva. After one step of molecular sieving chromatography followed by reverse-phase HPLC on a polymeric column using a gradient of acetonitrile containing 8 mM HCl and a final step on the same column using trifluoroacetic acid instead of HCl, we obtained small amounts of a product with an amino terminal sequence (G) E D G L E (SEQ ID NO: 402, amino acids #22–27), where (G) was a doubtful result. Due to difficulties in collecting larger volumes of tick saliva, a second effort was made to purify the protein from tick salivary homogenates, which also possess anticomplement activity as determined by its ability to inhibit lysis of rabbit erythrocytes by human sera in the presence of $Mg^{++}$/EGTA. Accordingly, 500 pairs of salivary glands were homogenized in 50 ml HEPES saline, and the supernatant (after 10 min at 10,000×g) was concentrated using a 10-kDa cut-off Centricon (Millipore Corp.) filter. Ten aliquots of the concentrated homogenate were repeatedly injected into a molecular sieving column and the fractions collected into the same tubes at 0.4-min intervals. Two consecutive fractions were active, eluting with an apparent $M_r$ of 62 kDa (FIG. 1).

Figure 2A:
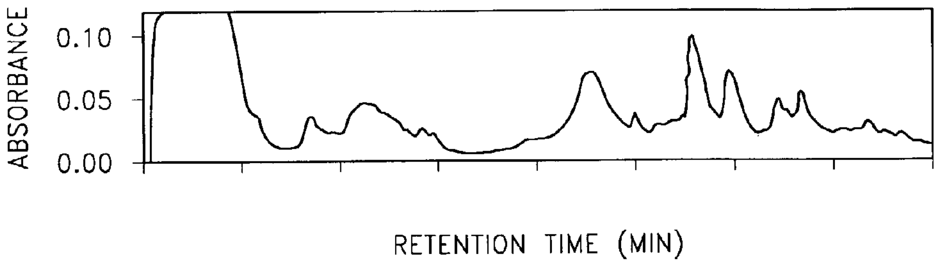
FIG. 2. Purification of *I. scapularis* salivary anticomplement. (A) UV absorbance at 220 nm from reverse phase-chromatography using HCl as a modifier, from ⅓ of active fractions obtained from the molecular sieving chromatography of 500 pairs of homogenized salivary glands from *I. scapularis*. (B) Anticomplement activity. (C) Reverse-phase chromatography using HCl as a modifier, of the combined active fractions obtained by reverse-phase chromatography as in A. (D) Anticomplement activity. (E) Reverse-phase chromatography using trifluoroacetic acid as a modifier, of the active fractions obtained by reverse-phase chromatography using HCl as a modifier. (F) Anticomplement activity.
Figure 2B:
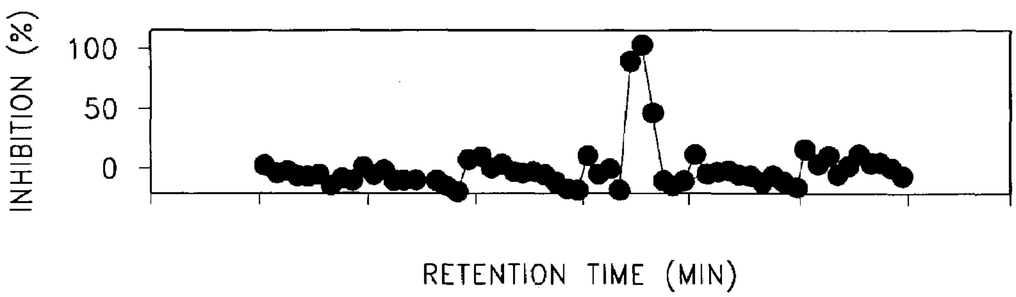
Figure 2C:
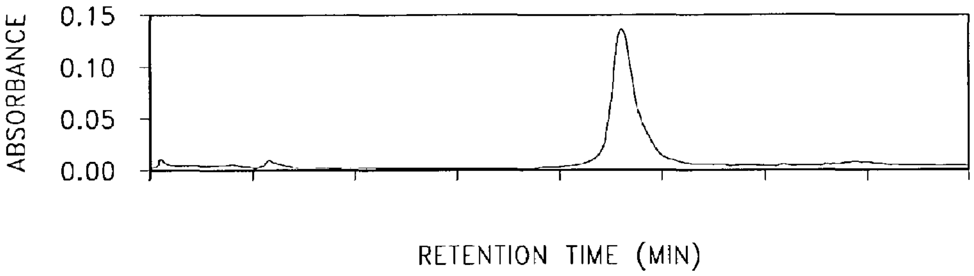
Figure 2D:
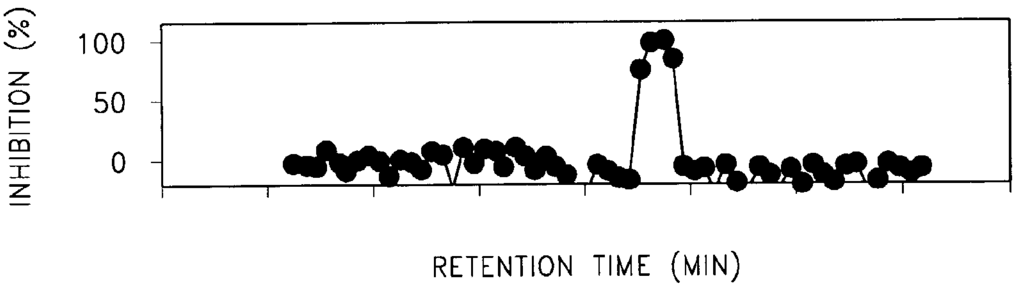
Figure 2E:
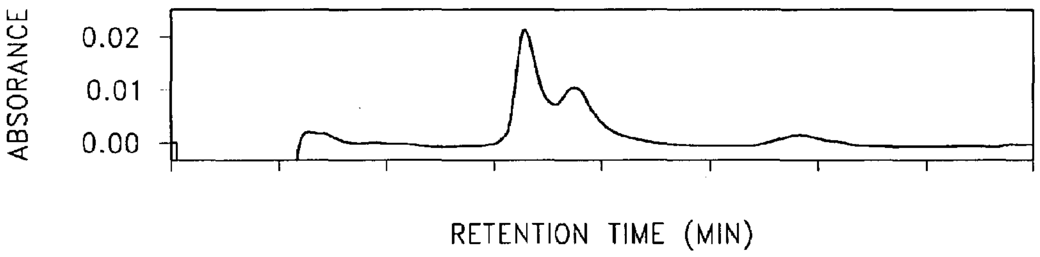
Figure 2F:
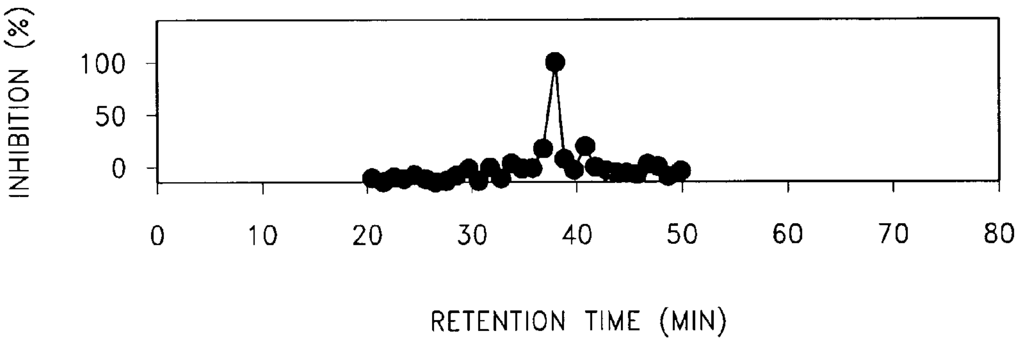

These active fractions were combined, and acetonitrile and HCl added to give 10% organic solvent and 8 mM of the acid. This fraction was further divided into three aliquots, each injected into a reverse-phase polymeric resin eluted with a gradient of acetonitrile in 8 mM HCl (FIG. 2A, B). Active fractions from these three reverse-phase columns were combined, diluted with water, and concentrated by passing over the same column again with a gradient of acetonitrile HCl to yield a single peak of UV-absorbing material (FIG. 2C, D). These fractions containing the UV-absorbing peak were combined and injected into the same column and eluted with a gradient of acetonitrile in 0.1% trifluoroacetic acid instead of HCl. Two UV-absorbing peaks eluted, the second of which had anticomplement activity (FIG. 2E, F). Fractions corresponding to the active peak were concentrated by evaporation and then sent for amino-terminal sequencing, which produced primary sequence (S/G) E D G L E Q D S K V E X X X Q N L Y E (SEQ ID NO: 402, amino acids #22–41). This sequence contained the shorter sequence obtained from HPLC purification of the anticomplement from tick saliva.

Attempts to obtain a PCR product using primers based on the above sequence failed, perhaps due to the high codon degeneracy presented by the majority of amino acids found in the sequence. A cDNA library from *I. scapularis* was randomly sequenced, and 709 sequences were obtained. This library is unidirectional with the cDNA being restricted with a rare cutter restriction enzyme (SfiI) before ligation to the vector. The probability of obtaining amino terminal information from the clones was enhanced by starting the cycle sequencing of the library's clones from the 5' region of the cDNA. In this manner, a clone was found leading to the predicted Isac protein shown in FIG. 3. The predicted protein has a putative signal peptide of 21 amino acids, the mature peptide having an amino terminal sequence in agreement with the measured sequence (FIG. 3). The predicted mature peptide has 163 amino acids, a theoretical pI of 4.48, and a $M_r$ of 18,136.77, assuming that no carboxyterminal residue beyond the terminal proline is lost. No significant similarities were found between Isac and any other protein in the GenBank database, when the BLASTX program invoking the BLOSUM 62 matrix was used (Altschul, S. F., Gish, W., Miller, W., Myers, E. W., and Lipman, D. J. (1990) J. Mol. Biol. 215(3), 403–410). The predicted Isac sequence has seven ASN glycosylation sites, seven casein kinase 2 phosphorylation sites and three myristoilation sites, as determined by scanning the Prosite database at www.expasy.ch.

Figure 4:
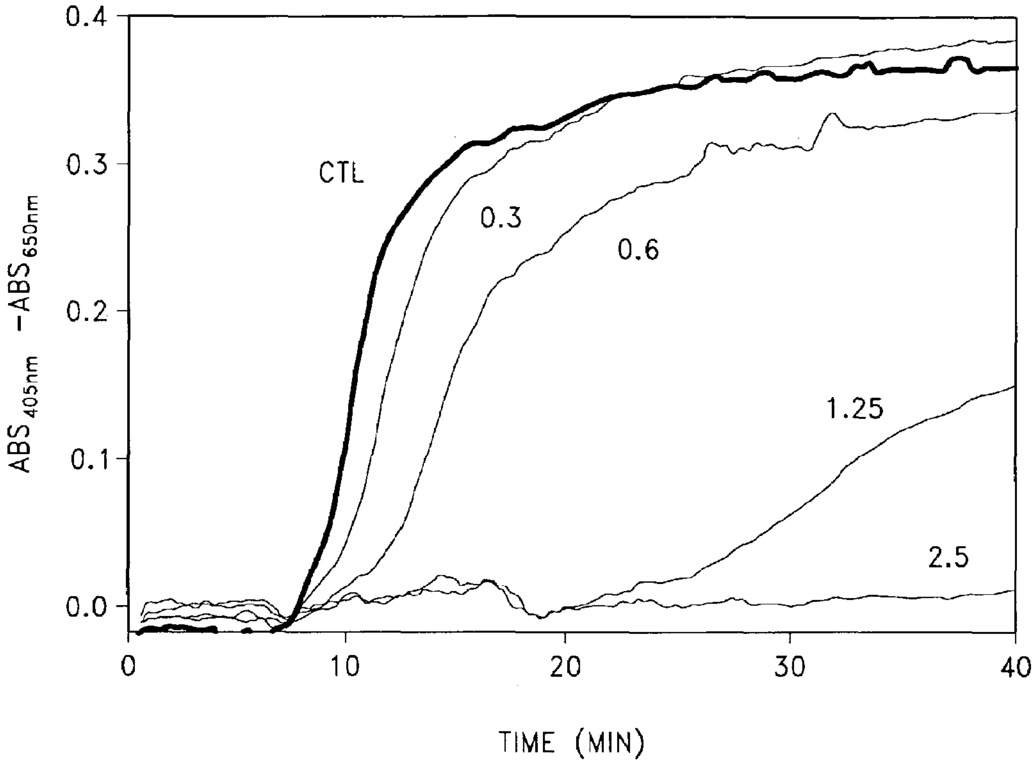
FIG. 4. Inhibition of rabbit erythrocyte lysis by human serum in the presence of different μl amounts (numbers) of COS cell supernatants transfected with R-Isac or C-Isac (control). The plate reader was blanked with wells containing 10 mM EDTA instead of EGTA and $MgCl_2$.

To confirm that the cDNA sequence corresponded to an anticomplement molecule, we expressed it in COS cells. Supernatants of cells transfected with r-Isac, but not those transfected with c-Isac, had anticomplement activity as measured by their ability to inhibit lysis of rabbit erythrocytes by human serum (FIG. 4).

Figure 5A:
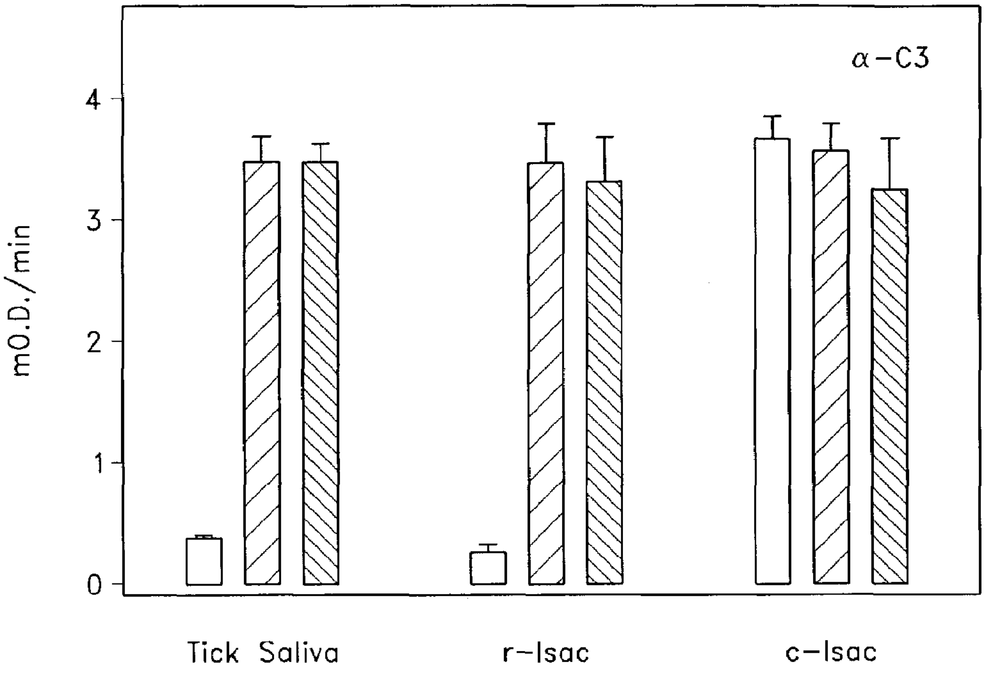
FIG. 5. Inhibition of C3b (A) and factor B (B) deposition to agarose-coated plates by *I. scapularis* saliva and r-Isac-transfected COS supernatants. Controls were run with supernatants of COS cells transfected with the c-Isac cDNA sequence. Blanks were obtained with wells incubated with 10 mM EDTA instead of EGTA and $MgCl_2$ during the complement activation step of the assay.
Figure 5B:
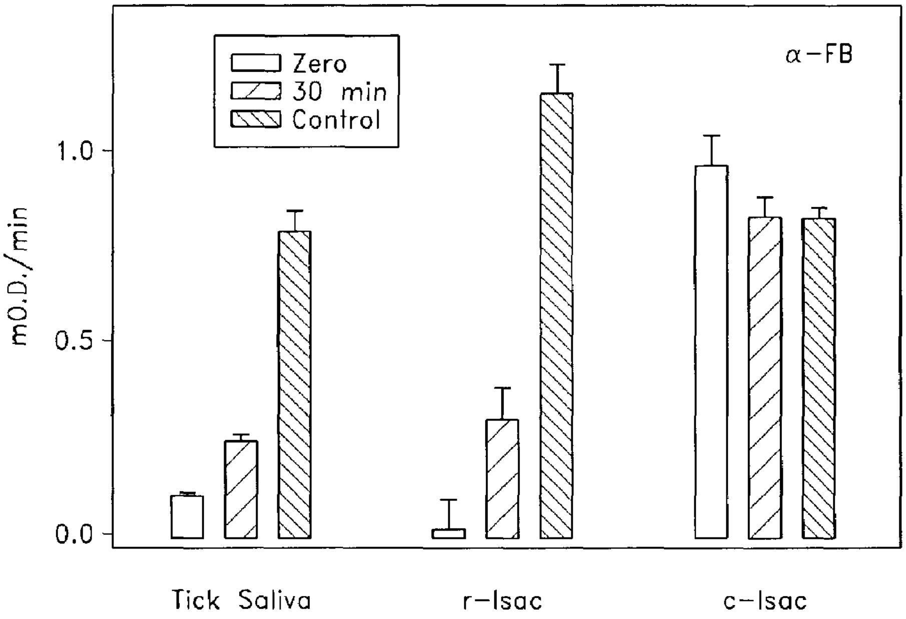
Figure 6A:
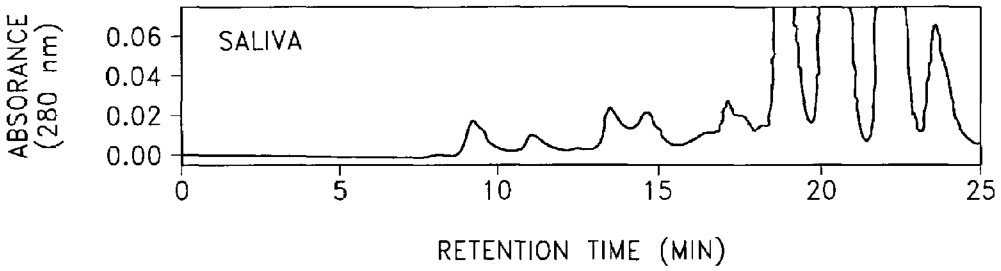
FIG. 6. Molecular sieving chromatography of 50 μl of *I. scapularis* saliva, or 50 μl of concentrated supernatant of COS-cells transfected with r-Isac or with c-Isac. UV absorbance of the chromatogram or inhibition of the lysis of rabbit erythrocytes by human sera in the presence of $Mg^{++}$/EGTA is shown.
Figure 6B:
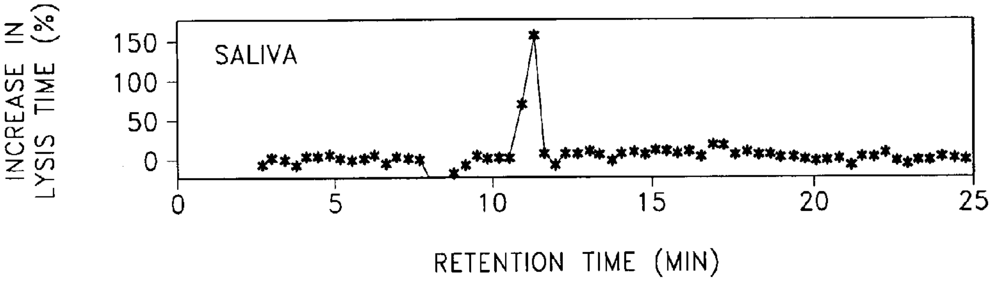
Figure 6C:
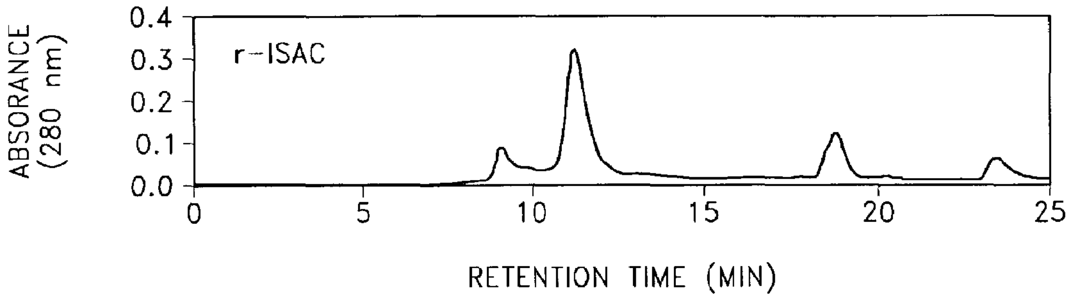
Figure 6D:
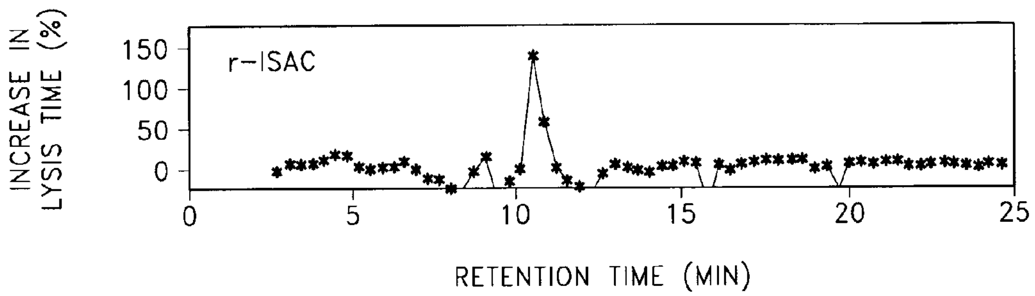
Figure 6E:
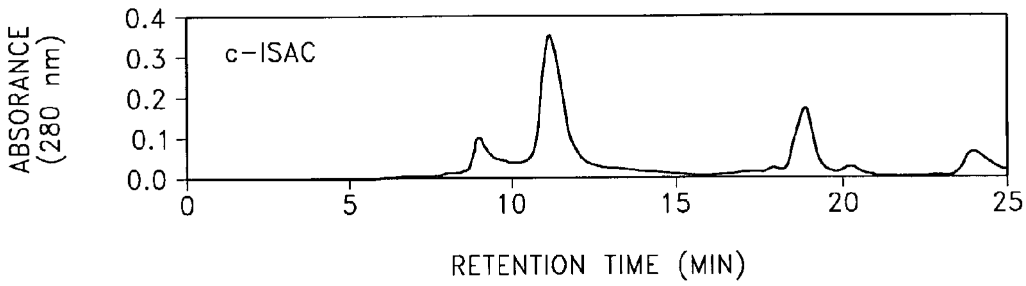
Figure 6F:
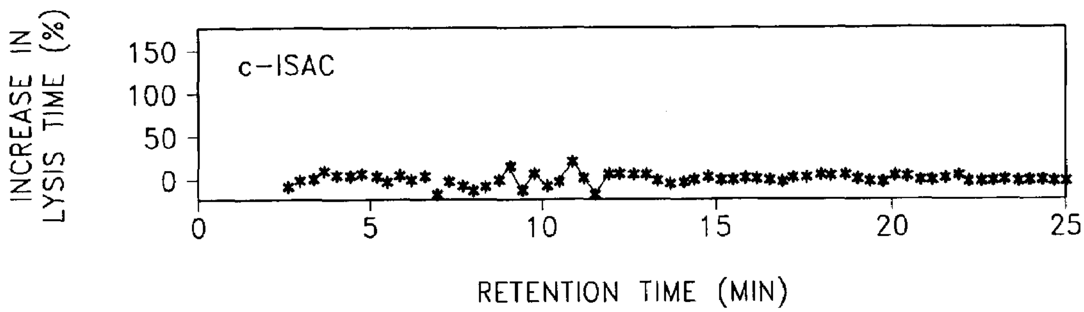

In the presence of $Mg^{++}$ and serum, C3 is deposited covalently to agarose via the alternative complement pathway (Joiner, K. A. (1988) Ann. Rev. Microbiol. 42, 201–230, Vogt, W. (1974) Pharmacol. Rev. 26, 125–169). Serum factor B (fB) binds noncovalently to agarose-bound C3b to form the C3 convertase of the alternative pathway, creating a positive feedback for further C3 activation and deposition. This assay is made specific to the alternative complement pathway by the presence of EGTA, a $Ca^{++}$ chelator, because calcium ions are needed for classical and lectin-mediated complement activation (Joiner, K. A. (1988) Ann. Rev. Microbiol. 42, 201–230). Based on these reactions, we developed a simple test for identification of alternative pathway-dependent C3 deposition to agarose and fB association with C3b using agarose coated microwells. Using this test, tick saliva and R-Isac cells prevented deposition of C3 to agarose-coated wells if added together with serum to the incubation mixture (FIG. 5); however, if added 30 min after addition of serum, C3 deposition (which is a covalent phenomenon) cannot be displaced by saliva- or Isac-transformed COS cell supernatants, although fB which attaches noncovalently to C3b, is significantly displaced by saliva or R-Isac.

To further compare the properties of r-Isac with the native protein, we submitted r-Isac and tick saliva to chromatography on a TSK-2000 SW column. Both activities eluted with similar retention time, although the recombinant protein eluted one fraction earlier in the chromatogram (FIG. 6). The observed retention times for both activities correspond to a $M_r$ of ~65 kDa, larger than the expected 18.5 kDa translation product deduced from Isac cDNA. This discrepancy may reflect the anomalous behavior of some proteins in silica-based molecular sieving columns, known to have residual silanol groups that may confer a cation exchange or anion exclusion capability to the column or, alternatively, Isac may be posttranslationally modified by glycosylation and/or polymerization. In either case, these results indicate the similarity in chromatographic behavior of r-Isac and the native protein.

Because Isac could be a serine protease inhibitor, we measured its activity on the classical pathway of complement activation using sensitized sheep erythrocytes. We also determined its effect on the recalcification time of citrated human plasma in an assay that measures both the intrinsic and the common pathway of the clotting cascade. Although *I. scapularis* saliva inhibited blood clotting, no effect of saliva was found on the classical pathway (triplicate experiment, using three saliva samples). Purified c-Isac, as well as the supernatant of r-Isac-transfected COS cells, did not have anticlotting or classical anticomplement activity in concentrations that fully inhibited the alternative complement pathway. These results indicate that Isac is different from the previously identified (but not molecularly characterized) unspecific antiprotease activity found in whole-body homogenates of the cattle tick, Boophilus microplus (Willadsen, P., and Riding, G. A. (1980) Biochem. J. 189, 295–303).

Isac behaves as a regulator of complement activation in a manner similar to decay accelerating factor and factor H, which inhibit complement activation by interacting with the C3 convertase of the classical or alternative pathway. Factor H is a 155-kDa glycoprotein containing 20 repetitive domains termed short consensus repeats (SCR) (Zipfel, P. F., Jokiranta, T. S., Hellwage, J., Koistinen, V., and Meri, S. (1999) Immunopharmacology 42(1–3), 53–60). In addition to its other effects on the complement cascade, factor H inhibits interaction of factor B with C3b (Zipfel, P. F., Jokiranta, T. S., Hellwage, J., Koistinen, V., and Meri, S. (1999) Immunopharmacology 42(1–3), 53–60), as does Isac. No significant sequence similarity was found, however, between Isac and factor H or with any other protein available in public domain databases. Isac may be structurally similar to a single SCR, and its four cysteines are consistent with the four cysteines conserved in SCRs of the factor H family (Zipfel, P. F., Jokiranta, T. S., Hellwage, J., Koistinen, V., and Meri, S. (1999) Immunopharmacology 42(1–3), 53–60). It would thus appear that Isac belongs to a new class of complement regulatory molecules. Successful expression of this protein makes it a viable target for anti-tick vaccines and pathological states.

EXAMPLE 1

Ticks

Tick saliva was obtained by inducing partially engorged adult female *I. scapularis* to salivate into capillary tubes using the pilocarpine induction method (Tatchell, R. J. (1967) J. Parasitol. 53, 1106–1107). Briefly, ticks engorging for 4–5 days on the ears of New Zealand white rabbits were harvested, rinsed in distilled water, and fixed to glass microscope slides with double-sided tape. A sterile glass micropipette was placed around the tick hypostome to collect saliva. Salivation was induced by applying 2 μl of pilocarpine (50 mg/ml in 95% ethanol) to the scutum of the tick. Ticks were incubated at 35° C. in a humid chamber until salivation ceased (2–3 h). Volumes ranged from 2.5 to 10 μl per tick. Tick salivary gland extracts were prepared by collecting glands from partially-engorged female *I. scapularis* as described. Glands were dissected by first bisecting the tick and then teasing the salivary glands away from the other internal organs and the tick exoskeleton. Glands were rinsed by immersion in HEPES-saline buffer (10 mM HEPES pH 7.0, 150 mM NaCl) and stored frozen at −75° C. until needed.

EXAMPLE 2

Reagents

Water was purified with a Milli-Q system from Millipore (Bedford, Mass.). Organic reagents were obtained from Sigma Chemical Co. (St. Louis, Mo.). Goat anti-human C3 antibody (cat. no. C-7761) was from Sigma Chemical Co. Goat anti-human factor B (cat. no. 31-785) was from Nordic Immunology (Tiburg, Netherlands). Rabbit anti-goat IgG, peroxidase conjugated and adsorbed against other human serum proteins (cat. no. A-4174, lot 78H9200), and anti-sheep erythrocyte stroma sera (part no. S 1389) were from Sigma Chemical Co. Agarose (ultraPure; GIBCO-BRL, Life Technologies, Rockville, Md.) was used to coat Immulon I micro plates (Dynatech Laboratories, Inc., Alexandria, Va.).

EXAMPLE 3

Erythrocyte Lysis Assays

To test for the alternative pathway of complement activation using rabbit erythrocytes and human serum (Platts-Mills, T. A. E., and Ishizaka, K. (1974) J. Immunol. 113, 348–358), rabbit erythrocytes in Alsever's solution (Spring Valley Labs, Woodbine, Md.) were washed five times with 10 vol of 150 mM NaCl, 10 mM HEPES pH 7.4 (HEPES saline), followed by centrifugation for 2 sec at 10,000× g. Reaction media, in a 96-well plate, contained 0.4% packed erythrocytes in 40 μl of 6.25 mM EGTA, 2.5 mM $MgCl_2$, 20 mM HEPES pH 7.4, and 150 mM NaCl. Additionally, 5 μl of the test sample or HEPES-saline control was added. In some cases, a larger amount of test sample was added, with corresponding changes in the buffer aliquot to keep the same concentrations of buffers, divalent cations, and chelators. A reaction was started with addition of 5 μl of human serum. Control reactions were run in which 12.5 mM EDTA was substituted for EGTA and $MgCl_2$. The plate was added to a Thermomax plate reader (Molecular Devices, Menlo Park, Calif.) set at 37° C. and was monitored at both 405 nm and 650 nm. The resulting value representing $[Abs_{405}-(Abs_{650}\times 1.5)]$ was plotted, and the time to achieve one-half of maximal lysis was determined from the curve. While the absorbance at 405 nm reflects the hemoglobin released by the cells, the absorbance at 650 nm controls for the turbidity change in the microwells. The value of 1.5 corrects for the decreased light scattering at the larger wavelength. In some cases, endpoint assays were done, the value representing the absorbance at 405 nm corrected for turbidity as above being taken as a measure of erythrocyte.

Assays to measure classical pathway lysis of sheep erythrocytes using anti-sheep erythrocyte antibody followed manufacturer's instructions (Sigma Chemical Co.). Briefly, washed sheep erythrocytes (50 μl of packed erythrocytes per ml) were incubated with 1:100 dilution of the sera for 20 min at 37° C., and stored at 4° C. until needed. The remainder of the assay was identical to that described above to detect alternative pathway-dependent lysis of rabbit erythrocytes as described above, except that 2 mM $CaCl_2$ was used instead of EGTA.

EXAMPLE 4

ELISA Assays for Measuring C3 and Factor B (fB)

To more specifically identify inhibitory activity within the complement cascade we measured complement deposition to agarose-coated wells in 96-well plates. Agarose activates the alternative pathway of complement (Vogt, W. (1974) Pharmacol. Rev. 26, 125–169). Plates were pretreated with 100 μl of 0.1% agarose in water (melted by boiling and kept at 50° C.) and incubated at 37° C. for 48 h, when dry. Wells were then incubated with 50 μl of 20 mM HEPES pH 7.4, 150 mM NaCl, 5 mM EGTA, 2 mM $MgCl_2$, and 10% human serum, containing 5 μl of the test solution or HEPES-saline. Control wells were run without serum or agarose coating, or 10 mM EDTA was substituted for $MgCl_2$ and EGTA. We chose to use the EDTA method as a routine blank for these assays. To reveal C3 or fB binding to the plate, plates were washed 5 times (3 min each washing, with slow orbital shaking of the plate) with 200 μl HEPES-saline containing 2 mM $MgCl_2$ and 10 mg/ml BSA, followed by addition of 100 μl of a 1:5,000 dilution of the anti-C3 or 1:250 dilution of the anti-fB antibody. These were incubated for 1 h at 37° C., washed 5 times as before, and the anti-goat peroxidase conjugate added at 1:5,000 dilution. Following incubation for 1 h at 37° C., the conjugate was washed twice each with HEPES saline containing 10 mg/ml BSA, then 0.1% Tween 20, then normal saline. Peroxidase activity was detected by adding a solution of HEPES saline containing 1 mg/ml ortho-phenylene-diamine (previously diluted in methanol to give 100 mg/ml), and 8.8 mM hydrogen peroxide. The rate of increase in absorption at 405 nm was measured in a Thermomax (Thermo Separation Products, Rivera Beach, Fla.) plate reader.

EXAMPLE 5

Human Plasma Recalcification Assay

To measure recalcification time of human plasma, 30 μl of human citrated plasma (0.38% final citrate concentration) was mixed with equal volumes of either test samples or HEPES saline in a 96-well plate. Reactions were initiated by adding 30 μl of 25 mM $CaCl_2$ to each mixture. The increase in turbidity at 650 nm was monitored in a Thermomax plate reader (Thermo Separation Products). Clotting time was determined as the time to reach 0.025 absorption units.

EXAMPLE 6

High-Performance Liquid Chromatography (HPLC) Procedures

Thermomax (Thermo Separation Products, Riviera Beach, Fla.) CM4000 or CM4100 pump was used in conjunction with a dual-wavelength UW-visible detector model SM4100 from the same company. Molecular sieving chromatography used a TSK-SW 2000 column (1 cm×80 cm for purification purpose or 0.43×25 cm for analytical purpose) (TosoHass, Montgomeryville, Pa.), eluted with 10 mM HEPES pH 7.0, 150 mM NaCl at the specified flow rates. Reverse-phase chromatography used one or two PRP-infinity columns linked in tandem, eluted at 0.5 ml/min with the indicated gradients of acetonitrile in 8 mM HCl or trifluoroacetic acid. HCl, as a modifier in reverse-phase chromatography, protonates and neutralizes the negatively charged protein carboxyl groups, thus increasing their hydrophobicity, but fails to form significant ion pairs of the positively charged amino groups with the chloride anion. TFA similarly causes protein protonation, but the anion forms significant ion pairs with the positively charged amino groups, and these ion pairs have increased hydrophobicity and consequent increased retention time. As a result, when a peptide mixture is run in reverse phase using HCl and TFA consecutively, the order of peptide elution may change according to differences in the charge of basic residues. Because TFA elution gives rise to sharper peaks, it is best that HCl elution is done first, followed by TFA elution, where the peaks are most concentrated. Silica-based octadecyl columns lead to complete loss of anticomplement activity. Fractions of the reverse-phase columns are dried in a SpeedVac-SC 110 (Savant Instruments, Inc., Holbrook, N.Y.) in the presence of 10 μg of BSA (in 10 μl of water) to prevent irreversible protein adsorption to the walls of the plastic tubes. Dried samples were resuspended in buffer.

EXAMPLE 7

Edman Degradation

Amino terminal sequencing of the HPLC-purified proteins was performed at the Harvard microsequencing facility.

EXAMPLE 8

Salivary Gland cDNA Library Construction

*I. scapularis* salivary gland mRNA was isolated from 25 pairs of salivary glands dissected from adult female ticks feeding for 3–4 days on a rabbit. We used the Micro-FastTrack mRNA isolation kit (Invitrogen, San Diego, Calif.), which yielded a total of 200 ng poly (A)+ mRNA. The polymerase chain reaction (PCR)-based cDNA library was made following the instructions for the SMART cDNA library construction kit (Clontech, Palo Alto, Calif.). *I. scapularis* salivary gland mRNA (200 ng) was reverse transcribed to cDNA for 1 h at 42° C. using Superscript II RNase H-reverse transcriptase (GIBCO-BRL) and the CDS/3' primer (Clontech). Second-strand synthesis was performed using a PCR-based protocol with the SMART III primer (Clontech) as the sense primer and the CDS/3' primer as anti-sense primer; these two primers contain, at the ends of the nascent cDNA, SfiI A and B sites, respectively. For double-stranded cDNA synthesis, we used a 9700 Thermalcycler (Perkin Elmer Corp., Foster City, Calif.) and Advantage Klen-Taq DNA polymerase (Clontech). PCR conditions were: 94° C. for 2 min; 18 cycles of 94° C. for 10 sec, and 68° C. for 6 min. Double-stranded cDNA was immediately treated with proteinase K (0.8 μg/μl) for 20 min at 45° C. and washed three times with water using Amicon filters with a 100 kDa cut-off (Millipore Corp.). The double-stranded cDNA was digested with SfiI for 2 h at 50° C. The SfiI sites were inserted to the cDNA during the second-strand synthesis using the SMART III and the CDS/3' primer and then fractionated using columns provided by the manufacturer (Clontech). Fractions containing cDNA of more than 400 bp were pooled, concentrated, and washed three times with water using an Amicon filter with a 100 kDa cut-off. The cDNA was concentrated to a final volume of 7 μl. The concentrated cDNA was ligated into a Lambda Triplex2 vector (Clontech), and the resulting ligation reaction was packed using Gigapack gold III from Stratagene/Biocrest (Cedar Creek, Tenn.) following manufacturer's specifications. The library obtained was plated by infecting log-phase XL1-blue cells (Clontech), and the percentage of recombinants was determined by PCR using vector primers flanking the inserted cDNA visualized on a 1.1% agarose gel with ethidium bromide (1.5 μg/ml).

EXAMPLE 9

Sequence of Isac

To isolate and sequence cDNA expressed by the salivary glands of *I. scapularis*, we developed a protocol intended to randomly match the cDNA to the N-terminus of the reverse phase HPLC-purified Isac. We plated the *I. scapularis* salivary gland cDNA library at a density of approximately 200 plaques/plate (150 mm Petri dish). The plaques were picked randomly and transferred to a 96-well polypropylene plate containing 100 μl of water/well. The plate was covered and placed on a gyrator shaker for 1 h at room temperature. Five μl of the phage sample was used as a template for a PCR reaction to amplify random cDNA. The primers for this reaction were sequences from the triplEX2 vector, named PT2F1 (5'-AAG TAC TCT AGC AAT TGT GAG C-3') (SEQ ID NO: 403), which is positioned upstream of the cDNA of interest (5' end), and PT2R1 (5'-CTC TTC GCT ATT ACG CCA GCT G-3') (SEQ ID NO: 404), which is positioned downstream of the cDNA of interest (3' end). High-fidelity platinum Taq polymerase (GIBCO-BRL) was used for these reactions. Amplification conditions were: 1 hold at 75° C. for 3 min, 1 hold at 94° C. for 3 min, and 34 cycles at 94° C. for 30 sec, 49° C. for 30 sec, and 72° C. for 1 min 20 sec. Amplified products were visualized on a 1.1% agarose gel with ethidium bromide. The concentration of double-strand cDNA was measured using Hoechst dye 33258 on a Flurolite 1000 plate fluorometer (Dynatech Laboratories, Chantilly, Va.). PCR reaction (3–4 ≯ ≯l1) containing between 100 to 200 ng of DNA were treated with Exonuclease I (0.5 U/μl) and shrimp alkaline phosphatase (0.1 U/μl) for 15 min at 37° C. and 15 minutes at 80° C. on a 96-well PCR plate. This mixture was used as a template for a cycle sequencing reaction using the DTCS labeling kit from Beckman Coulter Inc. (Fullerton, Calif.). The primer used for sequencing (PT2F3) is upstream of the inserted cDNA and downstream of the primer PT2F1. The sequencing reaction was performed in a Perkin Elmer 9700 Thermalcycler. Conditions were 75° C. for 2 min, 94° C. for 4 min, and 30 cycles at 96° C. for 20 sec, 50° C. for 20 sec, and 60° C. for 4 min. After cycle sequencing the samples, a cleaning step was done using the multi-screen 96-well plate-cleaning system (Millipore); this plate was prepared by adding a fixed amount (manufacturer's specification) of Sephadex-50 (Amersham Pharmacia Biotech, Piscataway, N.J.) and 300 µl of deionized water. After 1 h of incubation at room temperature, the water was removed from the multi-screen plate by centrifugation at 750 g for 5 min. After partially drying the Sephadex in the multi-screen plate, the whole cycle sequencing reaction was added to the center of each well, centrifuged at 750 g for 5 min, and the clean sample collected on a sequencing microtiter plate (Beckman Coulter, Inc.). The plate was dried using a SpeedVac SC 110 with a microtiter plate holder (Savant Instruments Inc.). The dried samples were immediately resuspended with 25 µl of deionized ultraPure formamide (J. T. Baker, Phillipsburg, N.J.), and one drop of mineral oil was added to the top of each sample. Samples were either sequenced immediately on a CEQ 2000 DNA sequencing instrument (Beckman Coulter Inc.) or stored at −30° C.

EXAMPLE 10

Isolation of Isac and Construction of Expression Vector

We identified the cDNA with an open reading frame matching the N-terminus of the reverse-phase HPLC-purified Isac. An aliquot (~100 ng) of Isac PCR sample was reamplified using the PT2F1 and PT2R1 primers (conditions as above, but only 25 PCR cycles), and the entire cDNA was fully sequenced as described above on a CEQ 2000 using custom primers. Isac cDNA was cloned into a TOPO TA cloning vector (Invitrogen). For expression of Isac, full-length cDNA was used as a template to amplify only the cDNA fragment that began with the initial methionine and ended at the first stop codon. The single product amplified was immediately cloned into the eukaryotic cloning vector pcDNA3.1/V5/His-TOPO (Invitrogen) following manufacturer's specifications. The ligation mixture was used to transform TOP10 cells (Invitrogen) and the cells were incubated overnight at 37 C. Eight colonies were selected and mixed with 10 µl of sterile water. Five 5 µl of each sample were transferred to Luria broth (LB) containing ampicillin (100 µg/ml), and grown at 37 C. The other 5 µl were used as a template for a PCR reaction using two vector-specific primers from the pcDNA3.1/V5/His-TOPO vector to confirm the presence of the insert and for sequencing analysis. After visualizing the PCR product on a 1.1% agarose gel, we completely sequenced the eight PCR products as described above with a CEQ2000 (Beckman Coulter Inc.). We chose two samples for expression in this vector, one containing the complete sequence (from methionine to stop codon) in the correct orientation of Isac (R-Isac, recombinant Isac), and a second containing the Isac complete sequence in reverse orientation, which became our control (C-Isac, control Isac). Cells containing the sample and control were grown overnight at 37° C. on LB with ampicillin (100 µg/ml), and plasmid isolation was performed with the Wizard miniprep kit (Promega Corporation, Madison, Wis.). After plasmid isolation, the sample and control plasmids were washed three times with ultraPure water using an Amicon-100 (Millipore), measured, and stored before attempting to transform COS-7 cells.

EXAMPLE 11

Expression of Isac in COS Cells

COS-7 cells (ATCC CRL 1651) were cultivated in Dulbecco's modified Eagle's medium supplemented with 4 mM glutamine, antibiotics, and 10% heat-inactivated fetal calf serum (complete medium) as previously described (Valenzuela, J. G., Charlab, R., Galperin, M. Y., and Ribeiro, J. M. (1998) J. Biol. Chem. 273(46), 30583–30590). Subconfluent COS-7 cells were transfected with Isac EDNA (R-Isac) or with the Isac in reverse orientation (C-Isac). Transfections were performed with the Bio-Rad (Hercules, Calif.) electroporation system using 200 V and 1000 mF in a 0.4-cm gap cuvette. DNA (200 µg and 400 µg) was used for each transfection at a cell density of $10^7$/ml. After electroporation, the cells were allowed to sit for 10 min at room temperature, then were placed into 10 ml complete medium in a 75 cm2 culture flask at 37 C/5% $CO_2$. After a 16-h incubation, the supernatants were collected and 10 ml of serum-free Dulbecco's modified Eagle's medium added to the cultures. This procedure was repeated daily up to 3 days after transfection. The resultant supernatants were centrifuged at 10,000 g for 5 min, concentrated 20-fold on Centricon Plus-20 (5-kDa cut-off) (Millipore Corp.) and kept at −20° C. for bioassays. Control cells were transfected with the Isac in reverse orientation construct (C-Isac), and supernatants were obtained as for the R-Isac transfected cells.

EXAMPLE 12

Sequence Analysis

Sequence similarity searches were performed using the Blast (Altschul, S. F., Gish, W., Miller, W., Myers, E. W., and Lipman, D. J. (1990) J. Mol. Biol. 215(3), 403–410) program. Cleavage site predictions of the mature proteins used the SignalP program (Nielsen, H., Engelbrecht, J., Brunak, S., and von Heijne, G. (1997) Protein Eng. 10(1), 1–6).

While the present invention has been described in some detail for purposes of clarity and understanding, one skilled in the art will appreciate that various changes in form and detail can be made without departing from the true scope of the invention. All references referred to above are hereby incorporated by reference.

APPENDIX A

Table I

Table I shows Isac carboxy truncations.

In this table "X" may represent an amino group, a hydrophobic group, including but not limited to carbobenzoxyl, dansyl, or T-butyloxycarbonyl; an acetyl group; a 9-fluorenylmethoxy-carbonyl (FMOC); a macromolecular carrier group including but not limited to lipid-fatty acid conjugates, polyethylene glycol, or carbohydrates.

Additionally, in this table "Z" may represent a carboxyl group; an amino group; a T-butyloxycarbonyl group; a macromolecular carrier group including but not limited to lipid-fatty acid conjugates, polyethylene glycol, or carbohydrates.

TABLE I

| Carboxy Truncations |
|---|
| X-SED-Z (SEQ ID NO 1) |
| X-SEDG-Z (SEQ ID NO 2) |
| X-SEDGL-Z (SEQ ID NO 3) |
| X-SEDGLE-Z (SEQ ID NO 4) |
| X-SEDGLEQ-Z (SEQ ID NO 5) |
| X-SEDGLEQD-Z (SEQ ID NO 6) |
| X-SEDGLEQDT-Z (SEQ ID NO 7) |
| X-SEDGLEQDTI-Z (SEQ ID NO 8) |
| X-SEDGLEQDTIV-Z (SEQ ID NO 9) |
| X-SEDGLEQDTIVE-Z (SEQ ID NO 10) |
| X-SEDGLEQDTIVET-Z (SEQ ID NO 11) |
| X-SEDGLEQDTIVETT-Z (SEQ ID NO 12) |
| X-SEDGLEQDTIVETTT-Z (SEQ ID NO 13) |
| X-SEDGLEQDTIVETTTQ-Z (SEQ ID NO 14) |
| X-SEDGLEQDTIVETTTQN-Z (SEQ ID NO 15) |
| X-SEDGLEQDTIVETTTQNL-Z (SEQ ID NO 16) |
| X-SEDGLEQDTIVETTTQNLY-Z (SEQ ID NO 17) |
| X-SEDGLEQDTIVETTTQNLYE-Z (SEQ ID NO 18) |
| X-SEDGLEQDTIVETTTQNLYER-Z (SEQ ID NO 19) |
| X-SEDGLEQDTIVETTTQNLYERH-Z (SEQ ID NO 20) |
| X-SEDGLEQDTIVETTTQNLYERHY-Z (SEQ ID NO 21) |
| X-SEDGLEQDTIVETTTQNLYERHYR-Z (SEQ ID NO 22) |
| X-SEDGLEQDTIVETTTQNLYERHYRN-Z (SEQ ID NO 23) |
| X-SEDGLEQDTIVETTTQNLYERHYRNH-Z (SEQ ID NO 24) |
| X-SEDGLEQDTIVETTTQNLYERHYRNHS-Z (SEQ ID NO 25) |
| X-SEDGLEQDTIVETTTQNLYERHYRNHSG-Z (SEQ ID NO 26) |
| X-SEDGLEQDTIVETTTQNLYERHYRNHSGL-Z (SEQ ID NO 27) |
| X-SEDGLEQDTIVETTTQNLYERHYRNHSGLC-Z (SEQ ID NO 28) |
| X-SEDGLEQDTIVETTTQNLYERHYRNHSGLCG-Z (SEQ ID NO 29) |
| X-SEDGLEQDTIVETTTQNLYERHYRNHSGLCGA-Z (SEQ ID NO 30) |
| X-SEDGLEQDTIVETTTQNLYERHYRNHSGLCGAQ-Z (SEQ ID NO 31) |
| X-SEDGLEQDTIVETTTQNLYERHYRNHSGLCGAQY-Z (SEQ ID NO 32) |
| X-SEDGLEQDTIVETTTQNLYERHYRNHSGLCGAQYR-Z (SEQ ID NO 33) |
| X-SEDGLEQDTIVETTTQNLYERHYRNHSGLCGAQYRN-Z (SEQ ID NO 34) |
| X-SEDGLEQDTIVETTTQNLYERHYRNHSGLCGAQYRNS-Z (SEQ ID NO 35) |
| X-SEDGLEQDTIVETTTQNLYERHYRNHSGLCGAQYRNSS-Z (SEQ ID NO 36) |
| X-SEDGLEQDTIVETTTQNLYERHYRNHSGLCGAQYRNSSH-Z (SEQ ID NO 37) |
| X-SEDGLEQDTIVETTTQNLYERHYRNHSGLCGAQYRNSSHA-Z (SEQ ID NO 38) |
| X-SEDGLEQDTIVETTTQNLYERHYRNHSGLCGAQYRNSSHAE-Z (SEQ ID NO 39) |

TABLE I-continued

| Carboxy Truncations |
|---|
| X-SEDGLEQDTIVETTTQNLYERHYRNHSGLCGAQYRNSSHAEA-Z (SEQ ID NO 40) |
| X-SEDGLEQDTIVETTTQNLYERHYRNHSGLCGAQYRNSSHAEAV-Z (SEQ ID NO 41) |
| X-SEDGLEQDTIVETTTQNLYERHYRNHSGLCGAQYRNSSHAEAVY-Z (SEQ ID NO 42) |
| X-SEDGLEQDTIVETTTQNLYERHYRNHSGLCGAQYRNSSHAEAVYN-Z (SEQ ID NO 43) |
| X-SEDGLEQDTIVETTTQNLYERHYRNHSGLCGAQYRNSSHAEAVYNC-Z (SEQ ID NO 44) |
| X-SEDGLEQDTIVETTTQNLYERHYRNHSGLCGAQYRNSSHAEAVYNCT-Z (SEQ ID NO 45) |
| X-SEDGLEQDTIVETTTQNLYERHYRNHSGLCGAQYRNSSHAEAVYNCTL-Z (SEQ ID NO 46) |
| X-SEDGLEQDTIVETTTQNLYERHYRNHSGLCGAQYRNSSHAEAVYNCTLN-Z (SEQ ID NO 47) |
| X-SEDGLEQDTIVETTTQNLYERHYRNHSGLCGAQYRNSSHAEAVYNCTLNH-Z (SEQ ID NO 48) |
| X-SEDGLEQDTIVETTTQNLYERHYRNHSGLCGAQYRNSSHAEAVYNCTLNHL-Z (SEQ ID NO 49) |
| X-SEDGLEQDTIVETTTQNLYERHYRNHSGLCGAQYRNSSHAEAVYNCTLNHLP-Z (SEQ ID NO 50) |
| X-SEDGLEQDTIVETTTQNLYERHYRNHSGLCGAQYRNSSHAEAVYNCTLNHLPP-Z (SEQ ID NO 51) |
| X-SEDGLEQDTIVETTTQNLYERHYRNHSGLCGAQYRNSSHAEAVYNCTLNHLPPV-Z (SEQ ID NO 52) |
| X-SEDGLEQDTIVETTTQNLYERHYRNHSGLCGAQYRNSSHAEAVYNCTLNHLPPVV-Z (SEQ ID NO 53) |
| X-SEDGLEQDTIVETTTQNLYERHYRNHSGLCGAQYRNSSHAEAVYNCTLNHLPPVVN-Z (SEQ ID NO 54) |
| X-SEDGLEQDTIVETTTQNLYERHYRNHSGLCGAQYRNSSHAEAVYNCTLNHLPPVVNA-Z (SEQ ID NO 55) |
| X-SEDGLEQDTIVETTTQNLYERHYRNHSGLCGAQYRNSSHAEAVYNCTLNHLPPVVNAT-Z (SEQ ID NO 56) |
| X-SEDGLEQDTIVETTTQNLYERHYRNHSGLCGAQYRNSSHAEAVYNCTLNHLPPVVNATW-Z (SEQ ID NO 57) |
| X-SEDGLEQDTIVETTTQNLYERHYRNHSGLCGAQYRNSSHAEAVYNCTLNHLPPVVNATWE-Z (SEQ ID NO 58) |
| X-SEDGLEQDTIVETTTQNLYERHYRNHSGLCGAQYRNSSHAEAVYNCTLNHLPPVVNATWEG-Z (SEQ ID NO 59) |
| X-SEDGLEQDTIVETTTQNLYERHYRNHSGLCGAQYRNSSHAEAVYNCTLNHLPPVVNATWEGI-Z (SEQ ID NO 60) |
| X-SEDGLEQDTIVETTTQNLYERHYRNHSGLCGAQYRNSSHAEAVYNCTLNHLPPVVNATWEGIR-Z (SEQ ID NO 61) |
| X-SEDGLEQDTIVETTTQNLYERHYRNHSGLCGAQYRNSSHAEAVYNCTLNHLPPVVNATWEGIRH-Z (SEQ ID NO 62) |
| X-SEDGLEQDTIVETTTQNLYERHYRNHSGLCGAQYRNSSHAEAVYNCTLNHLPPVVNATWEGIRHR-Z (SEQ ID NO 63) |
| X-SEDGLEQDTIVETTTQNLYERHYRNHSGLCGAQYRNSSHAEAVYNCTLNHLPPVVNATWEGIRHRI-Z (SEQ ID NO 64) |
| X-SEDGLEQDTIVETTTQNLYERHYRNHSGLCGAQYRNSSHAEAVYNCTLNHLPPVVNATWEGIRHRIN-Z (SEQ ID NO 65) |
| X-SEDGLEQDTIVETTTQNLYERHYRNHSGLCGAQYRNSSHAEAVYNCTLNHLPPVVNATWEGIRHRINK-Z (SEQ ID NO 66) |
| X-SEDGLEQDTIVETTTQNLYERHYRNHSGLCGAQYRNSSHAEAVYNCTLNHLPPVVNATWEGIRHRINKT-Z (SEQ ID NO 67) |
| X-SEDGLEQDTIVETTTQNLYERHYRNHSGLCGAQYRNSSHAEAVYNCTLNHLPPVVNATWEGIRHRINKTI-Z (SEQ ID NO 68) |
| X-SEDGLEQDTIVETTTQNLYERHYRNHSGLCGAQYRNSSHAEAVYNCTLNHLPPVVNATWEGIRHRINKTIP-Z (SEQ ID NO 69) |
| X-SEDGLEQDTIVETTTQNLYERHYRNHSGLCGAQYRNSSHAEAVYNCTLNHLPPVVNATWEGIRHRINKTIPQ-Z (SEQ ID NO 70) |
| X-SEDGLEQDTIVETTTQNLYERHYRNHSGLCGAQYRNSSHAEAVYNCTLNHLPPVVNATWEGIRHRINKTIPQF-Z (SEQ ID NO 71) |
| X-SEDGLEQDTIVETTTQNLYERHYRNHSGLCGAQYRNSSHAEAVYNCTLNHLPPVVNATWEGIRHRINKTIPQFV-Z (SEQ ID NO 72) |
| X-SEDGLEQDTIVETTTQNLYERHYRNHSGLCGAQYRNSSHAEAVYNCTLNHLPPVVNATWEGIRHRINKTIPQFVK-Z (SEQ ID NO 73) |
| X-SEDGLEQDTIVETTTQNLYERHYRNHSGLCGAQYRNSSHAEAVYNCTLNHLPPVVNATWEGIRHRINKTIPQFVKL-Z (SEQ ID NO 74) |
| X-SEDGLEQDTIVETTTQNLYERHYRNHSGLCGAQYRNSSHAEAVYNCTLNHLPPVVNATWEGIRHRINKTIPQFVKLI-Z (SEQ ID NO 75) |
| X-SEDGLEQDTIVETTTQNLYERHYRNHSGLCGAQYRNSSHAEAVYNCTLNHLPPVVNATWEGIRHRINKTIPQFVKLIC-Z (SEQ ID NO 76) |
| X-SEDGLEQDTIVETTTQNLYERHYRNHSGLCGAQYRNSSHAEAVYNCTLNHLPPVVNATWEGIRHRINKTIPQFVKLICN-Z (SEQ ID NO 77) |

TABLE I-continued

| Carboxy Truncations |
| --- |
| X-SEDGLEQDTIVETTTQNLYERHYRNHSGLCGAQYRNSSHAEAVYNCTLNHLPPVVNATWEGIRHRINKTIPQFVKLICNF-Z (SEQ ID NO 78) |
| X-SEDGLEQDTIVETTTQNLYERHYRNHSGLCGAQYRNSSHAEAVYNCTLNHLPPVVNATWEGIRHRINKTIPQFVKLICNFT-Z (SEQ ID NO 79) |
| X-SEDGLEQDTIVETTTQNLYERHYRNHSGLCGAQYRNSSHAEAVYNCTLNHLPPVVNATWEGIRHRINKTIPQFVKLICNFTV-Z (SEQ ID NO 80) |
| X-SEDGLEQDTIVETTTQNLYERHYRNHSGLCGAQYRNSSHAEAVYNCTLNHLPPVVNATWEGIRHRINKTIPQFVKLICNFTVA-Z (SEQ ID NO 81) |
| X-SEDGLEQDTIVETTTQNLYERHYRNHSGLCGAQYRNSSHAEAVYNCTLNHLPPVVNATWEGIRHRINKTIPQFVKLICNFTVAM-Z (SEQ ID NO 82) |
| X-SEDGLEQDTIVETTTQNLYERHYRNHSGLCGAQYRNSSHAEAVYNCTLNHLPPVVNATWEGIRHRINKTIPQFVKLICNFTVAMP-Z (SEQ ID NO 83) |
| X-SEDGLEQDTIVETTTQNLYERHYRNHSGLCGAQYRNSSHAEAVYNCTLNHLPPVVNATWEGIRHRINKTIPQFVKLICNFTVAMPQ-Z (SEQ ID NO 84) |
| X-SEDGLEQDTIVETTTQNLYERHYRNHSGLCGAQYRNSSHAEAVYNCTLNHLPPVVNATWEGIRHRINKTIPQFVKLICNFTVAMPQE-Z (SEQ ID NO 85) |
| X-SEDGLEQDTIVETTTQNLYERHYRNHSGLCGAQYRNSSHAEAVYNCTLNHLPPVVNATWEGIRHRINKTIPQFVKLICNFTVAMPQEF-Z (SEQ ID NO 86) |
| X-SEDGLEQDTIVETTTQNLYERHYRNHSGLCGAQYRNSSHAEAVYNCTLNHLPPVVNATWEGIRHRINKTIPQFVKLICNFTVAMPQEFY-Z (SEQ ID NO 87) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYL-Z (SEQ ID NO 88) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLV-Z (SEQ ID NO 89) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVY-Z (SEQ ID NO 90) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYM-Z (SEQ ID NO 91) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMG-Z (SEQ ID NO 92) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGS-Z (SEQ ID NO 93) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSD-Z (SEQ ID NO 94) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDG-Z (SEQ ID NO 95) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGN-Z (SEQ ID NO 96) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNS-Z (SEQ ID NO 97) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSD-Z (SEQ ID NO 98) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF-Z (SEQ ID NO 99) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDFE-Z (SEQ ID NO 100) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDFEE-Z (SEQ ID NO 101) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDFEED-Z (SEQ ID NO 102) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDFEEDK-Z (SEQ ID NO 103) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDFEEDKE-Z (SEQ ID NO 104) |

TABLE I-continued

| Carboxy Truncations |
|---|
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKES-Z (SEQ ID NO 105) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKEST-Z (SEQ ID NO 106) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTG-Z (SEQ ID NO 107) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGT-Z (SEQ ID NO 108) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTD-Z (SEQ ID NO 109) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDE-Z (SEQ ID NO 110) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDED-Z (SEQ ID NO 111) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDEDS-Z (SEQ ID NO 112) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDEDSN-Z (SEQ ID NO 113) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDEDSNT-Z (SEQ ID NO 114) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDEDSNTG-Z (SEQ ID NO 115) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDEDSNTGS-Z (SEQ ID NO 116) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDEDSNTGSS-Z (SEQ ID NO 117) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDEDSNTGSSA-Z (SEQ ID NO 118) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDEDSNTGSSAA-Z (SEQ ID NO 119) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDEDSNTGSSAAA-Z (SEQ ID NO 120) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDEDSNTGSSAAAK-Z (SEQ ID NO 121) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDEDSNTGSSAAAKV-Z (SEQ ID NO 122) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDEDSNTGSSAAAKVT-Z (SEQ ID NO 123) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDEDSNTGSSAAAKVTE-Z (SEQ ID NO 124) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDEDSNTGSSAAAKVTEA-Z (SEQ ID NO 125) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDEDSNTGSSAAAKVTEAL-Z (SEQ ID NO 126) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDEDSNTGSSAAAKVTEALI-Z (SEQ ID NO 127) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDEDSNTGSSAAAKVTEALII-Z (SEQ ID NO 128) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDEDSNTGSSAAAKVTEALIIE-Z (SEQ ID NO 129) |

TABLE I-continued

| Carboxy Truncations |
| --- |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF<br>EEDKESTGTDEDSNTGSSAAAKVTEALIIEA-Z (SEQ ID NO 130) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF<br>EEDKESTGTDEDSNTGSSAAAKVTEALIIEAE-Z (SEQ ID NO 131) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF<br>EEDKESTGTDEDSNTGSSAAAKVTEALIIEAEE-Z (SEQ ID NO 132) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF<br>EEDKESTGTDEDSNTGSSAAAKVTEALIIEAEEN-Z (SEQ ID NO 133) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF<br>EEDKESTGTDEDSNTGSSAAAKVTEALIIEAEENC-Z (SEQ ID NO 134) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF<br>EEDKESTGTDEDSNTGSSAAAKVTEALIIEAEENCT-Z (SEQ ID NO 135) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF<br>EEDKESTGTDEDSNTGSSAAAKVTEALIIEAEENCTA-Z (SEQ ID NO 136) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF<br>EEDKESTGTDEDSNTGSSAAAKVTEALIIEAEENCTAH-Z (SEQ ID NO 137) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF<br>EEDKESTGTDEDSNTGSSAAAKVTEALIIEAEENCTAHI-Z (SEQ ID NO 138) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF<br>EEDKESTGTDEDSNTGSSAAAKVTEALIIEAEENCTAHIT-Z (SEQ ID NO 139) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF<br>EEDKESTGTDEDSNTGSSAAAKVTEALIIEAEENCTAHITG-Z (SEQ ID NO 140) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF<br>EEDKESTGTDEDSNTGSSAAAKVTEALIIEAEENCTAHITGW-Z (SEQ ID NO 141) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF<br>EEDKESTGTDEDSNTGSSAAAKVTEALIIEAEENCTAHITGWT-Z (SEQ ID NO 142) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF<br>EEDKESTGTDEDSNTGSSAAAKVTEALIIEAEENCTAHITGWTT-Z (SEQ ID NO 143) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF<br>EEDKESTGTDEDSNTGSSAAAKVTEALIIEAEENCTAHITGWTTE-Z (SEQ ID NO 144) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF<br>EEDKESTGTDEDSNTGSSAAAKVTEALIIEAEENCTAHITGWTTET-Z (SEQ ID NO 145) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF<br>EEDKESTGTDEDSNTGSSAAAKVTEALIIEAEENCTAHITGWTTETP-Z (SEQ ID NO 146) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF<br>EEDKESTGTDEDSNTGSSAAAKVTEALIIEAEENCTAHITGWTTETPT-Z (SEQ ID NO 147) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF<br>EEDKESTGTDEDSNTGSSAAAKVTEALIIEAEENCTAHITGWTTETPTT-Z (SEQ ID NO 148) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF<br>EEDKESTGTDEDSNTGSSAAAKVTEALIIEAEENCTAHITGWTTETPTTL-Z (SEQ ID NO 149) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF<br>EEDKESTGTDEDSNTGSSAAAKVTEALIIEAEENCTAHITGWTTETPTTLE-Z (SEQ ID NO 150) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF<br>EEDKESTGTDEDSNTGSSAAAKVTEALIIEAEENCTAHITGWTTETPTTLEP-Z (SEQ ID NO 151) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF<br>EEDKESTGTDEDSNTGSSAAAKVTEALIIEAEENCTAHITGWTTETPTTLEPT-Z (SEQ ID NO 152) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF<br>EEDKESTGTDEDSNTGSSAAAKVTEALIIEAEENCTAHITGWTTETPTTLEPTT-Z (SEQ ID NO 153) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF<br>EEDKESTGTDEDSNTGSSAAAKVTEALIIEAEENCTAHITGWTTETPTTLEPTTE-Z (SEQ ID NO 154) |

TABLE I-continued

| Carboxy Truncations |
| --- |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDEDSNTGSSAAAKVTEALIIEAEENCTAHITGWTTETPTTLEPTTES-Z (SEQ ID NO 155) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDEDSNTGSSAAAKVTEALIIEAEENCTAHITGWTTETPTTLEPTTESQ-Z (SEQ ID NO 156) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDEDSNTGSSAAAKVTEALIIEAEENCTAHITGWTTETPTTLEPTTESQF-Z (SEQ ID NO 157) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDEDSNTGSSAAAKVTEALIIEAEENCTAHITGWTTETPTTLEPTTESQFE-Z (SEQ ID NO 158) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDEDSNTGSSAAAKVTEALIIEAEENCTAHITGWTTETPTTLEPTTESQFEA-Z (SEQ ID NO 159) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDEDSNTGSSAAAKVTEALIIEAEENCTAHITGWTTETPTTLEPTTESQFEAI-Z (SEQ ID NO 160) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDF EEDKESTGTDEDSNTGSSAAAKVTEALIIEAEENCTAHITGWTTETPTTLEPTTESQFEAIP-Z (SEQ ID NO 161) |

APPENDIX B

Table II

Table II shows Isac amino truncations.

In this table "X" may represent an amino group, a hydrophobic group, including but not limited to carbobenzoxyl, dansyl, or T-butyloxycarbonyl; an acetyl group; a 9-fluorenylmethoxy-carbonyl (FMOC); a macromolecular carrier group including but not limited to lipid-fatty acid conjugates, polyethylene glycol, or carbohydrates.

Additionally, in this table "Z" may represent a carboxyl group; an amino group; a T-butyloxycarbonyl group; a macromolecular carrier group including but not limited to lipid- fatty acid conjugates, polyethylene glycol, or carbohydrates.

TABLE II

| Amino Truncations |
| --- |
| X-AIP-Z (SEQ ID NO 162) |
| X-EAIP-Z (SEQ ID NO 163) |
| X-FEAIP-Z (SEQ ID NO 164) |
| X-QFEAIP-Z (SEQ ID NO 165) |
| X-SQFEAIP-Z (SEQ ID NO 166) |
| X-ESQFEAIP-Z (SEQ ID NO 167) |
| X-TESQFEAIP-Z (SEQ ID NO 168) |
| X-TTESQFEAIP-Z (SEQ ID NO 169) |
| X-PTTESQFEAIP-Z (SEQ ID NO 170) |
| X-EPTTESQFEAIP-Z (SEQ ID NO 171) |
| X-LEPTTESQFEAIP-Z (SEQ ID NO 172) |
| X-TLEPTTESQFEAIP-Z (SEQ ID NO 173) |
| X-TTLEPTTESQFEAIP-Z (SEQ ID NO 174) |
| X-PTTLEPTTESQFEAIP-Z (SEQ ID NO 175) |
| X-TPTTLEPTTESQFEAIP-Z (SEQ ID NO 176) |
| X-ETPTTLEPTTESQFEAIP-Z (SEQ ID NO 177) |
| X-TETPTTLEPTTESQFEAIP-Z (SEQ ID NO 178) |
| X-TTETPTTLEPTTESQFEAIP-Z (SEQ ID NO 179) |
| X-WTTETPTTLEPTTESQFEAIP-Z (SEQ ID NO 180) |

TABLE II-continued

| Amino Truncations |
|---|
| X-GWTTETPTTLEPTTESQFEAIP-Z (SEQ ID NO 181) |
| X-TGWTTETPTTLEPTTESQFEAIP-Z (SEQ ID NO 182) |
| X-ITGWTTETPTTLEPTTESQFEAIP-Z (SEQ ID NO 183) |
| X-HITGWTTETPTTLEPTTESQFEAIP-Z (SEQ ID NO 184) |
| X-AHITGWTTETPTTLEPTTESQFEAIP-Z (SEQ ID NO 185) |
| X-TAHITGWTTETPTTLEPTTESQFEAIP-Z (SEQ ID NO 186) |
| X-CTAHITGWTTETPTTLEPTTESQFEAIP-Z (SEQ ID NO 187) |
| X-NCTAHITGWTTETPTTLEPTTESQFEAIP-Z (SEQ ID NO 188) |
| X-ENCTAHITGWTTETPTTLEPTTESQFEAIP-Z (SEQ ID NO 189) |
| X-EENCTAHITGWTTETPTTLEPTTESQFEAIP-Z (SEQ ID NO 190) |
| X-AEENCTAHITGWTTETPTTLEPTTESQFEAIP-Z (SEQ ID NO 191) |
| X-EAEENCTAHITGWTTETPTTLEPTTESQFEAIP-Z (SEQ ID NO 192) |
| X-IEAEENCTAHITGWTTETPTTLEPTTESQFEAIP-Z (SEQ ID NO 193) |
| X-IIEAEENCTAHITGWTTETPTTLEPTTESQFEAIP-Z (SEQ ID NO 194) |
| X-LIIEAEENCTAHITGWTTETPTTLEPTTESQFEAIP-Z (SEQ ID NO 195) |
| X-ALIIEAEENCTAHITGWTTETPTTLEPTTESQFEAIP-Z (SEQ ID NO 196) |
| X-EALIIEAEENCTAHITGWTTETPTTLEPTTESQFEAIP-Z (SEQ ID NO 197) |
| X-TEALIIEAEENCTAHITGWTTETPTTLEPTTESQFEAIP-Z (SEQ ID NO 198) |
| X-VTEALIIEAEENCTAHITGWTTETPTTLEPTTESQFEAIP-Z (SEQ ID NO 199) |
| X-KVTEALIIEAEENCTAHITGWTTETPTTLEPTTESQFEAIP-Z (SEQ ID NO 200) |
| X-AKVTEALIIEAEENCTAHITGWTTETPTTLEPTTESQFEAIP-Z (SEQ ID NO 201) |
| X-AAKVTEALIIEAEENCTAHITGWTTETPTTLEPTTESQFEAIP-Z (SEQ ID NO 202) |
| X-AAAKVTEALIIEAEENCTAHITGWTTETPTTLEPTTESQFEAIP-Z (SEQ ID NO 203) |
| X-SAAAKVTEALIIEAEENCTAHITGWTTETPTTLEPTTESQFEAIP-Z (SEQ ID NO 204) |
| X-SSAAAKVTEALIIEAEENCTAHITGWTTETPTTLEPTTESQFEAIP-Z (SEQ ID NO 205) |
| X-GSSAAAKVTEALIIEAEENCTAHITGWTTETPTTLEPTTESQFEAIP-Z (SEQ ID NO 206) |
| X-TGSSAAAKVTEALIIEAEENCTAHITGWTTETPTTLEPTTESQFEAIP-Z (SEQ ID NO 207) |
| X-NTGSSAAAKVTEALIIEAEENCTAHITGWTTETPTTLEPTTESQFEAIP-Z (SEQ ID NO 208) |
| X-SNTGSSAAAKVTEALIIEAEENCTAHITGWTTETPTTLEPTTESQFEAIP-Z (SEQ ID NO 209) |
| X-DSNTGSSAAAKVTEALIIEAEENCTAHITGWTTETPTTLEPTTESQFEAIP-Z (SEQ ID NO 210) |
| X-EDSNTGSSAAAKVTEALIIEAEENCTAHITGWTTETPTTLEPTTESQFEAIP-Z (SEQ ID NO 211) |
| X-DEDSNTGSSAAAKVTEALIIEAEENCTAHITGWTTETPTTLEPTTESQFEAIP-Z (SEQ ID NO 212) |
| X-TDEDSNTGSSAAAKVTEALIIEAEENCTAHITGWTTETPTTLEPTTESQFEAIP-Z (SEQ ID NO 213) |
| X-GTDEDSNTGSSAAAKVTEALIIEAEENCTAHITGWTTETPTTLEPTTESQFEAIP-Z (SEQ ID NO 214) |
| X-TGTDEDSNTGSSAAAKVTEALIIEAEENCTAHITGWTTETPTTLEPTTESQFEAIP-Z (SEQ ID NO 215) |
| X-STGTDEDSNTGSSAAAKVTEALIIEAEENCTAHITGWTTETPTTLEPTTESQFEAIP-Z (SEQ ID NO 216) |
| X-ESTGTDEDSNTGSSAAAKVTEALIIEAEENCTAHITGWTTETPTTLEPTTESQFEAIP-Z (SEQ ID NO 217) |
| X-KESTGTDEDSNTGSSAAAKVTEALIIEAEENCTAHITGWTTETPTTLEPTTESQFEAIP-Z (SEQ ID NO 218) |

TABLE II-continued

| Amino Truncations |
| --- |
| X-DKESTGTDEDSNTGSSAAAKVTEALIIEAEENCTAHITGWTTETPTTLEPTTESQFEAIP-Z (SEQ ID NO 219) |
| X-EDKESTGTDEDSNTGSSAAAKVTEALIIEAEENCTAHITGWTTETPTTLEPTTESQFEAIP-Z (SEQ ID NO 220) |
| X-EEDKESTGTDEDSNTGSSAAAKVTEALIIEAEENCTAHITGWTTETPTTLEPTTESQFEAIP-Z (SEQ ID NO 221) |
| X-FEEDKESTGTDEDSNTGSSAAAKVTEALIIEAEENCTAHITGWTTETPTTLEPTTESQFEAIP-Z (SEQ ID NO 222) |
| X-DFEEDKESTGTDEDSNTGSSAAAKVTEALIIEAEENCTAHITGWTTETPTTLEPTTESQFEAIP-Z (SEQ ID NO 223) |
| X-SDFEEDKESTGTDEDSNTGSSAAAKVTEALIIEAEENCTAHITGWTTETPTTLEPTTESQFEAIP-Z (SEQ ID NO 224) |
| X-NSDFEEDKESTGTDEDSNTGSSAAAKVTEALIIEAEENCTAHITGWTTETPTTLEPTTESQFEAIP-Z (SEQ ID NO 225) |
| X-GNSDFEEDKESTGTDEDSNTGSSAAAKVTEALIIEAEENCTAHITGWTTETPTTLEPTTESQFEAIP-Z (SEQ ID NO 226) |
| X-DGNSDFEEDKESTGTDEDSNTGSSAAAKVTEALIIEAEENCTAHITGWTTETPTTLEPTTESQFEAIP-Z (SEQ ID NO 227) |
| X-SDGNSDFEEDKESTGTDEDSNTGSSAAAKVTEALIIEAEENCTAHITGWTTETPTTLEPTTESQFEAIP-Z (SEQ ID NO 228) |
| X-GSDGNSDFEEDKESTGTDEDSNTGSSAAAKVTEALIIEAEENCTAHITGWTTETPTTLEPTTESQFEAIP-Z (SEQ ID NO 229) |
| X-MGSDGNSDFEEDKESTGTDEDSNTGSSAAAKVTEALIIEAEENCTAHITGWTTETPTTLEPTTESQFEAIP-Z (SEQ ID NO 230) |
| X-YMGSDGNSDFEEDKESTGTDEDSNTGSSAAAKVTEALIIEAEENCTAHITGWTTETPTTLEPTTESQFEAIP-Z (SEQ ID NO 231) |
| X-VYMGSDGNSDFEEDKESTGTDEDSNTGSSAAAKVTEALIIEAEENCTAHITGWTTETPTTLEPTTESQFEAIP-Z (SEQ ID NO 232) |
| X-LVYMGSDGNSDFEEDKESTGTDEDSNTGSSAAAKVTEALIIEAEENCTAHITGWTTETPTTLEPTTESQFEAIP-Z (SEQ ID NO 233) |
| X-YLVYMGSDGNSDFEEDKESTGTDEDSNTGSSAAAKVTEALIIEAEENCTAHITGWTTETPTTLEPTTESQFEAIP-Z (SEQ ID NO 234) |
| X-FYLVYMGSDGNSDFEEDKESTGTDEDSNTGSSAAAKVTEALIIEAEENCTAHITGWTTETPTTLEPTTESQFEAIP-Z (SEQ ID NO 235) |
| X-EFYLVYMGSDGNSDFEEDKESTGTDEDSNTGSSAAAKVTEALIIEAEENCTAHITGWTTETPTTLEPTTESQFEAIP-Z (SEQ ID NO 236) |
| X-QEFYLVYMGSDGNSDFEEDKESTGTDEDSNTGSSAAAKVTEALIIEAEENCTAHITGWTTETPTTLEPTTESQFEAIP-Z (SEQ ID NO 237) |
| X-PQEFYLVYMGSDGNSDFEEDKESTGTDEDSNTGSSAAAKVTEALIIEAEENCTAHITGWTTETPTTLEPTTESQFEAIP-Z (SEQ ID NO 238) |
| X-MPQEFYLVYMGSDGNSDFEEDKESTGTDEDSNTGSSAAAKVTEALIIEAEENCTAHITGWTTETPTTLEPTTESQFEAIP-Z (SEQ ID NO 239) |
| X-AMPQEFYLVYMGSDGNSDFEEDKESTGTDEDSNTGSSAAAKVTEALIIEAEENCTAHITGWTTETPTTLEPTTESQFEAIP-Z (SEQ ID NO 240) |
| X-VAMPQEFYLVYMGSDGNSDFEEDKESTGTDEDSNTGSSAAAKVTEALIIEAEENCTAHITGWTTETPTTLEPTTESQFEAIP-Z (SEQ ID NO 241) |
| X-TVAMPQEFYLVYMGSDGNSDFEEDKESTGTDEDSNTGSSAAAKVTEALIIEAEENCTAHITGWTTETPTTLEPTTESQFEAIP-Z (SEQ ID NO 242) |
| X-FTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 243) |
| X-NFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 244) |
| X-CNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 245) |
| X-ICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 246) |
| X-LICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 247) |
| X-KLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 248) |
| X-VKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 249) |
| X-FVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 250) |
| X-QFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 251) |
| X-PQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 252) |

TABLE II-continued

| Amino Truncations |
|---|
| X-IPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 253) |
| X-TIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 254) |
| X-KTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 255) |
| X-NKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 256) |
| X-INKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 257) |
| X-RINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 258) |
| X-HRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 259) |
| X-RHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 260) |
| X-IRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 261) |
| X-GIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 262) |
| X-EGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 263) |
| X-WEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 264) |
| X-TWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 265) |
| X-ATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 266) |
| X-NATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 267) |
| X-VNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 268) |
| X-VVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 269) |
| X-PVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 270) |
| X-PPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 271) |
| X-LPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 272) |
| X-HLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 273) |
| X-NHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 274) |
| X-LNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 275) |
| X-TLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 276) |
| X-CTLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 277) |

TABLE II-continued

Amino Truncations

X-NCTLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 278)

X-YNCTLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 279)

X-VYNCTLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 280)

X-AVYNCTLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 281)

X-EAVYNCTLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 282)

X-AEAVYNCTLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 283)

X-HAEAVYNCTLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 284)

X-SHAEAVYNCTLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 285)

X-SSHAEAVYNCTLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 286)

X-NSSHAEAVYNCTLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 287)

X-RNSSHAEAVYNCTLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 288)

X-YRNSSHAEAVYNCTLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 289)

X-QYRNSSHAEAVYNCTLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 290)

X-AQYRNSSHAEAVYNCTLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 291)

X-GAQYRNSSHAEAVYNCTLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 292)

X-CGAQYRNSSHAEAVYNCTLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 293)

X-LCGAQYRNSSHAEAVYNCTLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 294)

X-GLCGAQYRNSSHAEAVYNCTLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 295)

X-SGLCGAQYRNSSHAEAVYNCTLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 296)

X-HSGLCGAQYRNSSHAEAVYNCTLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 297)

X-NHSGLCGAQYRNSSHAEAVYNCTLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 298)

X-RNHSGLCGAQYRNSSHAEAVYNCTLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 299)

X-YRNHSGLCGAQYRNSSHAEAVYNCTLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 300)

X-HYRNHSGLCGAQYRNSSHAEAVYNCTLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 301)

X-RHYRNHSGLCGAQYRNSSHAEAVYNCTLNHLPPVVNATWEGIRHRINKTIPQFVKLICNFTVAMPQEFYLVYMGSDGNSDFEEDKESTGTDEDSNTGSSAAAKVTEALIIEAEENCTAHITGWTTETPTTLEPTTESQFEAIP-Z (SEQ ID NO 302)

TABLE II-continued

| Amino Truncations |
|---|
| X-ERHYRNHSGLCGAQYRNSSHAEAVYNCTLNHLPPVVNATWEGIRHRINKTIPQFVKLICNFTVAMPQEFYLVYMGSDGNSDFEEDKESTGTDEDSNTGSSAA<br>AKVTEALIIEAEENCTAHITGWTTETPTTLEPTTESQFEAIP-Z (SEQ ID NO 303) |
| X-YERHYRNHSGLCGAQYRNSSHAEAVYNCTLNHLPPVVNATWEGIRHRINKTIPQFVKLICNFTVAMPQEFYLVYMGSDGNSDFEEDKESTGTDEDSNTGSSA<br>AAKVTEALIIEAEENCTAHITGWTTETPTTLEPTTESQFEAIP-Z (SEQ ID NO 304) |
| X-LYERHYRNHSGLCGAQYRNSSHAEAVYNCTLNHLPPVVNATWEGIRHRINKTIPQFVKLICNFTVAMPQEFYLVYMGSDGNSDFEEDKESTGTDEDSNTGSS<br>AAAKVTEALIIEAEENCTAHITGWTTETPTTLEPTTESQFEAIP-Z (SEQ ID NO 305) |
| X-NLYERHYRNHSGLCGAQYRNSSHAEAVYNCTLNHLPPVVNATWEGIRHRINKTIPQFVKLICNFTVAMPQEFYLVYMGSDGNSDFEEDKESTGTDEDSNTGS<br>SAAAKVTEALIIEAEENCTAHITGWTTETPTTLEPTTESQFEAIP-Z (SEQ ID NO 306) |
| X-QNLYERHYRNHSGLCGAQYRNSSHAEAVYNCTLNHLPPVVNATWEGIRHRINKTIPQFVKLICNFTVAMPQEFYLVYMGSDGNSDFEEDKESTGTDEDSNTG<br>SSAAAKVTEALIIEAEENCTAHITGWTTETPTTLEPTTESQFEAIP-Z (SEQ ID NO 307) |
| X-TQNLYERHYRNHSGLCGAQYRNSSHAEAVYNCTLNHLPPVVNATWEGIRHRINKTIPQFVKLICNFTVAMPQEFYLVYMGSDGNSDFEEDKESTGTDEDSNT<br>GSSAAAKVTEALIIEAEENCTAHITGWTTETPTTLEPTTESQFEAIP-Z (SEQ ID NO 308) |
| X-TTQNLYERHYRNHSGLCGAQYRNSSHAEAVYNCTLNHLPPVVNATWEGIRHRINKTIPQFVKLICNFTVAMPQEFYLVYMGSDGNSDFEEDKESTGTDEDSN<br>TGSSAAAKVTEALIIEAEENCTAHITGWTTETPTTLEPTTESQFEAIP-Z (SEQ ID NO 309) |
| X-TTTQNLYERHYRNHSGLCGAQYRNSSHAEAVYNCTLNHLPPVVNATWEGIRHRINKTIPQFVKLICNFTVAMPQEFYLVYMGSDGNSDFEEDKESTGTDEDS<br>NTGSSAAAKVTEALIIEAEENCTAHITGWTTETPTTLEPTTESQFEAIP-Z (SEQ ID NO 310) |
| X-ETTTQNLYERHYRNHSGLCGAQYRNSSHAEAVYNCTLNHLPPVVNATWEGIRHRINKTIPQFVKLICNFTVAMPQEFYLVYMGSDGNSDFEEDKESTGTDED<br>SNTGSSAAAKVTEALIIEAEENCTAHITGWTTETPTTLEPTTESQFEAIP-Z (SEQ ID NO 311) |
| X-VETTTQNLYERHYRNHSGLCGAQYRNSSHAEAVYNCTLNHLPPVVNATWEGIRHRINKTIPQFVKLICNFTVAMPQEFYLVYMGSDGNSDFEEDKESTGTDE<br>DSNTGSSAAAKVTEALIIEAEENCTAHITGWTTETPTTLEPTTESQFEAIP-Z (SEQ ID NO 312) |
| X-IVETTTQNLYERHYRNHSGLCGAQYRNSSHAEAVYNCTLNHLPPVVNATWEGIRHRINKTIPQFVKLICNFTVAMPQEFYLVYMGSDGNSDFEEDKESTGTD<br>EDSNTGSSAAAKVTEALIIEAEENCTAHITGWTTETPTTLEPTTESQFEAIP-Z (SEQ ID NO 313) |
| X-TIVETTTQNLYERHYRNHSGLCGAQYRNSSHAEAVYNCTLNHLPPVVNATWEGIRHRINKTIPQFVKLICNFTVAMPQEFYLVYMGSDGNSDFEEDKESTGT<br>DEDSNTGSSAAAKVTEALIIEAEENCTAHITGWTTETPTTLEPTTESQFEAIP-Z (SEQ ID NO 314) |
| X-DTIVETTTQNLYERHYRNHSGLCGAQYRNSSHAEAVYNCTLNHLPPVVNATWEGIRHRINKTIPQFVKLICNFTVAMPQEFYLVYMGSDGNSDFEEDKESTG<br>TDEDSNTGSSAAAKVTEALIIEAEENCTAHITGWTTETPTTLEPTTESQFEAIP-Z (SEQ ID NO 315) |
| X-QDTIVETTTQNLYERHYRNHSGLCGAQYRNSSHAEAVYNCTLNHLPPVVNATWEGIRHRINKTIPQFVKLICNFTVAMPQEFYLVYMGSDGNSDFEEDKEST<br>GTDEDSNTGSSAAAKVTEALIIEAEENCTAHITGWTTETPTTLEPTTESQFEAIP-Z (SEQ ID NO 316) |
| X-EQDTIVETTTQNLYERHYRNHSGLCGAQYRNSSHAEAVYNCTLNHLPPVVNATWEGIRHRINKTIPQFVKLICNFTVAMPQEFYLVYMGSDGNSDFEEDKES<br>TGTDEDSNTGSSAAAKVTEALIIEAEENCTAHITGWTTETPTTLEPTTESQFEAIP-Z (SEQ ID NO 317) |
| X-LEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDFEEDKE<br>STGTDEDSNTGSSAAAKVTEALIIEAEENCTAHITGWTTETPTTLEPTTESQFEAIP-Z (SEQ ID NO 318) |
| X-GLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDFEEDK<br>ESTGTDEDSNTGSSAAAKVTEALIIEAEENCTAHITGWTTETPTTLEPTTESQFEAIP-Z (SEQ ID NO 319) |
| X-DGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDFEED<br>KESTGTDEDSNTGSSAAAKVTEALIIEAEENCTAHITGWTTETPTTLEPTTESQFEAIP-Z (SEQ ID NO 320) |
| X-EDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDFEE<br>DKESTGTDEDSNTGSSAAAKVTEALIIEAEENCTAHITGWTTETPTTLEPTTESQFEAIP-Z (SEQ ID NO 321) |
| X-SEDGLEQDTIVETTTQNLYERHYRNHSGLCGAQYRNSSHAEAVYNCTLNHLPPVVNATWEGIRHRINKTIPQFVKLICNFTVAMPQEFYLVYMGSDGNSDFEE<br>DKESTGTDEDSNTGSSAAAKVTEALIIEAEENCTAHITGWTTETPTTLEPTTESQFEAIP-Z (SEQ ID NO 161) |

What is claimed is:

1. A purified composition comprising a DNA, or its complement, said DNA encoding an Ixodes scapularis salivary anticomplement (Isac) gene product comprising SEQ ID NO: 161.

2. A purified composition comprising a cDNA, or its complement, said cDNA encoding an Isac gene product comprising SEQ ID NO: 161.

3. A purified composition comprising a DNA, or its complement, said DNA encoding an Isac gene product having anticomplement activity and said DNA hybridizing to the cDNA sequence encoding the Isac gene product of SEQ ID NO: 161 under high stringency conditions defined as hybridization to filter-bound DNA in 0.5 M $NaHPO_4$, 7% sodium dodecyl sulfate (SDS), 1 mM EDTA at 65° C., and washing in 0.1 times SSC/0.1% SDS at 68° C.

4. A vector comprising the purified composition of any of claims 1 to 3.

5. A host cell comprising the vector of claim 4.

6. A method of making an Isac peptide, polypeptide or protein having anticomplement activity and encoded by a DNA hybridizable to the cDNA sequence encoding the Isac gene product of SEQ ID NO: 161 comprising the steps of:

obtaining the DNA of any of claims 1–3;

inserting said DNA in an expression vector such that said DNA is operably linked to a promoter; and introducing said expression vector into a host cell whereby said host cell produces the peptide, polypeptide or protein encoded by said DNA.

7. In an array of DNA immobilized on a substrate, the improvement comprising the inclusion in said array of the DNA of any of claims 1–3 or its complement.

* * * * *

SEQUENCE LISTING

<160> NUMBER OF SEQ ID NOS: 404

<210> SEQ ID NO 1
<211> LENGTH: 3
<212> TYPE: PRT
<213> ORGANISM: Ixodes scapularis

<400> SEQUENCE: 1

-continued

```
Ser Glu Asp
 1


<210> SEQ ID NO 2
<211> LENGTH: 4
<212> TYPE: PRT
<213> ORGANISM: Ixodes scapularis

<400> SEQUENCE: 2

Ser Glu Asp Gly
 1


<210> SEQ ID NO 3
<211> LENGTH: 5
<212> TYPE: PRT
<213> ORGANISM: Ixodes scapularis

<400> SEQUENCE: 3

Ser Glu Asp Gly Leu
 1               5


<210> SEQ ID NO 4
<211> LENGTH: 6
<212> TYPE: PRT
<213> ORGANISM: Ixodes scapularis

<400> SEQUENCE: 4

Ser Glu Asp Gly Leu Glu
 1               5


<210> SEQ ID NO 5
<211> LENGTH: 7
<212> TYPE: PRT
<213> ORGANISM: Ixodes scapularis

<400> SEQUENCE: 5

Ser Glu Asp Gly Leu Glu Gln
 1               5


<210> SEQ ID NO 6
<211> LENGTH: 8
<212> TYPE: PRT
<213> ORGANISM: Ixodes scapularis

<400> SEQUENCE: 6

Ser Glu Asp Gly Leu Glu Gln Asp
 1               5


<210> SEQ ID NO 7
<211> LENGTH: 9
<212> TYPE: PRT
<213> ORGANISM: Ixodes scapularis

<400> SEQUENCE: 7

Ser Glu Asp Gly Leu Glu Gln Asp Thr
 1               5


<210> SEQ ID NO 8
<211> LENGTH: 10
<212> TYPE: PRT
<213> ORGANISM: Ixodes scapularis

<400> SEQUENCE: 8

Ser Glu Asp Gly Leu Glu Gln Asp Thr Ile
```

-continued

```
 1               5                   10


<210> SEQ ID NO 9
<211> LENGTH: 11
<212> TYPE: PRT
<213> ORGANISM: Ixodes scapularis

<400> SEQUENCE: 9

Ser Glu Asp Gly Leu Glu Gln Asp Thr Ile Val
 1               5                   10


<210> SEQ ID NO 10
<211> LENGTH: 12
<212> TYPE: PRT
<213> ORGANISM: Ixodes scapularis

<400> SEQUENCE: 10

Ser Glu Asp Gly Leu Glu Gln Asp Thr Ile Val Glu
 1               5                   10


<210> SEQ ID NO 11
<211> LENGTH: 13
<212> TYPE: PRT
<213> ORGANISM: Ixodes scapularis

<400> SEQUENCE: 11

Ser Glu Asp Gly Leu Glu Gln Asp Thr Ile Val Glu Thr
 1               5                   10


<210> SEQ ID NO 12
<211> LENGTH: 14
<212> TYPE: PRT
<213> ORGANISM: Ixodes scapularis

<400> SEQUENCE: 12

Ser Glu Asp Gly Leu Glu Gln Asp Thr Ile Val Glu Thr Thr
 1               5                   10


<210> SEQ ID NO 13
<211> LENGTH: 15
<212> TYPE: PRT
<213> ORGANISM: Ixodes scapularis

<400> SEQUENCE: 13

Ser Glu Asp Gly Leu Glu Gln Asp Thr Ile Val Glu Thr Thr Thr
 1               5                   10                  15


<210> SEQ ID NO 14
<211> LENGTH: 16
<212> TYPE: PRT
<213> ORGANISM: Ixodes scapularis

<400> SEQUENCE: 14

Ser Glu Asp Gly Leu Glu Gln Asp Thr Ile Val Glu Thr Thr Thr Gln
 1               5                   10                  15


<210> SEQ ID NO 15
<211> LENGTH: 17
<212> TYPE: PRT
<213> ORGANISM: Ixodes scapularis

<400> SEQUENCE: 15

Ser Glu Asp Gly Leu Glu Gln Asp Thr Ile Val Glu Thr Thr Thr Gln
 1               5                   10                  15
```

-continued

Asn

<210> SEQ ID NO 16
<211> LENGTH: 18
<212> TYPE: PRT
<213> ORGANISM: Ixodes scapularis

<400> SEQUENCE: 16

Ser Glu Asp Gly Leu Glu Gln Asp Thr Ile Val Glu Thr Thr Thr Gln
1 5 10 15

Asn Leu

<210> SEQ ID NO 17
<211> LENGTH: 19
<212> TYPE: PRT
<213> ORGANISM: Ixodes scapularis

<400> SEQUENCE: 17

Ser Glu Asp Gly Leu Glu Gln Asp Thr Ile Val Glu Thr Thr Thr Gln
1 5 10 15

Asn Leu Tyr

<210> SEQ ID NO 18
<211> LENGTH: 20
<212> TYPE: PRT
<213> ORGANISM: Ixodes scapularis

<400> SEQUENCE: 18

Ser Glu Asp Gly Leu Glu Gln Asp Thr Ile Val Glu Thr Thr Thr Gln
1 5 10 15

Asn Leu Tyr Glu
20

<210> SEQ ID NO 19
<211> LENGTH: 21
<212> TYPE: PRT
<213> ORGANISM: Ixodes scapularis

<400> SEQUENCE: 19

Ser Glu Asp Gly Leu Glu Gln Asp Thr Ile Val Glu Thr Thr Thr Gln
1 5 10 15

Asn Leu Tyr Glu Arg
20

<210> SEQ ID NO 20
<211> LENGTH: 22
<212> TYPE: PRT
<213> ORGANISM: Ixodes scapularis

<400> SEQUENCE: 20

Ser Glu Asp Gly Leu Glu Gln Asp Thr Ile Val Glu Thr Thr Thr Gln
1 5 10 15

Asn Leu Tyr Glu Arg His
20

<210> SEQ ID NO 21
<211> LENGTH: 23
<212> TYPE: PRT
<213> ORGANISM: Ixodes scapularis

<400> SEQUENCE: 21

Ser Glu Asp Gly Leu Glu Gln Asp Thr Ile Val Glu Thr Thr Thr Gln

-continued

```
 1               5                  10                  15

Asn Leu Tyr Glu Arg His Tyr
            20


<210> SEQ ID NO 22
<211> LENGTH: 24
<212> TYPE: PRT
<213> ORGANISM: Ixodes scapularis

<400> SEQUENCE: 22

Ser Glu Asp Gly Leu Glu Gln Asp Thr Ile Val Glu Thr Thr Thr Gln
 1               5                  10                  15

Asn Leu Tyr Glu Arg His Tyr Arg
            20


<210> SEQ ID NO 23
<211> LENGTH: 25
<212> TYPE: PRT
<213> ORGANISM: Ixodes scapularis

<400> SEQUENCE: 23

Ser Glu Asp Gly Leu Glu Gln Asp Thr Ile Val Glu Thr Thr Thr Gln
 1               5                  10                  15

Asn Leu Tyr Glu Arg His Tyr Arg Asn
            20                  25


<210> SEQ ID NO 24
<211> LENGTH: 26
<212> TYPE: PRT
<213> ORGANISM: Ixodes scapularis

<400> SEQUENCE: 24

Ser Glu Asp Gly Leu Glu Gln Asp Thr Ile Val Glu Thr Thr Thr Gln
 1               5                  10                  15

Asn Leu Tyr Glu Arg His Tyr Arg Asn His
            20                  25


<210> SEQ ID NO 25
<211> LENGTH: 27
<212> TYPE: PRT
<213> ORGANISM: Ixodes scapularis

<400> SEQUENCE: 25

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser
            20                  25


<210> SEQ ID NO 26
<211> LENGTH: 28
<212> TYPE: PRT
<213> ORGANISM: Ixodes scapularis

<400> SEQUENCE: 26

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly
            20                  25


<210> SEQ ID NO 27
<211> LENGTH: 29
<212> TYPE: PRT
```

-continued

<213> ORGANISM: Ixodes scapularis

<400> SEQUENCE: 27

Ser Glu Asp Gly Leu Glu Gln Asp Thr Ile Val Glu Thr Thr Thr Gln
1 5 10 15

Asn Leu Tyr Glu Arg His Tyr Arg Asn His Ser Gly Leu
20 25

<210> SEQ ID NO 28
<211> LENGTH: 30
<212> TYPE: PRT
<213> ORGANISM: Ixodes scapularis

<400> SEQUENCE: 28

Ser Glu Asp Gly Leu Glu Gln Asp Thr Ile Val Glu Thr Thr Thr Gln
1 5 10 15

Asn Leu Tyr Glu Arg His Tyr Arg Asn His Ser Gly Leu Cys
20 25 30

<210> SEQ ID NO 29
<211> LENGTH: 31
<212> TYPE: PRT
<213> ORGANISM: Ixodes scapularis

<400> SEQUENCE: 29

Ser Glu Asp Gly Leu Glu Gln Asp Thr Ile Val Glu Thr Thr Thr Gln
1 5 10 15

Asn Leu Tyr Glu Arg His Tyr Arg Asn His Ser Gly Leu Cys Gly
20 25 30

<210> SEQ ID NO 30
<211> LENGTH: 32
<212> TYPE: PRT
<213> ORGANISM: Ixodes scapularis

<400> SEQUENCE: 30

Ser Glu Asp Gly Leu Glu Gln Asp Thr Ile Val Glu Thr Thr Thr Gln
1 5 10 15

Asn Leu Tyr Glu Arg His Tyr Arg Asn His Ser Gly Leu Cys Gly Ala
20 25 30

<210> SEQ ID NO 31
<211> LENGTH: 33
<212> TYPE: PRT
<213> ORGANISM: Ixodes scapularis

<400> SEQUENCE: 31

Ser Glu Asp Gly Leu Glu Gln Asp Thr Ile Val Glu Thr Thr Thr Gln
1 5 10 15

Asn Leu Tyr Glu Arg His Tyr Arg Asn His Ser Gly Leu Cys Gly Ala
20 25 30

Gln

<210> SEQ ID NO 32
<211> LENGTH: 34
<212> TYPE: PRT
<213> ORGANISM: Ixodes scapularis

<400> SEQUENCE: 32

Ser Glu Asp Gly Leu Glu Gln Asp Thr Ile Val Glu Thr Thr Thr Gln
1 5 10 15

-continued

```
Asn Leu Tyr Glu Arg His Tyr Arg Asn His Ser Gly Leu Cys Gly Ala
            20                  25                  30

Gln Tyr


<210> SEQ ID NO 33
<211> LENGTH: 35
<212> TYPE: PRT
<213> ORGANISM: Ixodes scapularis

<400> SEQUENCE: 33

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg
        35


<210> SEQ ID NO 34
<211> LENGTH: 36
<212> TYPE: PRT
<213> ORGANISM: Ixodes scapularis

<400> SEQUENCE: 34

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn
        35


<210> SEQ ID NO 35
<211> LENGTH: 37
<212> TYPE: PRT
<213> ORGANISM: Ixodes scapularis

<400> SEQUENCE: 35

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser
        35


<210> SEQ ID NO 36
<211> LENGTH: 38
<212> TYPE: PRT
<213> ORGANISM: Ixodes scapularis

<400> SEQUENCE: 36

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser
        35


<210> SEQ ID NO 37
<211> LENGTH: 39
<212> TYPE: PRT
<213> ORGANISM: Ixodes scapularis
```

-continued

<400> SEQUENCE: 37

Ser Glu Asp Gly Leu Glu Gln Asp Thr Ile Val Glu Thr Thr Thr Gln
1 5 10 15

Asn Leu Tyr Glu Arg His Tyr Arg Asn His Ser Gly Leu Cys Gly Ala
20 25 30

Gln Tyr Arg Asn Ser Ser His
35

<210> SEQ ID NO 38
<211> LENGTH: 40
<212> TYPE: PRT
<213> ORGANISM: Ixodes scapularis

<400> SEQUENCE: 38

Ser Glu Asp Gly Leu Glu Gln Asp Thr Ile Val Glu Thr Thr Thr Gln
1 5 10 15

Asn Leu Tyr Glu Arg His Tyr Arg Asn His Ser Gly Leu Cys Gly Ala
20 25 30

Gln Tyr Arg Asn Ser Ser His Ala
35 40

<210> SEQ ID NO 39
<211> LENGTH: 41
<212> TYPE: PRT
<213> ORGANISM: Ixodes scapularis

<400> SEQUENCE: 39

Ser Glu Asp Gly Leu Glu Gln Asp Thr Ile Val Glu Thr Thr Thr Gln
1 5 10 15

Asn Leu Tyr Glu Arg His Tyr Arg Asn His Ser Gly Leu Cys Gly Ala
20 25 30

Gln Tyr Arg Asn Ser Ser His Ala Glu
35 40

<210> SEQ ID NO 40
<211> LENGTH: 42
<212> TYPE: PRT
<213> ORGANISM: Ixodes scapularis

<400> SEQUENCE: 40

Ser Glu Asp Gly Leu Glu Gln Asp Thr Ile Val Glu Thr Thr Thr Gln
1 5 10 15

Asn Leu Tyr Glu Arg His Tyr Arg Asn His Ser Gly Leu Cys Gly Ala
20 25 30

Gln Tyr Arg Asn Ser Ser His Ala Glu Ala
35 40

<210> SEQ ID NO 41
<211> LENGTH: 43
<212> TYPE: PRT
<213> ORGANISM: Ixodes scapularis

<400> SEQUENCE: 41

Ser Glu Asp Gly Leu Glu Gln Asp Thr Ile Val Glu Thr Thr Thr Gln
1 5 10 15

Asn Leu Tyr Glu Arg His Tyr Arg Asn His Ser Gly Leu Cys Gly Ala
20 25 30

Gln Tyr Arg Asn Ser Ser His Ala Glu Ala Val
35 40

-continued

<210> SEQ ID NO 42
<211> LENGTH: 44
<212> TYPE: PRT
<213> ORGANISM: Ixodes scapularis

<400> SEQUENCE: 42

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr
        35                  40
```

<210> SEQ ID NO 43
<211> LENGTH: 45
<212> TYPE: PRT
<213> ORGANISM: Ixodes scapularis

<400> SEQUENCE: 43

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn
        35                  40                  45
```

<210> SEQ ID NO 44
<211> LENGTH: 46
<212> TYPE: PRT
<213> ORGANISM: Ixodes scapularis

<400> SEQUENCE: 44

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys
        35                  40                  45
```

<210> SEQ ID NO 45
<211> LENGTH: 47
<212> TYPE: PRT
<213> ORGANISM: Ixodes scapularis

<400> SEQUENCE: 45

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr
        35                  40                  45
```

<210> SEQ ID NO 46
<211> LENGTH: 48
<212> TYPE: PRT
<213> ORGANISM: Ixodes scapularis

<400> SEQUENCE: 46

```
Ser Glu Asp Gly Leu Glu Gln Asp Thr Ile Val Glu Thr Thr Thr Gln
 1               5                  10                  15
```

-continued

```
Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45


<210> SEQ ID NO 47
<211> LENGTH: 49
<212> TYPE: PRT
<213> ORGANISM: Ixodes scapularis

<400> SEQUENCE: 47

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn


<210> SEQ ID NO 48
<211> LENGTH: 50
<212> TYPE: PRT
<213> ORGANISM: Ixodes scapularis

<400> SEQUENCE: 48

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His
    50


<210> SEQ ID NO 49
<211> LENGTH: 51
<212> TYPE: PRT
<213> ORGANISM: Ixodes scapularis

<400> SEQUENCE: 49

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu
    50


<210> SEQ ID NO 50
<211> LENGTH: 52
<212> TYPE: PRT
<213> ORGANISM: Ixodes scapularis

<400> SEQUENCE: 50

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30
```

-continued

```
Gln Tyr Arg Asn Ser Ser His Ala Glu Ala Val Tyr Asn Cys Thr Leu
        35                  40                  45

Asn His Leu Pro
    50


<210> SEQ ID NO 51
<211> LENGTH: 53
<212> TYPE: PRT
<213> ORGANISM: Ixodes scapularis

<400> SEQUENCE: 51

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro
    50


<210> SEQ ID NO 52
<211> LENGTH: 54
<212> TYPE: PRT
<213> ORGANISM: Ixodes scapularis

<400> SEQUENCE: 52

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val
    50


<210> SEQ ID NO 53
<211> LENGTH: 55
<212> TYPE: PRT
<213> ORGANISM: Ixodes scapularis

<400> SEQUENCE: 53

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val
    50                  55


<210> SEQ ID NO 54
<211> LENGTH: 56
<212> TYPE: PRT
<213> ORGANISM: Ixodes scapularis

<400> SEQUENCE: 54

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30
```

-continued

```
Gln Tyr Arg Asn Ser Ser His Ala Glu Ala Val Tyr Asn Cys Thr Leu
        35                  40                  45

Asn His Leu Pro Pro Val Val Asn
    50                  55


<210> SEQ ID NO 55
<211> LENGTH: 57
<212> TYPE: PRT
<213> ORGANISM: Ixodes scapularis

<400> SEQUENCE: 55

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala
    50                  55


<210> SEQ ID NO 56
<211> LENGTH: 58
<212> TYPE: PRT
<213> ORGANISM: Ixodes scapularis

<400> SEQUENCE: 56

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr
    50                  55


<210> SEQ ID NO 57
<211> LENGTH: 59
<212> TYPE: PRT
<213> ORGANISM: Ixodes scapularis

<400> SEQUENCE: 57

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp
    50                  55


<210> SEQ ID NO 58
<211> LENGTH: 60
<212> TYPE: PRT
<213> ORGANISM: Ixodes scapularis

<400> SEQUENCE: 58

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
```

-continued

```
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu
    50                  55                  60


<210> SEQ ID NO 59
<211> LENGTH: 61
<212> TYPE: PRT
<213> ORGANISM: Ixodes scapularis

<400> SEQUENCE: 59

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly
    50                  55                  60


<210> SEQ ID NO 60
<211> LENGTH: 62
<212> TYPE: PRT
<213> ORGANISM: Ixodes scapularis

<400> SEQUENCE: 60

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile
    50                  55                  60


<210> SEQ ID NO 61
<211> LENGTH: 63
<212> TYPE: PRT
<213> ORGANISM: Ixodes scapularis

<400> SEQUENCE: 61

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg
    50                  55                  60


<210> SEQ ID NO 62
<211> LENGTH: 64
<212> TYPE: PRT
<213> ORGANISM: Ixodes scapularis

<400> SEQUENCE: 62

Ser Glu Asp Gly Leu Glu Gln Asp Thr Ile Val Glu Thr Thr Thr Gln
 1               5                  10                  15
```

-continued

```
Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60


<210> SEQ ID NO 63
<211> LENGTH: 65
<212> TYPE: PRT
<213> ORGANISM: Ixodes scapularis

<400> SEQUENCE: 63

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg
65


<210> SEQ ID NO 64
<211> LENGTH: 66
<212> TYPE: PRT
<213> ORGANISM: Ixodes scapularis

<400> SEQUENCE: 64

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile
65


<210> SEQ ID NO 65
<211> LENGTH: 67
<212> TYPE: PRT
<213> ORGANISM: Ixodes scapularis

<400> SEQUENCE: 65

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn
65
```

-continued

```
<210> SEQ ID NO 66
<211> LENGTH: 68
<212> TYPE: PRT
<213> ORGANISM: Ixodes scapularis

<400> SEQUENCE: 66

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys
65


<210> SEQ ID NO 67
<211> LENGTH: 69
<212> TYPE: PRT
<213> ORGANISM: Ixodes scapularis

<400> SEQUENCE: 67

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr
65


<210> SEQ ID NO 68
<211> LENGTH: 70
<212> TYPE: PRT
<213> ORGANISM: Ixodes scapularis

<400> SEQUENCE: 68

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile
65                  70


<210> SEQ ID NO 69
<211> LENGTH: 71
<212> TYPE: PRT
<213> ORGANISM: Ixodes scapularis

<400> SEQUENCE: 69

Ser Glu Asp Gly Leu Glu Gln Asp Thr Ile Val Glu Thr Thr Thr Gln
 1               5                  10                  15
```

-continued

```
Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro
65                  70


<210> SEQ ID NO 70
<211> LENGTH: 72
<212> TYPE: PRT
<213> ORGANISM: Ixodes scapularis

<400> SEQUENCE: 70

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln
65                  70


<210> SEQ ID NO 71
<211> LENGTH: 73
<212> TYPE: PRT
<213> ORGANISM: Ixodes scapularis

<400> SEQUENCE: 71

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe
65                  70


<210> SEQ ID NO 72
<211> LENGTH: 74
<212> TYPE: PRT
<213> ORGANISM: Ixodes scapularis

<400> SEQUENCE: 72

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val
```

-continued 65 70

<210> SEQ ID NO 73
<211> LENGTH: 75
<212> TYPE: PRT
<213> ORGANISM: Ixodes scapularis

<400> SEQUENCE: 73

Ser Glu Asp Gly Leu Glu Gln Asp Thr Ile Val Glu Thr Thr Thr Gln
1 5 10 15

Asn Leu Tyr Glu Arg His Tyr Arg Asn His Ser Gly Leu Cys Gly Ala
20 25 30

Gln Tyr Arg Asn Ser Ser His Ala Glu Ala Val Tyr Asn Cys Thr Leu
35 40 45

Asn His Leu Pro Pro Val Val Asn Ala Thr Trp Glu Gly Ile Arg His
50 55 60

Arg Ile Asn Lys Thr Ile Pro Gln Phe Val Lys
65 70 75

<210> SEQ ID NO 74
<211> LENGTH: 76
<212> TYPE: PRT
<213> ORGANISM: Ixodes scapularis

<400> SEQUENCE: 74

Ser Glu Asp Gly Leu Glu Gln Asp Thr Ile Val Glu Thr Thr Thr Gln
1 5 10 15

Asn Leu Tyr Glu Arg His Tyr Arg Asn His Ser Gly Leu Cys Gly Ala
20 25 30

Gln Tyr Arg Asn Ser Ser His Ala Glu Ala Val Tyr Asn Cys Thr Leu
35 40 45

Asn His Leu Pro Pro Val Val Asn Ala Thr Trp Glu Gly Ile Arg His
50 55 60

Arg Ile Asn Lys Thr Ile Pro Gln Phe Val Lys Leu
65 70 75

<210> SEQ ID NO 75
<211> LENGTH: 77
<212> TYPE: PRT
<213> ORGANISM: Ixodes scapularis

<400> SEQUENCE: 75

Ser Glu Asp Gly Leu Glu Gln Asp Thr Ile Val Glu Thr Thr Thr Gln
1 5 10 15

Asn Leu Tyr Glu Arg His Tyr Arg Asn His Ser Gly Leu Cys Gly Ala
20 25 30

Gln Tyr Arg Asn Ser Ser His Ala Glu Ala Val Tyr Asn Cys Thr Leu
35 40 45

Asn His Leu Pro Pro Val Val Asn Ala Thr Trp Glu Gly Ile Arg His
50 55 60

Arg Ile Asn Lys Thr Ile Pro Gln Phe Val Lys Leu Ile
65 70 75

<210> SEQ ID NO 76
<211> LENGTH: 78
<212> TYPE: PRT
<213> ORGANISM: Ixodes scapularis

<400> SEQUENCE: 76

-continued

```
Ser Glu Asp Gly Leu Glu Gln Asp Thr Ile Val Glu Thr Thr Thr Gln
1               5                   10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys
65                  70                  75


<210> SEQ ID NO 77
<211> LENGTH: 79
<212> TYPE: PRT
<213> ORGANISM: Ixodes scapularis

<400> SEQUENCE: 77

Ser Glu Asp Gly Leu Glu Gln Asp Thr Ile Val Glu Thr Thr Thr Gln
1               5                   10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn
65                  70                  75


<210> SEQ ID NO 78
<211> LENGTH: 80
<212> TYPE: PRT
<213> ORGANISM: Ixodes scapularis

<400> SEQUENCE: 78

Ser Glu Asp Gly Leu Glu Gln Asp Thr Ile Val Glu Thr Thr Thr Gln
1               5                   10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80


<210> SEQ ID NO 79
<211> LENGTH: 81
<212> TYPE: PRT
<213> ORGANISM: Ixodes scapularis

<400> SEQUENCE: 79

Ser Glu Asp Gly Leu Glu Gln Asp Thr Ile Val Glu Thr Thr Thr Gln
1               5                   10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
```

-continued

```
    50                  55                  60

Arg Ile Asn Lys Thr Ile Pro Gln Phe Val Lys Leu Ile Cys Asn Phe
65                  70                  75                  80

Thr


<210> SEQ ID NO 80
<211> LENGTH: 82
<212> TYPE: PRT
<213> ORGANISM: Ixodes scapularis

<400> SEQUENCE: 80

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val


<210> SEQ ID NO 81
<211> LENGTH: 83
<212> TYPE: PRT
<213> ORGANISM: Ixodes scapularis

<400> SEQUENCE: 81

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala


<210> SEQ ID NO 82
<211> LENGTH: 84
<212> TYPE: PRT
<213> ORGANISM: Ixodes scapularis

<400> SEQUENCE: 82

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80
```

-continued

```
Thr Val Ala Met

<210> SEQ ID NO 83
<211> LENGTH: 85
<212> TYPE: PRT
<213> ORGANISM: Ixodes scapularis

<400> SEQUENCE: 83

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro
                85


<210> SEQ ID NO 84
<211> LENGTH: 86
<212> TYPE: PRT
<213> ORGANISM: Ixodes scapularis

<400> SEQUENCE: 84

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln
                85


<210> SEQ ID NO 85
<211> LENGTH: 87
<212> TYPE: PRT
<213> ORGANISM: Ixodes scapularis

<400> SEQUENCE: 85

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu
```

-continued

```
                85

<210> SEQ ID NO 86
<211> LENGTH: 88
<212> TYPE: PRT
<213> ORGANISM: Ixodes scapularis

<400> SEQUENCE: 86

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
             20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe
                85

<210> SEQ ID NO 87
<211> LENGTH: 89
<212> TYPE: PRT
<213> ORGANISM: Ixodes scapularis

<400> SEQUENCE: 87

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
             20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr
                85

<210> SEQ ID NO 88
<211> LENGTH: 90
<212> TYPE: PRT
<213> ORGANISM: Ixodes scapularis

<400> SEQUENCE: 88

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
             20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu
                85                  90
```

<210> SEQ ID NO 89
<211> LENGTH: 91
<212> TYPE: PRT
<213> ORGANISM: Ixodes scapularis

<400> SEQUENCE: 89

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val
                85                  90
```

<210> SEQ ID NO 90
<211> LENGTH: 92
<212> TYPE: PRT
<213> ORGANISM: Ixodes scapularis

<400> SEQUENCE: 90

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr
                85                  90
```

<210> SEQ ID NO 91
<211> LENGTH: 93
<212> TYPE: PRT
<213> ORGANISM: Ixodes scapularis

<400> SEQUENCE: 91

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met
                85                  90
```

-continued

<210> SEQ ID NO 92
<211> LENGTH: 94
<212> TYPE: PRT
<213> ORGANISM: Ixodes scapularis

<400> SEQUENCE: 92

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly
                85                  90
```

<210> SEQ ID NO 93
<211> LENGTH: 95
<212> TYPE: PRT
<213> ORGANISM: Ixodes scapularis

<400> SEQUENCE: 93

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser
                85                  90                  95
```

<210> SEQ ID NO 94
<211> LENGTH: 96
<212> TYPE: PRT
<213> ORGANISM: Ixodes scapularis

<400> SEQUENCE: 94

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95
```

-continued

<210> SEQ ID NO 95
<211> LENGTH: 97
<212> TYPE: PRT
<213> ORGANISM: Ixodes scapularis

<400> SEQUENCE: 95

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95
Gly
```

<210> SEQ ID NO 96
<211> LENGTH: 98
<212> TYPE: PRT
<213> ORGANISM: Ixodes scapularis

<400> SEQUENCE: 96

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn
```

<210> SEQ ID NO 97
<211> LENGTH: 99
<212> TYPE: PRT
<213> ORGANISM: Ixodes scapularis

<400> SEQUENCE: 97

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95
```

-continued

Gly Asn Ser

<210> SEQ ID NO 98
<211> LENGTH: 100
<212> TYPE: PRT
<213> ORGANISM: Ixodes scapularis

<400> SEQUENCE: 98

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp
            100
```

<210> SEQ ID NO 99
<211> LENGTH: 101
<212> TYPE: PRT
<213> ORGANISM: Ixodes scapularis

<400> SEQUENCE: 99

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe
            100
```

<210> SEQ ID NO 100
<211> LENGTH: 102
<212> TYPE: PRT
<213> ORGANISM: Ixodes scapularis

<400> SEQUENCE: 100

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
```

-continued

```
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu
            100


<210> SEQ ID NO 101
<211> LENGTH: 103
<212> TYPE: PRT
<213> ORGANISM: Ixodes scapularis

<400> SEQUENCE: 101

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu
            100


<210> SEQ ID NO 102
<211> LENGTH: 104
<212> TYPE: PRT
<213> ORGANISM: Ixodes scapularis

<400> SEQUENCE: 102

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp
            100


<210> SEQ ID NO 103
<211> LENGTH: 105
<212> TYPE: PRT
<213> ORGANISM: Ixodes scapularis

<400> SEQUENCE: 103

Ser Glu Asp Gly Leu Glu Gln Asp Thr Ile Val Glu Thr Thr Thr Gln
 1               5                  10                  15
```

-continued

```
Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys
            100                 105


<210> SEQ ID NO 104
<211> LENGTH: 106
<212> TYPE: PRT
<213> ORGANISM: Ixodes scapularis

<400> SEQUENCE: 104

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu
            100                 105


<210> SEQ ID NO 105
<211> LENGTH: 107
<212> TYPE: PRT
<213> ORGANISM: Ixodes scapularis

<400> SEQUENCE: 105

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser
            100                 105


<210> SEQ ID NO 106
```

-continued

<211> LENGTH: 108
<212> TYPE: PRT
<213> ORGANISM: Ixodes scapularis

<400> SEQUENCE: 106

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr
            100                 105
```

<210> SEQ ID NO 107
<211> LENGTH: 109
<212> TYPE: PRT
<213> ORGANISM: Ixodes scapularis

<400> SEQUENCE: 107

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly
            100                 105
```

<210> SEQ ID NO 108
<211> LENGTH: 110
<212> TYPE: PRT
<213> ORGANISM: Ixodes scapularis

<400> SEQUENCE: 108

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80
```

-continued

```
Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr
            100                 105                 110


<210> SEQ ID NO 109
<211> LENGTH: 111
<212> TYPE: PRT
<213> ORGANISM: Ixodes scapularis

<400> SEQUENCE: 109

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp
            100                 105                 110


<210> SEQ ID NO 110
<211> LENGTH: 112
<212> TYPE: PRT
<213> ORGANISM: Ixodes scapularis

<400> SEQUENCE: 110

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110


<210> SEQ ID NO 111
<211> LENGTH: 113
<212> TYPE: PRT
<213> ORGANISM: Ixodes scapularis

<400> SEQUENCE: 111

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
```

-continued

```
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp


<210> SEQ ID NO 112
<211> LENGTH: 114
<212> TYPE: PRT
<213> ORGANISM: Ixodes scapularis

<400> SEQUENCE: 112

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser


<210> SEQ ID NO 113
<211> LENGTH: 115
<212> TYPE: PRT
<213> ORGANISM: Ixodes scapularis

<400> SEQUENCE: 113

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn
        115
```

-continued

```
<210> SEQ ID NO 114
<211> LENGTH: 116
<212> TYPE: PRT
<213> ORGANISM: Ixodes scapularis

<400> SEQUENCE: 114

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr
        115


<210> SEQ ID NO 115
<211> LENGTH: 117
<212> TYPE: PRT
<213> ORGANISM: Ixodes scapularis

<400> SEQUENCE: 115

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly
        115


<210> SEQ ID NO 116
<211> LENGTH: 118
<212> TYPE: PRT
<213> ORGANISM: Ixodes scapularis

<400> SEQUENCE: 116

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
```

-continued

```
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser
        115


<210> SEQ ID NO 117
<211> LENGTH: 119
<212> TYPE: PRT
<213> ORGANISM: Ixodes scapularis

<400> SEQUENCE: 117

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser
        115


<210> SEQ ID NO 118
<211> LENGTH: 120
<212> TYPE: PRT
<213> ORGANISM: Ixodes scapularis

<400> SEQUENCE: 118

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala
```

```
        115                 120


<210> SEQ ID NO 119
<211> LENGTH: 121
<212> TYPE: PRT
<213> ORGANISM: Ixodes scapularis

<400> SEQUENCE: 119

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala
        115                 120


<210> SEQ ID NO 120
<211> LENGTH: 122
<212> TYPE: PRT
<213> ORGANISM: Ixodes scapularis

<400> SEQUENCE: 120

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala
        115                 120


<210> SEQ ID NO 121
<211> LENGTH: 123
<212> TYPE: PRT
<213> ORGANISM: Ixodes scapularis

<400> SEQUENCE: 121

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30
```

-continued

```
Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys
        115                 120


<210> SEQ ID NO 122
<211> LENGTH: 124
<212> TYPE: PRT
<213> ORGANISM: Ixodes scapularis

<400> SEQUENCE: 122

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val
        115                 120


<210> SEQ ID NO 123
<211> LENGTH: 125
<212> TYPE: PRT
<213> ORGANISM: Ixodes scapularis

<400> SEQUENCE: 123

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110
```

-continued

```
Asp Ser Asn Thr Gly Ser Ser Ala Ala Ala Lys Val Thr
        115                 120                 125


<210> SEQ ID NO 124
<211> LENGTH: 126
<212> TYPE: PRT
<213> ORGANISM: Ixodes scapularis

<400> SEQUENCE: 124

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu
        115                 120                 125


<210> SEQ ID NO 125
<211> LENGTH: 127
<212> TYPE: PRT
<213> ORGANISM: Ixodes scapularis

<400> SEQUENCE: 125

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala
        115                 120                 125


<210> SEQ ID NO 126
<211> LENGTH: 128
<212> TYPE: PRT
<213> ORGANISM: Ixodes scapularis

<400> SEQUENCE: 126

Ser Glu Asp Gly Leu Glu Gln Asp Thr Ile Val Glu Thr Thr Thr Gln
 1               5                  10                  15
```

-continued

```
Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125


<210> SEQ ID NO 127
<211> LENGTH: 129
<212> TYPE: PRT
<213> ORGANISM: Ixodes scapularis

<400> SEQUENCE: 127

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile


<210> SEQ ID NO 128
<211> LENGTH: 130
<212> TYPE: PRT
<213> ORGANISM: Ixodes scapularis

<400> SEQUENCE: 128

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
```

-continued

```
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile
    130


<210> SEQ ID NO 129
<211> LENGTH: 131
<212> TYPE: PRT
<213> ORGANISM: Ixodes scapularis

<400> SEQUENCE: 129

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu
    130


<210> SEQ ID NO 130
<211> LENGTH: 132
<212> TYPE: PRT
<213> ORGANISM: Ixodes scapularis

<400> SEQUENCE: 130

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala
```

-continued

```
    130


<210> SEQ ID NO 131
<211> LENGTH: 133
<212> TYPE: PRT
<213> ORGANISM: Ixodes scapularis

<400> SEQUENCE: 131

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu
    130


<210> SEQ ID NO 132
<211> LENGTH: 134
<212> TYPE: PRT
<213> ORGANISM: Ixodes scapularis

<400> SEQUENCE: 132

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu
    130


<210> SEQ ID NO 133
<211> LENGTH: 135
<212> TYPE: PRT
<213> ORGANISM: Ixodes scapularis

<400> SEQUENCE: 133
```

-continued

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu Asn
    130                 135


<210> SEQ ID NO 134
<211> LENGTH: 136
<212> TYPE: PRT
<213> ORGANISM: Ixodes scapularis

<400> SEQUENCE: 134

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu Asn Cys
    130                 135


<210> SEQ ID NO 135
<211> LENGTH: 137
<212> TYPE: PRT
<213> ORGANISM: Ixodes scapularis

<400> SEQUENCE: 135

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45
```

-continued

```
Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu Asn Cys Thr
    130                 135


<210> SEQ ID NO 136
<211> LENGTH: 138
<212> TYPE: PRT
<213> ORGANISM: Ixodes scapularis

<400> SEQUENCE: 136

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu Asn Cys Thr Ala
    130                 135


<210> SEQ ID NO 137
<211> LENGTH: 139
<212> TYPE: PRT
<213> ORGANISM: Ixodes scapularis

<400> SEQUENCE: 137

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95
```

-continued

```
Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu Asn Cys Thr Ala His
    130                 135
```

<210> SEQ ID NO 138
<211> LENGTH: 140
<212> TYPE: PRT
<213> ORGANISM: Ixodes scapularis

<400> SEQUENCE: 138

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu Asn Cys Thr Ala His Ile
    130                 135                 140
```

<210> SEQ ID NO 139
<211> LENGTH: 141
<212> TYPE: PRT
<213> ORGANISM: Ixodes scapularis

<400> SEQUENCE: 139

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu Asn Cys Thr Ala His Ile Thr
    130                 135                 140
```

-continued

<210> SEQ ID NO 140
<211> LENGTH: 142
<212> TYPE: PRT
<213> ORGANISM: Ixodes scapularis

<400> SEQUENCE: 140

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu Asn Cys Thr Ala His Ile Thr Gly
    130                 135                 140
```

<210> SEQ ID NO 141
<211> LENGTH: 143
<212> TYPE: PRT
<213> ORGANISM: Ixodes scapularis

<400> SEQUENCE: 141

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu Asn Cys Thr Ala His Ile Thr Gly Trp
    130                 135                 140
```

<210> SEQ ID NO 142
<211> LENGTH: 144
<212> TYPE: PRT
<213> ORGANISM: Ixodes scapularis

<400> SEQUENCE: 142

-continued

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu Asn Cys Thr Ala His Ile Thr Gly Trp Thr
    130                 135                 140


<210> SEQ ID NO 143
<211> LENGTH: 145
<212> TYPE: PRT
<213> ORGANISM: Ixodes scapularis

<400> SEQUENCE: 143

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu Asn Cys Thr Ala His Ile Thr Gly Trp Thr
    130                 135                 140

Thr
145


<210> SEQ ID NO 144
<211> LENGTH: 146
<212> TYPE: PRT
<213> ORGANISM: Ixodes scapularis

<400> SEQUENCE: 144

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30
```

-continued

```
Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu Asn Cys Thr Ala His Ile Thr Gly Trp Thr
    130                 135                 140

Thr Glu
145


<210> SEQ ID NO 145
<211> LENGTH: 147
<212> TYPE: PRT
<213> ORGANISM: Ixodes scapularis

<400> SEQUENCE: 145

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu Asn Cys Thr Ala His Ile Thr Gly Trp Thr
    130                 135                 140

Thr Glu Thr
145


<210> SEQ ID NO 146
<211> LENGTH: 148
<212> TYPE: PRT
<213> ORGANISM: Ixodes scapularis

<400> SEQUENCE: 146

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45
```

-continued

```
Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu Asn Cys Thr Ala His Ile Thr Gly Trp Thr
    130                 135                 140

Thr Glu Thr Pro
145


<210> SEQ ID NO 147
<211> LENGTH: 149
<212> TYPE: PRT
<213> ORGANISM: Ixodes scapularis

<400> SEQUENCE: 147

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu Asn Cys Thr Ala His Ile Thr Gly Trp Thr
    130                 135                 140

Thr Glu Thr Pro Thr
145


<210> SEQ ID NO 148
<211> LENGTH: 150
<212> TYPE: PRT
<213> ORGANISM: Ixodes scapularis

<400> SEQUENCE: 148

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60
```

-continued

```
Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu Asn Cys Thr Ala His Ile Thr Gly Trp Thr
    130                 135                 140

Thr Glu Thr Pro Thr Thr
145                 150


<210> SEQ ID NO 149
<211> LENGTH: 151
<212> TYPE: PRT
<213> ORGANISM: Ixodes scapularis

<400> SEQUENCE: 149

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu Asn Cys Thr Ala His Ile Thr Gly Trp Thr
    130                 135                 140

Thr Glu Thr Pro Thr Thr Leu
145                 150


<210> SEQ ID NO 150
<211> LENGTH: 152
<212> TYPE: PRT
<213> ORGANISM: Ixodes scapularis

<400> SEQUENCE: 150

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80
```

-continued

```
Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu Asn Cys Thr Ala His Ile Thr Gly Trp Thr
    130                 135                 140

Thr Glu Thr Pro Thr Thr Leu Glu
145                 150


<210> SEQ ID NO 151
<211> LENGTH: 153
<212> TYPE: PRT
<213> ORGANISM: Ixodes scapularis

<400> SEQUENCE: 151

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu Asn Cys Thr Ala His Ile Thr Gly Trp Thr
    130                 135                 140

Thr Glu Thr Pro Thr Thr Leu Glu Pro
145                 150


<210> SEQ ID NO 152
<211> LENGTH: 154
<212> TYPE: PRT
<213> ORGANISM: Ixodes scapularis

<400> SEQUENCE: 152

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95
```

-continued

```
Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu Asn Cys Thr Ala His Ile Thr Gly Trp Thr
    130                 135                 140

Thr Glu Thr Pro Thr Thr Leu Glu Pro Thr
145                 150


<210> SEQ ID NO 153
<211> LENGTH: 155
<212> TYPE: PRT
<213> ORGANISM: Ixodes scapularis

<400> SEQUENCE: 153

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu Asn Cys Thr Ala His Ile Thr Gly Trp Thr
    130                 135                 140

Thr Glu Thr Pro Thr Thr Leu Glu Pro Thr Thr
145                 150                 155


<210> SEQ ID NO 154
<211> LENGTH: 156
<212> TYPE: PRT
<213> ORGANISM: Ixodes scapularis

<400> SEQUENCE: 154

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110
```

-continued

```
Asp Ser Asn Thr Gly Ser Ser Ala Ala Ala Lys Val Thr Glu Ala Leu
        115                 120                 125

Ile Ile Glu Ala Glu Glu Asn Cys Thr Ala His Ile Thr Gly Trp Thr
    130                 135                 140

Thr Glu Thr Pro Thr Thr Leu Glu Pro Thr Thr Glu
145                 150                 155


<210> SEQ ID NO 155
<211> LENGTH: 157
<212> TYPE: PRT
<213> ORGANISM: Ixodes scapularis

<400> SEQUENCE: 155

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu Asn Cys Thr Ala His Ile Thr Gly Trp Thr
    130                 135                 140

Thr Glu Thr Pro Thr Thr Leu Glu Pro Thr Thr Glu Ser
145                 150                 155


<210> SEQ ID NO 156
<211> LENGTH: 158
<212> TYPE: PRT
<213> ORGANISM: Ixodes scapularis

<400> SEQUENCE: 156

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125
```

-continued

```
Ile Ile Glu Ala Glu Glu Asn Cys Thr Ala His Ile Thr Gly Trp Thr
    130                 135                 140

Thr Glu Thr Pro Thr Thr Leu Glu Pro Thr Thr Glu Ser Gln
145                 150                 155


<210> SEQ ID NO 157
<211> LENGTH: 159
<212> TYPE: PRT
<213> ORGANISM: Ixodes scapularis

<400> SEQUENCE: 157

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu Asn Cys Thr Ala His Ile Thr Gly Trp Thr
    130                 135                 140

Thr Glu Thr Pro Thr Thr Leu Glu Pro Thr Thr Glu Ser Gln Phe
145                 150                 155


<210> SEQ ID NO 158
<211> LENGTH: 160
<212> TYPE: PRT
<213> ORGANISM: Ixodes scapularis

<400> SEQUENCE: 158

Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu Asn Cys Thr Ala His Ile Thr Gly Trp Thr
    130                 135                 140
```

-continued

```
Thr Glu Thr Pro Thr Thr Leu Glu Pro Thr Thr Glu Ser Gln Phe Glu
145                 150                 155                 160
```

<210> SEQ ID NO 159
<211> LENGTH: 161
<212> TYPE: PRT
<213> ORGANISM: Ixodes scapularis

<400> SEQUENCE: 159

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu Asn Cys Thr Ala His Ile Thr Gly Trp Thr
    130                 135                 140

Thr Glu Thr Pro Thr Thr Leu Glu Pro Thr Thr Glu Ser Gln Phe Glu
145                 150                 155                 160

Ala
```

<210> SEQ ID NO 160
<211> LENGTH: 162
<212> TYPE: PRT
<213> ORGANISM: Ixodes scapularis

<400> SEQUENCE: 160

```
Ser Glu Asp Gly Leu Glu Gln Asp Thr Ile Val Glu Thr Thr Thr Gln
 1               5                  10                  15

Asn Leu Tyr Glu Arg His Tyr Arg Asn His Ser Gly Leu Cys Gly Ala
            20                  25                  30

Gln Tyr Arg Asn Ser Ser His Ala Glu Ala Val Tyr Asn Cys Thr Leu
        35                  40                  45

Asn His Leu Pro Pro Val Val Asn Ala Thr Trp Glu Gly Ile Arg His
    50                  55                  60

Arg Ile Asn Lys Thr Ile Pro Gln Phe Val Lys Leu Ile Cys Asn Phe
65                  70                  75                  80

Thr Val Ala Met Pro Gln Glu Phe Tyr Leu Val Tyr Met Gly Ser Asp
                85                  90                  95

Gly Asn Ser Asp Phe Glu Glu Asp Lys Glu Ser Thr Gly Thr Asp Glu
            100                 105                 110

Asp Ser Asn Thr Gly Ser Ser Ala Ala Ala Lys Val Thr Glu Ala Leu
        115                 120                 125

Ile Ile Glu Ala Glu Glu Asn Cys Thr Ala His Ile Thr Gly Trp Thr
    130                 135                 140

Thr Glu Thr Pro Thr Thr Leu Glu Pro Thr Thr Glu Ser Gln Phe Glu
```

-continued 145 150 155 160

Ala Ile

<210> SEQ ID NO 161
<211> LENGTH: 163
<212> TYPE: PRT
<213> ORGANISM: Ixodes scapularis

<400> SEQUENCE: 161

Ser Glu Asp Gly Leu Glu Gln Asp Thr Ile Val Glu Thr Thr Thr Gln
1 5 10 15

Asn Leu Tyr Glu Arg His Tyr Arg Asn His Ser Gly Leu Cys Gly Ala
20 25 30

Gln Tyr Arg Asn Ser Ser His Ala Glu Ala Val Tyr Asn Cys Thr Leu
35 40 45

Asn His Leu Pro Pro Val Val Asn Ala Thr Trp Glu Gly Ile Arg His
50 55 60

Arg Ile Asn Lys Thr Ile Pro Gln Phe Val Lys Leu Ile Cys Asn Phe
65 70 75 80

Thr Val Ala Met Pro Gln Glu Phe Tyr Leu Val Tyr Met Gly Ser Asp
85 90 95

Gly Asn Ser Asp Phe Glu Glu Asp Lys Glu Ser Thr Gly Thr Asp Glu
100 105 110

Asp Ser Asn Thr Gly Ser Ser Ala Ala Ala Lys Val Thr Glu Ala Leu
115 120 125

Ile Ile Glu Ala Glu Glu Asn Cys Thr Ala His Ile Thr Gly Trp Thr
130 135 140

Thr Glu Thr Pro Thr Thr Leu Glu Pro Thr Thr Glu Ser Gln Phe Glu
145 150 155 160

Ala Ile Pro

<210> SEQ ID NO 162
<211> LENGTH: 3
<212> TYPE: PRT
<213> ORGANISM: Ixodes scapularis

<400> SEQUENCE: 162

Ala Ile Pro
1

<210> SEQ ID NO 163
<211> LENGTH: 4
<212> TYPE: PRT
<213> ORGANISM: Ixodes scapularis

<400> SEQUENCE: 163

Glu Ala Ile Pro
1

<210> SEQ ID NO 164
<211> LENGTH: 5
<212> TYPE: PRT
<213> ORGANISM: Ixodes scapularis

<400> SEQUENCE: 164

Phe Glu Ala Ile Pro
1 5

<210> SEQ ID NO 165

-continued

```
<211> LENGTH: 6
<212> TYPE: PRT
<213> ORGANISM: Ixodes scapularis

<400> SEQUENCE: 165

Gln Phe Glu Ala Ile Pro
 1               5


<210> SEQ ID NO 166
<211> LENGTH: 7
<212> TYPE: PRT
<213> ORGANISM: Ixodes scapularis

<400> SEQUENCE: 166

Ser Gln Phe Glu Ala Ile Pro
 1               5


<210> SEQ ID NO 167
<211> LENGTH: 8
<212> TYPE: PRT
<213> ORGANISM: Ixodes scapularis

<400> SEQUENCE: 167

Glu Ser Gln Phe Glu Ala Ile Pro
 1               5


<210> SEQ ID NO 168
<211> LENGTH: 9
<212> TYPE: PRT
<213> ORGANISM: Ixodes scapularis

<400> SEQUENCE: 168

Thr Glu Ser Gln Phe Glu Ala Ile Pro
 1               5


<210> SEQ ID NO 169
<211> LENGTH: 10
<212> TYPE: PRT
<213> ORGANISM: Ixodes scapularis

<400> SEQUENCE: 169

Thr Thr Glu Ser Gln Phe Glu Ala Ile Pro
 1               5                   10


<210> SEQ ID NO 170
<211> LENGTH: 11
<212> TYPE: PRT
<213> ORGANISM: Ixodes scapularis

<400> SEQUENCE: 170

Pro Thr Thr Glu Ser Gln Phe Glu Ala Ile Pro
 1               5                   10


<210> SEQ ID NO 171
<211> LENGTH: 12
<212> TYPE: PRT
<213> ORGANISM: Ixodes scapularis

<400> SEQUENCE: 171

Glu Pro Thr Thr Glu Ser Gln Phe Glu Ala Ile Pro
 1               5                   10


<210> SEQ ID NO 172
<211> LENGTH: 13
<212> TYPE: PRT
```

-continued

<213> ORGANISM: Ixodes scapularis

<400> SEQUENCE: 172

Leu Glu Pro Thr Thr Glu Ser Gln Phe Glu Ala Ile Pro
1 5 10

<210> SEQ ID NO 173
<211> LENGTH: 14
<212> TYPE: PRT
<213> ORGANISM: Ixodes scapularis

<400> SEQUENCE: 173

Thr Leu Glu Pro Thr Thr Glu Ser Gln Phe Glu Ala Ile Pro
1 5 10

<210> SEQ ID NO 174
<211> LENGTH: 15
<212> TYPE: PRT
<213> ORGANISM: Ixodes scapularis

<400> SEQUENCE: 174

Thr Thr Leu Glu Pro Thr Thr Glu Ser Gln Phe Glu Ala Ile Pro
1 5 10 15

<210> SEQ ID NO 175
<211> LENGTH: 16
<212> TYPE: PRT
<213> ORGANISM: Ixodes scapularis

<400> SEQUENCE: 175

Pro Thr Thr Leu Glu Pro Thr Thr Glu Ser Gln Phe Glu Ala Ile Pro
1 5 10 15

<210> SEQ ID NO 176
<211> LENGTH: 17
<212> TYPE: PRT
<213> ORGANISM: Ixodes scapularis

<400> SEQUENCE: 176

Thr Pro Thr Thr Leu Glu Pro Thr Thr Glu Ser Gln Phe Glu Ala Ile
1 5 10 15

Pro

<210> SEQ ID NO 177
<211> LENGTH: 18
<212> TYPE: PRT
<213> ORGANISM: Ixodes scapularis

<400> SEQUENCE: 177

Glu Thr Pro Thr Thr Leu Glu Pro Thr Thr Glu Ser Gln Phe Glu Ala
1 5 10 15

Ile Pro

<210> SEQ ID NO 178
<211> LENGTH: 19
<212> TYPE: PRT
<213> ORGANISM: Ixodes scapularis

<400> SEQUENCE: 178

Thr Glu Thr Pro Thr Thr Leu Glu Pro Thr Thr Glu Ser Gln Phe Glu
1 5 10 15

Ala Ile Pro

-continued

<210> SEQ ID NO 179
<211> LENGTH: 20
<212> TYPE: PRT
<213> ORGANISM: Ixodes scapularis

<400> SEQUENCE: 179

Thr Thr Glu Thr Pro Thr Thr Leu Glu Pro Thr Thr Glu Ser Gln Phe
 1               5                   10                  15

Glu Ala Ile Pro
            20

<210> SEQ ID NO 180
<211> LENGTH: 21
<212> TYPE: PRT
<213> ORGANISM: Ixodes scapularis

<400> SEQUENCE: 180

Trp Thr Thr Glu Thr Pro Thr Thr Leu Glu Pro Thr Thr Glu Ser Gln
 1               5                   10                  15

Phe Glu Ala Ile Pro
            20

<210> SEQ ID NO 181
<211> LENGTH: 22
<212> TYPE: PRT
<213> ORGANISM: Ixodes scapularis

<400> SEQUENCE: 181

Gly Trp Thr Thr Glu Thr Pro Thr Thr Leu Glu Pro Thr Thr Glu Ser
 1               5                   10                  15

Gln Phe Glu Ala Ile Pro
            20

<210> SEQ ID NO 182
<211> LENGTH: 23
<212> TYPE: PRT
<213> ORGANISM: Ixodes scapularis

<400> SEQUENCE: 182

Thr Gly Trp Thr Thr Glu Thr Pro Thr Thr Leu Glu Pro Thr Thr Glu
 1               5                   10                  15

Ser Gln Phe Glu Ala Ile Pro
            20

<210> SEQ ID NO 183
<211> LENGTH: 24
<212> TYPE: PRT
<213> ORGANISM: Ixodes scapularis

<400> SEQUENCE: 183

Ile Thr Gly Trp Thr Thr Glu Thr Pro Thr Thr Leu Glu Pro Thr Thr
 1               5                   10                  15

Glu Ser Gln Phe Glu Ala Ile Pro
            20

<210> SEQ ID NO 184
<211> LENGTH: 25
<212> TYPE: PRT
<213> ORGANISM: Ixodes scapularis

<400> SEQUENCE: 184

His Ile Thr Gly Trp Thr Thr Glu Thr Pro Thr Thr Leu Glu Pro Thr

-continued

```
 1               5                   10                  15

Thr Glu Ser Gln Phe Glu Ala Ile Pro
            20                  25


<210> SEQ ID NO 185
<211> LENGTH: 26
<212> TYPE: PRT
<213> ORGANISM: Ixodes scapularis

<400> SEQUENCE: 185

Ala His Ile Thr Gly Trp Thr Thr Glu Thr Pro Thr Thr Leu Glu Pro
 1               5                   10                  15

Thr Thr Glu Ser Gln Phe Glu Ala Ile Pro
            20                  25


<210> SEQ ID NO 186
<211> LENGTH: 27
<212> TYPE: PRT
<213> ORGANISM: Ixodes scapularis

<400> SEQUENCE: 186

Thr Ala His Ile Thr Gly Trp Thr Thr Glu Thr Pro Thr Thr Leu Glu
 1               5                   10                  15

Pro Thr Thr Glu Ser Gln Phe Glu Ala Ile Pro
            20                  25


<210> SEQ ID NO 187
<211> LENGTH: 28
<212> TYPE: PRT
<213> ORGANISM: Ixodes scapularis

<400> SEQUENCE: 187

Cys Thr Ala His Ile Thr Gly Trp Thr Thr Glu Thr Pro Thr Thr Leu
 1               5                   10                  15

Glu Pro Thr Thr Glu Ser Gln Phe Glu Ala Ile Pro
            20                  25


<210> SEQ ID NO 188
<211> LENGTH: 29
<212> TYPE: PRT
<213> ORGANISM: Ixodes scapularis

<400> SEQUENCE: 188

Asn Cys Thr Ala His Ile Thr Gly Trp Thr Thr Glu Thr Pro Thr Thr
 1               5                   10                  15

Leu Glu Pro Thr Thr Glu Ser Gln Phe Glu Ala Ile Pro
            20                  25


<210> SEQ ID NO 189
<211> LENGTH: 30
<212> TYPE: PRT
<213> ORGANISM: Ixodes scapularis

<400> SEQUENCE: 189

Glu Asn Cys Thr Ala His Ile Thr Gly Trp Thr Thr Glu Thr Pro Thr
 1               5                   10                  15

Thr Leu Glu Pro Thr Thr Glu Ser Gln Phe Glu Ala Ile Pro
            20                  25                  30


<210> SEQ ID NO 190
<211> LENGTH: 31
<212> TYPE: PRT
```

-continued

<213> ORGANISM: Ixodes scapularis

<400> SEQUENCE: 190

Glu Glu Asn Cys Thr Ala His Ile Thr Gly Trp Thr Thr Glu Thr Pro
1 5 10 15

Thr Thr Leu Glu Pro Thr Thr Glu Ser Gln Phe Glu Ala Ile Pro
20 25 30

<210> SEQ ID NO 191
<211> LENGTH: 32
<212> TYPE: PRT
<213> ORGANISM: Ixodes scapularis

<400> SEQUENCE: 191

Ala Glu Glu Asn Cys Thr Ala His Ile Thr Gly Trp Thr Thr Glu Thr
1 5 10 15

Pro Thr Thr Leu Glu Pro Thr Thr Glu Ser Gln Phe Glu Ala Ile Pro
20 25 30

<210> SEQ ID NO 192
<211> LENGTH: 33
<212> TYPE: PRT
<213> ORGANISM: Ixodes scapularis

<400> SEQUENCE: 192

Glu Ala Glu Glu Asn Cys Thr Ala His Ile Thr Gly Trp Thr Thr Glu
1 5 10 15

Thr Pro Thr Thr Leu Glu Pro Thr Thr Glu Ser Gln Phe Glu Ala Ile
20 25 30

Pro

<210> SEQ ID NO 193
<211> LENGTH: 34
<212> TYPE: PRT
<213> ORGANISM: Ixodes scapularis

<400> SEQUENCE: 193

Ile Glu Ala Glu Glu Asn Cys Thr Ala His Ile Thr Gly Trp Thr Thr
1 5 10 15

Glu Thr Pro Thr Thr Leu Glu Pro Thr Thr Glu Ser Gln Phe Glu Ala
20 25 30

Ile Pro

<210> SEQ ID NO 194
<211> LENGTH: 35
<212> TYPE: PRT
<213> ORGANISM: Ixodes scapularis

<400> SEQUENCE: 194

Ile Ile Glu Ala Glu Glu Asn Cys Thr Ala His Ile Thr Gly Trp Thr
1 5 10 15

Thr Glu Thr Pro Thr Thr Leu Glu Pro Thr Thr Glu Ser Gln Phe Glu
20 25 30

Ala Ile Pro
35

<210> SEQ ID NO 195
<211> LENGTH: 36
<212> TYPE: PRT
<213> ORGANISM: Ixodes scapularis -continued

<400> SEQUENCE: 195

```
Leu Ile Ile Glu Ala Glu Glu Asn Cys Thr Ala His Ile Thr Gly Trp
 1              5                   10                  15

Thr Thr Glu Thr Pro Thr Thr Leu Glu Pro Thr Thr Glu Ser Gln Phe
            20                  25                  30

Glu Ala Ile Pro
        35
```

<210> SEQ ID NO 196
<211> LENGTH: 37
<212> TYPE: PRT
<213> ORGANISM: Ixodes scapularis

<400> SEQUENCE: 196

```
Ala Leu Ile Ile Glu Ala Glu Glu Asn Cys Thr Ala His Ile Thr Gly
 1              5                   10                  15

Trp Thr Thr Glu Thr Pro Thr Thr Leu Glu Pro Thr Thr Glu Ser Gln
            20                  25                  30

Phe Glu Ala Ile Pro
        35
```

<210> SEQ ID NO 197
<211> LENGTH: 38
<212> TYPE: PRT
<213> ORGANISM: Ixodes scapularis

<400> SEQUENCE: 197

```
Glu Ala Leu Ile Ile Glu Ala Glu Glu Asn Cys Thr Ala His Ile Thr
 1              5                   10                  15

Gly Trp Thr Thr Glu Thr Pro Thr Thr Leu Glu Pro Thr Thr Glu Ser
            20                  25                  30

Gln Phe Glu Ala Ile Pro
        35
```

<210> SEQ ID NO 198
<211> LENGTH: 39
<212> TYPE: PRT
<213> ORGANISM: Ixodes scapularis

<400> SEQUENCE: 198

```
Thr Glu Ala Leu Ile Ile Glu Ala Glu Glu Asn Cys Thr Ala His Ile
 1              5                   10                  15

Thr Gly Trp Thr Thr Glu Thr Pro Thr Thr Leu Glu Pro Thr Thr Glu
            20                  25                  30

Ser Gln Phe Glu Ala Ile Pro
        35
```

<210> SEQ ID NO 199
<211> LENGTH: 40
<212> TYPE: PRT
<213> ORGANISM: Ixodes scapularis

<400> SEQUENCE: 199

```
Val Thr Glu Ala Leu Ile Ile Glu Ala Glu Glu Asn Cys Thr Ala His
 1              5                   10                  15

Ile Thr Gly Trp Thr Thr Glu Thr Pro Thr Thr Leu Glu Pro Thr Thr
            20                  25                  30

Glu Ser Gln Phe Glu Ala Ile Pro
        35                  40
```

-continued

<210> SEQ ID NO 200
<211> LENGTH: 41
<212> TYPE: PRT
<213> ORGANISM: Ixodes scapularis

<400> SEQUENCE: 200

Lys Val Thr Glu Ala Leu Ile Ile Glu Ala Glu Glu Asn Cys Thr Ala
1 5 10 15

His Ile Thr Gly Trp Thr Thr Glu Thr Pro Thr Thr Leu Glu Pro Thr
20 25 30

Thr Glu Ser Gln Phe Glu Ala Ile Pro
35 40

<210> SEQ ID NO 201
<211> LENGTH: 42
<212> TYPE: PRT
<213> ORGANISM: Ixodes scapularis

<400> SEQUENCE: 201

Ala Lys Val Thr Glu Ala Leu Ile Ile Glu Ala Glu Glu Asn Cys Thr
1 5 10 15

Ala His Ile Thr Gly Trp Thr Thr Glu Thr Pro Thr Thr Leu Glu Pro
20 25 30

Thr Thr Glu Ser Gln Phe Glu Ala Ile Pro
35 40

<210> SEQ ID NO 202
<211> LENGTH: 43
<212> TYPE: PRT
<213> ORGANISM: Ixodes scapularis

<400> SEQUENCE: 202

Ala Ala Lys Val Thr Glu Ala Leu Ile Ile Glu Ala Glu Glu Asn Cys
1 5 10 15

Thr Ala His Ile Thr Gly Trp Thr Thr Glu Thr Pro Thr Thr Leu Glu
20 25 30

Pro Thr Thr Glu Ser Gln Phe Glu Ala Ile Pro
35 40

<210> SEQ ID NO 203
<211> LENGTH: 44
<212> TYPE: PRT
<213> ORGANISM: Ixodes scapularis

<400> SEQUENCE: 203

Ala Ala Ala Lys Val Thr Glu Ala Leu Ile Ile Glu Ala Glu Glu Asn
1 5 10 15

Cys Thr Ala His Ile Thr Gly Trp Thr Thr Glu Thr Pro Thr Thr Leu
20 25 30

Glu Pro Thr Thr Glu Ser Gln Phe Glu Ala Ile Pro
35 40

<210> SEQ ID NO 204
<211> LENGTH: 45
<212> TYPE: PRT
<213> ORGANISM: Ixodes scapularis

<400> SEQUENCE: 204

Ser Ala Ala Ala Lys Val Thr Glu Ala Leu Ile Ile Glu Ala Glu Glu
1 5 10 15

-continued

```
Asn Cys Thr Ala His Ile Thr Gly Trp Thr Thr Glu Thr Pro Thr Thr
            20                  25                  30

Leu Glu Pro Thr Thr Glu Ser Gln Phe Glu Ala Ile Pro
        35                  40                  45


<210> SEQ ID NO 205
<211> LENGTH: 46
<212> TYPE: PRT
<213> ORGANISM: Ixodes scapularis

<400> SEQUENCE: 205

Ser Ser Ala Ala Ala Lys Val Thr Glu Ala Leu Ile Ile Glu Ala Glu
 1               5                  10                  15

Glu Asn Cys Thr Ala His Ile Thr Gly Trp Thr Thr Glu Thr Pro Thr
            20                  25                  30

Thr Leu Glu Pro Thr Thr Glu Ser Gln Phe Glu Ala Ile Pro
        35                  40                  45


<210> SEQ ID NO 206
<211> LENGTH: 47
<212> TYPE: PRT
<213> ORGANISM: Ixodes scapularis

<400> SEQUENCE: 206

Gly Ser Ser Ala Ala Ala Lys Val Thr Glu Ala Leu Ile Ile Glu Ala
 1               5                  10                  15

Glu Glu Asn Cys Thr Ala His Ile Thr Gly Trp Thr Thr Glu Thr Pro
            20                  25                  30

Thr Thr Leu Glu Pro Thr Thr Glu Ser Gln Phe Glu Ala Ile Pro
        35                  40                  45


<210> SEQ ID NO 207
<211> LENGTH: 48
<212> TYPE: PRT
<213> ORGANISM: Ixodes scapularis

<400> SEQUENCE: 207

Thr Gly Ser Ser Ala Ala Ala Lys Val Thr Glu Ala Leu Ile Ile Glu
 1               5                  10                  15

Ala Glu Glu Asn Cys Thr Ala His Ile Thr Gly Trp Thr Thr Glu Thr
            20                  25                  30

Pro Thr Thr Leu Glu Pro Thr Thr Glu Ser Gln Phe Glu Ala Ile Pro
        35                  40                  45


<210> SEQ ID NO 208
<211> LENGTH: 49
<212> TYPE: PRT
<213> ORGANISM: Ixodes scapularis

<400> SEQUENCE: 208

Asn Thr Gly Ser Ser Ala Ala Ala Lys Val Thr Glu Ala Leu Ile Ile
 1               5                  10                  15

Glu Ala Glu Glu Asn Cys Thr Ala His Ile Thr Gly Trp Thr Thr Glu
            20                  25                  30

Thr Pro Thr Thr Leu Glu Pro Thr Thr Glu Ser Gln Phe Glu Ala Ile
        35                  40                  45

Pro


<210> SEQ ID NO 209
<211> LENGTH: 50
```

-continued

<212> TYPE: PRT
<213> ORGANISM: Ixodes scapularis

<400> SEQUENCE: 209

```
Ser Asn Thr Gly Ser Ser Ala Ala Ala Lys Val Thr Glu Ala Leu Ile
 1               5                  10                  15

Ile Glu Ala Glu Glu Asn Cys Thr Ala His Ile Thr Gly Trp Thr Thr
            20                  25                  30

Glu Thr Pro Thr Thr Leu Glu Pro Thr Thr Glu Ser Gln Phe Glu Ala
        35                  40                  45

Ile Pro
    50
```

<210> SEQ ID NO 210
<211> LENGTH: 51
<212> TYPE: PRT
<213> ORGANISM: Ixodes scapularis

<400> SEQUENCE: 210

```
Asp Ser Asn Thr Gly Ser Ser Ala Ala Ala Lys Val Thr Glu Ala Leu
 1               5                  10                  15

Ile Ile Glu Ala Glu Glu Asn Cys Thr Ala His Ile Thr Gly Trp Thr
            20                  25                  30

Thr Glu Thr Pro Thr Thr Leu Glu Pro Thr Thr Glu Ser Gln Phe Glu
        35                  40                  45

Ala Ile Pro
    50
```

<210> SEQ ID NO 211
<211> LENGTH: 52
<212> TYPE: PRT
<213> ORGANISM: Ixodes scapularis

<400> SEQUENCE: 211

```
Glu Asp Ser Asn Thr Gly Ser Ser Ala Ala Ala Lys Val Thr Glu Ala
 1               5                  10                  15

Leu Ile Ile Glu Ala Glu Glu Asn Cys Thr Ala His Ile Thr Gly Trp
            20                  25                  30

Thr Thr Glu Thr Pro Thr Thr Leu Glu Pro Thr Thr Glu Ser Gln Phe
        35                  40                  45

Glu Ala Ile Pro
    50
```

<210> SEQ ID NO 212
<211> LENGTH: 53
<212> TYPE: PRT
<213> ORGANISM: Ixodes scapularis

<400> SEQUENCE: 212

```
Asp Glu Asp Ser Asn Thr Gly Ser Ser Ala Ala Ala Lys Val Thr Glu
 1               5                  10                  15

Ala Leu Ile Ile Glu Ala Glu Glu Asn Cys Thr Ala His Ile Thr Gly
            20                  25                  30

Trp Thr Thr Glu Thr Pro Thr Thr Leu Glu Pro Thr Thr Glu Ser Gln
        35                  40                  45

Phe Glu Ala Ile Pro
    50
```

<210> SEQ ID NO 213

-continued

<211> LENGTH: 54
<212> TYPE: PRT
<213> ORGANISM: Ixodes scapularis

<400> SEQUENCE: 213

```
Thr Asp Glu Asp Ser Asn Thr Gly Ser Ser Ala Ala Ala Lys Val Thr
 1               5                  10                  15

Glu Ala Leu Ile Ile Glu Ala Glu Glu Asn Cys Thr Ala His Ile Thr
            20                  25                  30

Gly Trp Thr Thr Glu Thr Pro Thr Thr Leu Glu Pro Thr Thr Glu Ser
        35                  40                  45

Gln Phe Glu Ala Ile Pro
    50
```

<210> SEQ ID NO 214
<211> LENGTH: 55
<212> TYPE: PRT
<213> ORGANISM: Ixodes scapularis

<400> SEQUENCE: 214

```
Gly Thr Asp Glu Asp Ser Asn Thr Gly Ser Ser Ala Ala Ala Lys Val
 1               5                  10                  15

Thr Glu Ala Leu Ile Ile Glu Ala Glu Glu Asn Cys Thr Ala His Ile
            20                  25                  30

Thr Gly Trp Thr Thr Glu Thr Pro Thr Thr Leu Glu Pro Thr Thr Glu
        35                  40                  45

Ser Gln Phe Glu Ala Ile Pro
    50                  55
```

<210> SEQ ID NO 215
<211> LENGTH: 56
<212> TYPE: PRT
<213> ORGANISM: Ixodes scapularis

<400> SEQUENCE: 215

```
Thr Gly Thr Asp Glu Asp Ser Asn Thr Gly Ser Ser Ala Ala Ala Lys
 1               5                  10                  15

Val Thr Glu Ala Leu Ile Ile Glu Ala Glu Glu Asn Cys Thr Ala His
            20                  25                  30

Ile Thr Gly Trp Thr Thr Glu Thr Pro Thr Thr Leu Glu Pro Thr Thr
        35                  40                  45

Glu Ser Gln Phe Glu Ala Ile Pro
    50                  55
```

<210> SEQ ID NO 216
<211> LENGTH: 57
<212> TYPE: PRT
<213> ORGANISM: Ixodes scapularis

<400> SEQUENCE: 216

```
Ser Thr Gly Thr Asp Glu Asp Ser Asn Thr Gly Ser Ser Ala Ala Ala
 1               5                  10                  15

Lys Val Thr Glu Ala Leu Ile Ile Glu Ala Glu Glu Asn Cys Thr Ala
            20                  25                  30

His Ile Thr Gly Trp Thr Thr Glu Thr Pro Thr Thr Leu Glu Pro Thr
        35                  40                  45

Thr Glu Ser Gln Phe Glu Ala Ile Pro
    50                  55
```

-continued

<210> SEQ ID NO 217
<211> LENGTH: 58
<212> TYPE: PRT
<213> ORGANISM: Ixodes scapularis

<400> SEQUENCE: 217

```
Glu Ser Thr Gly Thr Asp Glu Asp Ser Asn Thr Gly Ser Ser Ala Ala
 1               5                  10                  15

Ala Lys Val Thr Glu Ala Leu Ile Ile Glu Ala Glu Glu Asn Cys Thr
            20                  25                  30

Ala His Ile Thr Gly Trp Thr Thr Glu Thr Pro Thr Thr Leu Glu Pro
        35                  40                  45

Thr Thr Glu Ser Gln Phe Glu Ala Ile Pro
    50                  55
```

<210> SEQ ID NO 218
<211> LENGTH: 59
<212> TYPE: PRT
<213> ORGANISM: Ixodes scapularis

<400> SEQUENCE: 218

```
Lys Glu Ser Thr Gly Thr Asp Glu Asp Ser Asn Thr Gly Ser Ser Ala
 1               5                  10                  15

Ala Ala Lys Val Thr Glu Ala Leu Ile Ile Glu Ala Glu Glu Asn Cys
            20                  25                  30

Thr Ala His Ile Thr Gly Trp Thr Thr Glu Thr Pro Thr Thr Leu Glu
        35                  40                  45

Pro Thr Thr Glu Ser Gln Phe Glu Ala Ile Pro
    50                  55
```

<210> SEQ ID NO 219
<211> LENGTH: 60
<212> TYPE: PRT
<213> ORGANISM: Ixodes scapularis

<400> SEQUENCE: 219

```
Asp Lys Glu Ser Thr Gly Thr Asp Glu Asp Ser Asn Thr Gly Ser Ser
 1               5                  10                  15

Ala Ala Ala Lys Val Thr Glu Ala Leu Ile Ile Glu Ala Glu Glu Asn
            20                  25                  30

Cys Thr Ala His Ile Thr Gly Trp Thr Thr Glu Thr Pro Thr Thr Leu
        35                  40                  45

Glu Pro Thr Thr Glu Ser Gln Phe Glu Ala Ile Pro
    50                  55                  60
```

<210> SEQ ID NO 220
<211> LENGTH: 61
<212> TYPE: PRT
<213> ORGANISM: Ixodes scapularis

<400> SEQUENCE: 220

```
Glu Asp Lys Glu Ser Thr Gly Thr Asp Glu Asp Ser Asn Thr Gly Ser
 1               5                  10                  15

Ser Ala Ala Ala Lys Val Thr Glu Ala Leu Ile Ile Glu Ala Glu Glu
            20                  25                  30

Asn Cys Thr Ala His Ile Thr Gly Trp Thr Thr Glu Thr Pro Thr Thr
        35                  40                  45

Leu Glu Pro Thr Thr Glu Ser Gln Phe Glu Ala Ile Pro
    50                  55                  60
```

-continued

<210> SEQ ID NO 221
<211> LENGTH: 62
<212> TYPE: PRT
<213> ORGANISM: Ixodes scapularis

<400> SEQUENCE: 221

```
Glu Glu Asp Lys Glu Ser Thr Gly Thr Asp Glu Asp Ser Asn Thr Gly
 1               5                  10                  15

Ser Ser Ala Ala Ala Lys Val Thr Glu Ala Leu Ile Ile Glu Ala Glu
            20                  25                  30

Glu Asn Cys Thr Ala His Ile Thr Gly Trp Thr Thr Glu Thr Pro Thr
        35                  40                  45

Thr Leu Glu Pro Thr Thr Glu Ser Gln Phe Glu Ala Ile Pro
    50                  55                  60
```

<210> SEQ ID NO 222
<211> LENGTH: 63
<212> TYPE: PRT
<213> ORGANISM: Ixodes scapularis

<400> SEQUENCE: 222

```
Phe Glu Glu Asp Lys Glu Ser Thr Gly Thr Asp Glu Asp Ser Asn Thr
 1               5                  10                  15

Gly Ser Ser Ala Ala Ala Lys Val Thr Glu Ala Leu Ile Ile Glu Ala
            20                  25                  30

Glu Glu Asn Cys Thr Ala His Ile Thr Gly Trp Thr Thr Glu Thr Pro
        35                  40                  45

Thr Thr Leu Glu Pro Thr Thr Glu Ser Gln Phe Glu Ala Ile Pro
    50                  55                  60
```

<210> SEQ ID NO 223
<211> LENGTH: 64
<212> TYPE: PRT
<213> ORGANISM: Ixodes scapularis

<400> SEQUENCE: 223

```
Asp Phe Glu Glu Asp Lys Glu Ser Thr Gly Thr Asp Glu Asp Ser Asn
 1               5                  10                  15

Thr Gly Ser Ser Ala Ala Ala Lys Val Thr Glu Ala Leu Ile Ile Glu
            20                  25                  30

Ala Glu Glu Asn Cys Thr Ala His Ile Thr Gly Trp Thr Thr Glu Thr
        35                  40                  45

Pro Thr Thr Leu Glu Pro Thr Thr Glu Ser Gln Phe Glu Ala Ile Pro
    50                  55                  60
```

<210> SEQ ID NO 224
<211> LENGTH: 65
<212> TYPE: PRT
<213> ORGANISM: Ixodes scapularis

<400> SEQUENCE: 224

```
Ser Asp Phe Glu Glu Asp Lys Glu Ser Thr Gly Thr Asp Glu Asp Ser
 1               5                  10                  15

Asn Thr Gly Ser Ser Ala Ala Ala Lys Val Thr Glu Ala Leu Ile Ile
            20                  25                  30

Glu Ala Glu Glu Asn Cys Thr Ala His Ile Thr Gly Trp Thr Thr Glu
        35                  40                  45

Thr Pro Thr Thr Leu Glu Pro Thr Thr Glu Ser Gln Phe Glu Ala Ile
    50                  55                  60
```

-continued

Pro
65

<210> SEQ ID NO 225
<211> LENGTH: 66
<212> TYPE: PRT
<213> ORGANISM: Ixodes scapularis

<400> SEQUENCE: 225

Asn Ser Asp Phe Glu Glu Asp Lys Glu Ser Thr Gly Thr Asp Glu Asp
1 5 10 15

Ser Asn Thr Gly Ser Ser Ala Ala Ala Lys Val Thr Glu Ala Leu Ile
20 25 30

Ile Glu Ala Glu Glu Asn Cys Thr Ala His Ile Thr Gly Trp Thr Thr
35 40 45

Glu Thr Pro Thr Thr Leu Glu Pro Thr Thr Glu Ser Gln Phe Glu Ala
50 55 60

Ile Pro
65

<210> SEQ ID NO 226
<211> LENGTH: 67
<212> TYPE: PRT
<213> ORGANISM: Ixodes scapularis

<400> SEQUENCE: 226

Gly Asn Ser Asp Phe Glu Glu Asp Lys Glu Ser Thr Gly Thr Asp Glu
1 5 10 15

Asp Ser Asn Thr Gly Ser Ser Ala Ala Ala Lys Val Thr Glu Ala Leu
20 25 30

Ile Ile Glu Ala Glu Glu Asn Cys Thr Ala His Ile Thr Gly Trp Thr
35 40 45

Thr Glu Thr Pro Thr Thr Leu Glu Pro Thr Thr Glu Ser Gln Phe Glu
50 55 60

Ala Ile Pro
65

<210> SEQ ID NO 227
<211> LENGTH: 68
<212> TYPE: PRT
<213> ORGANISM: Ixodes scapularis

<400> SEQUENCE: 227

Asp Gly Asn Ser Asp Phe Glu Glu Asp Lys Glu Ser Thr Gly Thr Asp
1 5 10 15

Glu Asp Ser Asn Thr Gly Ser Ser Ala Ala Ala Lys Val Thr Glu Ala
20 25 30

Leu Ile Ile Glu Ala Glu Glu Asn Cys Thr Ala His Ile Thr Gly Trp
35 40 45

Thr Thr Glu Thr Pro Thr Thr Leu Glu Pro Thr Thr Glu Ser Gln Phe
50 55 60

Glu Ala Ile Pro
65

<210> SEQ ID NO 228
<211> LENGTH: 69
<212> TYPE: PRT
<213> ORGANISM: Ixodes scapularis -continued

<400> SEQUENCE: 228

```
Ser Asp Gly Asn Ser Asp Phe Glu Glu Asp Lys Glu Ser Thr Gly Thr
 1               5                  10                  15

Asp Glu Asp Ser Asn Thr Gly Ser Ser Ala Ala Ala Lys Val Thr Glu
            20                  25                  30

Ala Leu Ile Ile Glu Ala Glu Glu Asn Cys Thr Ala His Ile Thr Gly
        35                  40                  45

Trp Thr Thr Glu Thr Pro Thr Thr Leu Glu Pro Thr Thr Glu Ser Gln
    50                  55                  60

Phe Glu Ala Ile Pro
65
```

<210> SEQ ID NO 229
<211> LENGTH: 70
<212> TYPE: PRT
<213> ORGANISM: Ixodes scapularis

<400> SEQUENCE: 229

```
Gly Ser Asp Gly Asn Ser Asp Phe Glu Glu Asp Lys Glu Ser Thr Gly
 1               5                  10                  15

Thr Asp Glu Asp Ser Asn Thr Gly Ser Ser Ala Ala Ala Lys Val Thr
            20                  25                  30

Glu Ala Leu Ile Ile Glu Ala Glu Glu Asn Cys Thr Ala His Ile Thr
        35                  40                  45

Gly Trp Thr Thr Glu Thr Pro Thr Thr Leu Glu Pro Thr Thr Glu Ser
    50                  55                  60

Gln Phe Glu Ala Ile Pro
65                  70
```

<210> SEQ ID NO 230
<211> LENGTH: 71
<212> TYPE: PRT
<213> ORGANISM: Ixodes scapularis

<400> SEQUENCE: 230

```
Met Gly Ser Asp Gly Asn Ser Asp Phe Glu Glu Asp Lys Glu Ser Thr
 1               5                  10                  15

Gly Thr Asp Glu Asp Ser Asn Thr Gly Ser Ser Ala Ala Ala Lys Val
            20                  25                  30

Thr Glu Ala Leu Ile Ile Glu Ala Glu Glu Asn Cys Thr Ala His Ile
        35                  40                  45

Thr Gly Trp Thr Thr Glu Thr Pro Thr Thr Leu Glu Pro Thr Thr Glu
    50                  55                  60

Ser Gln Phe Glu Ala Ile Pro
65                  70
```

<210> SEQ ID NO 231
<211> LENGTH: 72
<212> TYPE: PRT
<213> ORGANISM: Ixodes scapularis

<400> SEQUENCE: 231

```
Tyr Met Gly Ser Asp Gly Asn Ser Asp Phe Glu Glu Asp Lys Glu Ser
 1               5                  10                  15

Thr Gly Thr Asp Glu Asp Ser Asn Thr Gly Ser Ser Ala Ala Ala Lys
            20                  25                  30

Val Thr Glu Ala Leu Ile Ile Glu Ala Glu Glu Asn Cys Thr Ala His
        35                  40                  45
```

-continued

```
Ile Thr Gly Trp Thr Thr Glu Thr Pro Thr Thr Leu Glu Pro Thr Thr
    50                  55                  60

Glu Ser Gln Phe Glu Ala Ile Pro
65                  70


<210> SEQ ID NO 232
<211> LENGTH: 73
<212> TYPE: PRT
<213> ORGANISM: Ixodes scapularis

<400> SEQUENCE: 232

Val Tyr Met Gly Ser Asp Gly Asn Ser Asp Phe Glu Glu Asp Lys Glu
 1               5                  10                  15

Ser Thr Gly Thr Asp Glu Asp Ser Asn Thr Gly Ser Ser Ala Ala Ala
            20                  25                  30

Lys Val Thr Glu Ala Leu Ile Ile Glu Ala Glu Glu Asn Cys Thr Ala
        35                  40                  45

His Ile Thr Gly Trp Thr Thr Glu Thr Pro Thr Thr Leu Glu Pro Thr
    50                  55                  60

Thr Glu Ser Gln Phe Glu Ala Ile Pro
65                  70


<210> SEQ ID NO 233
<211> LENGTH: 74
<212> TYPE: PRT
<213> ORGANISM: Ixodes scapularis

<400> SEQUENCE: 233

Leu Val Tyr Met Gly Ser Asp Gly Asn Ser Asp Phe Glu Glu Asp Lys
 1               5                  10                  15

Glu Ser Thr Gly Thr Asp Glu Asp Ser Asn Thr Gly Ser Ser Ala Ala
            20                  25                  30

Ala Lys Val Thr Glu Ala Leu Ile Ile Glu Ala Glu Glu Asn Cys Thr
        35                  40                  45

Ala His Ile Thr Gly Trp Thr Thr Glu Thr Pro Thr Thr Leu Glu Pro
    50                  55                  60

Thr Thr Glu Ser Gln Phe Glu Ala Ile Pro
65                  70


<210> SEQ ID NO 234
<211> LENGTH: 75
<212> TYPE: PRT
<213> ORGANISM: Ixodes scapularis

<400> SEQUENCE: 234

Tyr Leu Val Tyr Met Gly Ser Asp Gly Asn Ser Asp Phe Glu Glu Asp
 1               5                  10                  15

Lys Glu Ser Thr Gly Thr Asp Glu Asp Ser Asn Thr Gly Ser Ser Ala
            20                  25                  30

Ala Ala Lys Val Thr Glu Ala Leu Ile Ile Glu Ala Glu Glu Asn Cys
        35                  40                  45

Thr Ala His Ile Thr Gly Trp Thr Thr Glu Thr Pro Thr Thr Leu Glu
    50                  55                  60

Pro Thr Thr Glu Ser Gln Phe Glu Ala Ile Pro
65                  70                  75


<210> SEQ ID NO 235
<211> LENGTH: 76
```

-continued

<212> TYPE: PRT
<213> ORGANISM: Ixodes scapularis

<400> SEQUENCE: 235

Phe Tyr Leu Val Tyr Met Gly Ser Asp Gly Asn Ser Asp Phe Glu Glu
1 5 10 15

Asp Lys Glu Ser Thr Gly Thr Asp Glu Asp Ser Asn Thr Gly Ser Ser
20 25 30

Ala Ala Ala Lys Val Thr Glu Ala Leu Ile Ile Glu Ala Glu Glu Asn
35 40 45

Cys Thr Ala His Ile Thr Gly Trp Thr Thr Glu Thr Pro Thr Thr Leu
50 55 60

Glu Pro Thr Thr Glu Ser Gln Phe Glu Ala Ile Pro
65 70 75

<210> SEQ ID NO 236
<211> LENGTH: 77
<212> TYPE: PRT
<213> ORGANISM: Ixodes scapularis

<400> SEQUENCE: 236

Glu Phe Tyr Leu Val Tyr Met Gly Ser Asp Gly Asn Ser Asp Phe Glu
1 5 10 15

Glu Asp Lys Glu Ser Thr Gly Thr Asp Glu Asp Ser Asn Thr Gly Ser
20 25 30

Ser Ala Ala Ala Lys Val Thr Glu Ala Leu Ile Ile Glu Ala Glu Glu
35 40 45

Asn Cys Thr Ala His Ile Thr Gly Trp Thr Thr Glu Thr Pro Thr Thr
50 55 60

Leu Glu Pro Thr Thr Glu Ser Gln Phe Glu Ala Ile Pro
65 70 75

<210> SEQ ID NO 237
<211> LENGTH: 78
<212> TYPE: PRT
<213> ORGANISM: Ixodes scapularis

<400> SEQUENCE: 237

Gln Glu Phe Tyr Leu Val Tyr Met Gly Ser Asp Gly Asn Ser Asp Phe
1 5 10 15

Glu Glu Asp Lys Glu Ser Thr Gly Thr Asp Glu Asp Ser Asn Thr Gly
20 25 30

Ser Ser Ala Ala Ala Lys Val Thr Glu Ala Leu Ile Ile Glu Ala Glu
35 40 45

Glu Asn Cys Thr Ala His Ile Thr Gly Trp Thr Thr Glu Thr Pro Thr
50 55 60

Thr Leu Glu Pro Thr Thr Glu Ser Gln Phe Glu Ala Ile Pro
65 70 75

<210> SEQ ID NO 238
<211> LENGTH: 79
<212> TYPE: PRT
<213> ORGANISM: Ixodes scapularis

<400> SEQUENCE: 238

Pro Gln Glu Phe Tyr Leu Val Tyr Met Gly Ser Asp Gly Asn Ser Asp
1 5 10 15

Phe Glu Glu Asp Lys Glu Ser Thr Gly Thr Asp Glu Asp Ser Asn Thr
20 25 30

-continued

```
Gly Ser Ser Ala Ala Ala Lys Val Thr Glu Ala Leu Ile Ile Glu Ala
        35                  40                  45

Glu Glu Asn Cys Thr Ala His Ile Thr Gly Trp Thr Thr Glu Thr Pro
    50                  55                  60

Thr Thr Leu Glu Pro Thr Thr Glu Ser Gln Phe Glu Ala Ile Pro
65                  70                  75
```

<210> SEQ ID NO 239
<211> LENGTH: 80
<212> TYPE: PRT
<213> ORGANISM: Ixodes scapularis

<400> SEQUENCE: 239

```
Met Pro Gln Glu Phe Tyr Leu Val Tyr Met Gly Ser Asp Gly Asn Ser
 1               5                  10                  15

Asp Phe Glu Glu Asp Lys Glu Ser Thr Gly Thr Asp Glu Asp Ser Asn
            20                  25                  30

Thr Gly Ser Ser Ala Ala Ala Lys Val Thr Glu Ala Leu Ile Ile Glu
        35                  40                  45

Ala Glu Glu Asn Cys Thr Ala His Ile Thr Gly Trp Thr Thr Glu Thr
    50                  55                  60

Pro Thr Thr Leu Glu Pro Thr Thr Glu Ser Gln Phe Glu Ala Ile Pro
65                  70                  75                  80
```

<210> SEQ ID NO 240
<211> LENGTH: 81
<212> TYPE: PRT
<213> ORGANISM: Ixodes scapularis

<400> SEQUENCE: 240

```
Ala Met Pro Gln Glu Phe Tyr Leu Val Tyr Met Gly Ser Asp Gly Asn
 1               5                  10                  15

Ser Asp Phe Glu Glu Asp Lys Glu Ser Thr Gly Thr Asp Glu Asp Ser
            20                  25                  30

Asn Thr Gly Ser Ser Ala Ala Ala Lys Val Thr Glu Ala Leu Ile Ile
        35                  40                  45

Glu Ala Glu Glu Asn Cys Thr Ala His Ile Thr Gly Trp Thr Thr Glu
    50                  55                  60

Thr Pro Thr Thr Leu Glu Pro Thr Thr Glu Ser Gln Phe Glu Ala Ile
65                  70                  75                  80

Pro
```

<210> SEQ ID NO 241
<211> LENGTH: 82
<212> TYPE: PRT
<213> ORGANISM: Ixodes scapularis

<400> SEQUENCE: 241

```
Val Ala Met Pro Gln Glu Phe Tyr Leu Val Tyr Met Gly Ser Asp Gly
 1               5                  10                  15

Asn Ser Asp Phe Glu Glu Asp Lys Glu Ser Thr Gly Thr Asp Glu Asp
            20                  25                  30

Ser Asn Thr Gly Ser Ser Ala Ala Ala Lys Val Thr Glu Ala Leu Ile
        35                  40                  45

Ile Glu Ala Glu Glu Asn Cys Thr Ala His Ile Thr Gly Trp Thr Thr
    50                  55                  60

Glu Thr Pro Thr Thr Leu Glu Pro Thr Thr Glu Ser Gln Phe Glu Ala
```

-continued

```
65                  70                  75                  80

Ile Pro


<210> SEQ ID NO 242
<211> LENGTH: 83
<212> TYPE: PRT
<213> ORGANISM: Ixodes scapularis

<400> SEQUENCE: 242

Thr Val Ala Met Pro Gln Glu Phe Tyr Leu Val Tyr Met Gly Ser Asp
 1               5                  10                  15

Gly Asn Ser Asp Phe Glu Glu Asp Lys Glu Ser Thr Gly Thr Asp Glu
            20                  25                  30

Asp Ser Asn Thr Gly Ser Ser Ala Ala Ala Lys Val Thr Glu Ala Leu
        35                  40                  45

Ile Ile Glu Ala Glu Glu Asn Cys Thr Ala His Ile Thr Gly Trp Thr
    50                  55                  60

Thr Glu Thr Pro Thr Thr Leu Glu Pro Thr Thr Glu Ser Gln Phe Glu
65                  70                  75                  80

Ala Ile Pro


<210> SEQ ID NO 243
<211> LENGTH: 84
<212> TYPE: PRT
<213> ORGANISM: Ixodes scapularis

<400> SEQUENCE: 243

Phe Thr Val Ala Met Pro Gln Glu Phe Tyr Leu Val Tyr Met Gly Ser
 1               5                  10                  15

Asp Gly Asn Ser Asp Phe Glu Glu Asp Lys Glu Ser Thr Gly Thr Asp
            20                  25                  30

Glu Asp Ser Asn Thr Gly Ser Ser Ala Ala Ala Lys Val Thr Glu Ala
        35                  40                  45

Leu Ile Ile Glu Ala Glu Glu Asn Cys Thr Ala His Ile Thr Gly Trp
    50                  55                  60

Thr Thr Glu Thr Pro Thr Thr Leu Glu Pro Thr Thr Glu Ser Gln Phe
65                  70                  75                  80

Glu Ala Ile Pro


<210> SEQ ID NO 244
<211> LENGTH: 85
<212> TYPE: PRT
<213> ORGANISM: Ixodes scapularis

<400> SEQUENCE: 244

Asn Phe Thr Val Ala Met Pro Gln Glu Phe Tyr Leu Val Tyr Met Gly
 1               5                  10                  15

Ser Asp Gly Asn Ser Asp Phe Glu Glu Asp Lys Glu Ser Thr Gly Thr
            20                  25                  30

Asp Glu Asp Ser Asn Thr Gly Ser Ser Ala Ala Ala Lys Val Thr Glu
        35                  40                  45

Ala Leu Ile Ile Glu Ala Glu Glu Asn Cys Thr Ala His Ile Thr Gly
    50                  55                  60

Trp Thr Thr Glu Thr Pro Thr Thr Leu Glu Pro Thr Thr Glu Ser Gln
65                  70                  75                  80

Phe Glu Ala Ile Pro
                85
```

-continued

<210> SEQ ID NO 245
<211> LENGTH: 86
<212> TYPE: PRT
<213> ORGANISM: Ixodes scapularis

<400> SEQUENCE: 245

```
Cys Asn Phe Thr Val Ala Met Pro Gln Glu Phe Tyr Leu Val Tyr Met
 1               5                  10                  15

Gly Ser Asp Gly Asn Ser Asp Phe Glu Glu Asp Lys Glu Ser Thr Gly
            20                  25                  30

Thr Asp Glu Asp Ser Asn Thr Gly Ser Ser Ala Ala Ala Lys Val Thr
        35                  40                  45

Glu Ala Leu Ile Ile Glu Ala Glu Glu Asn Cys Thr Ala His Ile Thr
    50                  55                  60

Gly Trp Thr Thr Glu Thr Pro Thr Thr Leu Glu Pro Thr Thr Glu Ser
65                  70                  75                  80

Gln Phe Glu Ala Ile Pro
                85
```

<210> SEQ ID NO 246
<211> LENGTH: 87
<212> TYPE: PRT
<213> ORGANISM: Ixodes scapularis

<400> SEQUENCE: 246

```
Ile Cys Asn Phe Thr Val Ala Met Pro Gln Glu Phe Tyr Leu Val Tyr
 1               5                  10                  15

Met Gly Ser Asp Gly Asn Ser Asp Phe Glu Glu Asp Lys Glu Ser Thr
            20                  25                  30

Gly Thr Asp Glu Asp Ser Asn Thr Gly Ser Ser Ala Ala Ala Lys Val
        35                  40                  45

Thr Glu Ala Leu Ile Ile Glu Ala Glu Glu Asn Cys Thr Ala His Ile
    50                  55                  60

Thr Gly Trp Thr Thr Glu Thr Pro Thr Thr Leu Glu Pro Thr Thr Glu
65                  70                  75                  80

Ser Gln Phe Glu Ala Ile Pro
                85
```

<210> SEQ ID NO 247
<211> LENGTH: 88
<212> TYPE: PRT
<213> ORGANISM: Ixodes scapularis

<400> SEQUENCE: 247

```
Leu Ile Cys Asn Phe Thr Val Ala Met Pro Gln Glu Phe Tyr Leu Val
 1               5                  10                  15

Tyr Met Gly Ser Asp Gly Asn Ser Asp Phe Glu Glu Asp Lys Glu Ser
            20                  25                  30

Thr Gly Thr Asp Glu Asp Ser Asn Thr Gly Ser Ser Ala Ala Ala Lys
        35                  40                  45

Val Thr Glu Ala Leu Ile Ile Glu Ala Glu Glu Asn Cys Thr Ala His
    50                  55                  60

Ile Thr Gly Trp Thr Thr Glu Thr Pro Thr Thr Leu Glu Pro Thr Thr
65                  70                  75                  80

Glu Ser Gln Phe Glu Ala Ile Pro
                85
```

-continued

<210> SEQ ID NO 248
<211> LENGTH: 89
<212> TYPE: PRT
<213> ORGANISM: Ixodes scapularis

<400> SEQUENCE: 248

```
Lys Leu Ile Cys Asn Phe Thr Val Ala Met Pro Gln Glu Phe Tyr Leu
 1               5                  10                  15

Val Tyr Met Gly Ser Asp Gly Asn Ser Asp Phe Glu Glu Asp Lys Glu
            20                  25                  30

Ser Thr Gly Thr Asp Glu Asp Ser Asn Thr Gly Ser Ser Ala Ala Ala
        35                  40                  45

Lys Val Thr Glu Ala Leu Ile Ile Glu Ala Glu Glu Asn Cys Thr Ala
    50                  55                  60

His Ile Thr Gly Trp Thr Thr Glu Thr Pro Thr Thr Leu Glu Pro Thr
65                  70                  75                  80

Thr Glu Ser Gln Phe Glu Ala Ile Pro
                85
```

<210> SEQ ID NO 249
<211> LENGTH: 90
<212> TYPE: PRT
<213> ORGANISM: Ixodes scapularis

<400> SEQUENCE: 249

```
Val Lys Leu Ile Cys Asn Phe Thr Val Ala Met Pro Gln Glu Phe Tyr
 1               5                  10                  15

Leu Val Tyr Met Gly Ser Asp Gly Asn Ser Asp Phe Glu Glu Asp Lys
            20                  25                  30

Glu Ser Thr Gly Thr Asp Glu Asp Ser Asn Thr Gly Ser Ser Ala Ala
        35                  40                  45

Ala Lys Val Thr Glu Ala Leu Ile Ile Glu Ala Glu Glu Asn Cys Thr
    50                  55                  60

Ala His Ile Thr Gly Trp Thr Thr Glu Thr Pro Thr Thr Leu Glu Pro
65                  70                  75                  80

Thr Thr Glu Ser Gln Phe Glu Ala Ile Pro
                85                  90
```

<210> SEQ ID NO 250
<211> LENGTH: 91
<212> TYPE: PRT
<213> ORGANISM: Ixodes scapularis

<400> SEQUENCE: 250

```
Phe Val Lys Leu Ile Cys Asn Phe Thr Val Ala Met Pro Gln Glu Phe
 1               5                  10                  15

Tyr Leu Val Tyr Met Gly Ser Asp Gly Asn Ser Asp Phe Glu Glu Asp
            20                  25                  30

Lys Glu Ser Thr Gly Thr Asp Glu Asp Ser Asn Thr Gly Ser Ser Ala
        35                  40                  45

Ala Ala Lys Val Thr Glu Ala Leu Ile Ile Glu Ala Glu Glu Asn Cys
    50                  55                  60

Thr Ala His Ile Thr Gly Trp Thr Thr Glu Thr Pro Thr Thr Leu Glu
65                  70                  75                  80

Pro Thr Thr Glu Ser Gln Phe Glu Ala Ile Pro
                85                  90
```

-continued

<210> SEQ ID NO 251
<211> LENGTH: 92
<212> TYPE: PRT
<213> ORGANISM: Ixodes scapularis

<400> SEQUENCE: 251

```
Gln Phe Val Lys Leu Ile Cys Asn Phe Thr Val Ala Met Pro Gln Glu
 1               5                  10                  15

Phe Tyr Leu Val Tyr Met Gly Ser Asp Gly Asn Ser Asp Phe Glu Glu
            20                  25                  30

Asp Lys Glu Ser Thr Gly Thr Asp Glu Asp Ser Asn Thr Gly Ser Ser
        35                  40                  45

Ala Ala Ala Lys Val Thr Glu Ala Leu Ile Ile Glu Ala Glu Glu Asn
    50                  55                  60

Cys Thr Ala His Ile Thr Gly Trp Thr Thr Glu Thr Pro Thr Thr Leu
65                  70                  75                  80

Glu Pro Thr Thr Glu Ser Gln Phe Glu Ala Ile Pro
                85                  90
```

<210> SEQ ID NO 252
<211> LENGTH: 93
<212> TYPE: PRT
<213> ORGANISM: Ixodes scapularis

<400> SEQUENCE: 252

```
Pro Gln Phe Val Lys Leu Ile Cys Asn Phe Thr Val Ala Met Pro Gln
 1               5                  10                  15

Glu Phe Tyr Leu Val Tyr Met Gly Ser Asp Gly Asn Ser Asp Phe Glu
            20                  25                  30

Glu Asp Lys Glu Ser Thr Gly Thr Asp Glu Asp Ser Asn Thr Gly Ser
        35                  40                  45

Ser Ala Ala Ala Lys Val Thr Glu Ala Leu Ile Ile Glu Ala Glu Glu
    50                  55                  60

Asn Cys Thr Ala His Ile Thr Gly Trp Thr Thr Glu Thr Pro Thr Thr
65                  70                  75                  80

Leu Glu Pro Thr Thr Glu Ser Gln Phe Glu Ala Ile Pro
                85                  90
```

<210> SEQ ID NO 253
<211> LENGTH: 94
<212> TYPE: PRT
<213> ORGANISM: Ixodes scapularis

<400> SEQUENCE: 253

```
Ile Pro Gln Phe Val Lys Leu Ile Cys Asn Phe Thr Val Ala Met Pro
 1               5                  10                  15

Gln Glu Phe Tyr Leu Val Tyr Met Gly Ser Asp Gly Asn Ser Asp Phe
            20                  25                  30

Glu Glu Asp Lys Glu Ser Thr Gly Thr Asp Glu Asp Ser Asn Thr Gly
        35                  40                  45

Ser Ser Ala Ala Ala Lys Val Thr Glu Ala Leu Ile Ile Glu Ala Glu
    50                  55                  60

Glu Asn Cys Thr Ala His Ile Thr Gly Trp Thr Thr Glu Thr Pro Thr
65                  70                  75                  80

Thr Leu Glu Pro Thr Thr Glu Ser Gln Phe Glu Ala Ile Pro
                85                  90
```

<210> SEQ ID NO 254

-continued

```
<211> LENGTH: 95
<212> TYPE: PRT
<213> ORGANISM: Ixodes scapularis

<400> SEQUENCE: 254

Thr Ile Pro Gln Phe Val Lys Leu Ile Cys Asn Phe Thr Val Ala Met
 1              5                   10                  15

Pro Gln Glu Phe Tyr Leu Val Tyr Met Gly Ser Asp Gly Asn Ser Asp
            20                  25                  30

Phe Glu Glu Asp Lys Glu Ser Thr Gly Thr Asp Glu Asp Ser Asn Thr
        35                  40                  45

Gly Ser Ser Ala Ala Ala Lys Val Thr Glu Ala Leu Ile Ile Glu Ala
    50                  55                  60

Glu Glu Asn Cys Thr Ala His Ile Thr Gly Trp Thr Thr Glu Thr Pro
65                  70                  75                  80

Thr Thr Leu Glu Pro Thr Thr Glu Ser Gln Phe Glu Ala Ile Pro
                85                  90                  95


<210> SEQ ID NO 255
<211> LENGTH: 96
<212> TYPE: PRT
<213> ORGANISM: Ixodes scapularis

<400> SEQUENCE: 255

Lys Thr Ile Pro Gln Phe Val Lys Leu Ile Cys Asn Phe Thr Val Ala
 1              5                   10                  15

Met Pro Gln Glu Phe Tyr Leu Val Tyr Met Gly Ser Asp Gly Asn Ser
            20                  25                  30

Asp Phe Glu Glu Asp Lys Glu Ser Thr Gly Thr Asp Glu Asp Ser Asn
        35                  40                  45

Thr Gly Ser Ser Ala Ala Ala Lys Val Thr Glu Ala Leu Ile Ile Glu
    50                  55                  60

Ala Glu Glu Asn Cys Thr Ala His Ile Thr Gly Trp Thr Thr Glu Thr
65                  70                  75                  80

Pro Thr Thr Leu Glu Pro Thr Thr Glu Ser Gln Phe Glu Ala Ile Pro
                85                  90                  95


<210> SEQ ID NO 256
<211> LENGTH: 97
<212> TYPE: PRT
<213> ORGANISM: Ixodes scapularis

<400> SEQUENCE: 256

Asn Lys Thr Ile Pro Gln Phe Val Lys Leu Ile Cys Asn Phe Thr Val
 1              5                   10                  15

Ala Met Pro Gln Glu Phe Tyr Leu Val Tyr Met Gly Ser Asp Gly Asn
            20                  25                  30

Ser Asp Phe Glu Glu Asp Lys Glu Ser Thr Gly Thr Asp Glu Asp Ser
        35                  40                  45

Asn Thr Gly Ser Ser Ala Ala Ala Lys Val Thr Glu Ala Leu Ile Ile
    50                  55                  60

Glu Ala Glu Glu Asn Cys Thr Ala His Ile Thr Gly Trp Thr Thr Glu
65                  70                  75                  80

Thr Pro Thr Thr Leu Glu Pro Thr Thr Glu Ser Gln Phe Glu Ala Ile
                85                  90                  95

Pro
```

-continued

<210> SEQ ID NO 257
<211> LENGTH: 98
<212> TYPE: PRT
<213> ORGANISM: Ixodes scapularis

<400> SEQUENCE: 257

```
Ile Asn Lys Thr Ile Pro Gln Phe Val Lys Leu Ile Cys Asn Phe Thr
 1               5                  10                  15

Val Ala Met Pro Gln Glu Phe Tyr Leu Val Tyr Met Gly Ser Asp Gly
            20                  25                  30

Asn Ser Asp Phe Glu Glu Asp Lys Glu Ser Thr Gly Thr Asp Glu Asp
        35                  40                  45

Ser Asn Thr Gly Ser Ser Ala Ala Ala Lys Val Thr Glu Ala Leu Ile
    50                  55                  60

Ile Glu Ala Glu Glu Asn Cys Thr Ala His Ile Thr Gly Trp Thr Thr
65                  70                  75                  80

Glu Thr Pro Thr Thr Leu Glu Pro Thr Thr Glu Ser Gln Phe Glu Ala
                85                  90                  95

Ile Pro
```

<210> SEQ ID NO 258
<211> LENGTH: 99
<212> TYPE: PRT
<213> ORGANISM: Ixodes scapularis

<400> SEQUENCE: 258

```
Arg Ile Asn Lys Thr Ile Pro Gln Phe Val Lys Leu Ile Cys Asn Phe
 1               5                  10                  15

Thr Val Ala Met Pro Gln Glu Phe Tyr Leu Val Tyr Met Gly Ser Asp
            20                  25                  30

Gly Asn Ser Asp Phe Glu Glu Asp Lys Glu Ser Thr Gly Thr Asp Glu
        35                  40                  45

Asp Ser Asn Thr Gly Ser Ser Ala Ala Ala Lys Val Thr Glu Ala Leu
    50                  55                  60

Ile Ile Glu Ala Glu Glu Asn Cys Thr Ala His Ile Thr Gly Trp Thr
65                  70                  75                  80

Thr Glu Thr Pro Thr Thr Leu Glu Pro Thr Thr Glu Ser Gln Phe Glu
                85                  90                  95

Ala Ile Pro
```

<210> SEQ ID NO 259
<211> LENGTH: 100
<212> TYPE: PRT
<213> ORGANISM: Ixodes scapularis

<400> SEQUENCE: 259

```
His Arg Ile Asn Lys Thr Ile Pro Gln Phe Val Lys Leu Ile Cys Asn
 1               5                  10                  15

Phe Thr Val Ala Met Pro Gln Glu Phe Tyr Leu Val Tyr Met Gly Ser
            20                  25                  30

Asp Gly Asn Ser Asp Phe Glu Glu Asp Lys Glu Ser Thr Gly Thr Asp
        35                  40                  45

Glu Asp Ser Asn Thr Gly Ser Ser Ala Ala Ala Lys Val Thr Glu Ala
    50                  55                  60

Leu Ile Ile Glu Ala Glu Glu Asn Cys Thr Ala His Ile Thr Gly Trp
65                  70                  75                  80

Thr Thr Glu Thr Pro Thr Thr Leu Glu Pro Thr Thr Glu Ser Gln Phe
```

-continued

```
                85                  90                  95

Glu Ala Ile Pro
            100


<210> SEQ ID NO 260
<211> LENGTH: 101
<212> TYPE: PRT
<213> ORGANISM: Ixodes scapularis

<400> SEQUENCE: 260

Arg His Arg Ile Asn Lys Thr Ile Pro Gln Phe Val Lys Leu Ile Cys
 1               5                  10                  15

Asn Phe Thr Val Ala Met Pro Gln Glu Phe Tyr Leu Val Tyr Met Gly
            20                  25                  30

Ser Asp Gly Asn Ser Asp Phe Glu Glu Asp Lys Glu Ser Thr Gly Thr
        35                  40                  45

Asp Glu Asp Ser Asn Thr Gly Ser Ser Ala Ala Ala Lys Val Thr Glu
    50                  55                  60

Ala Leu Ile Ile Glu Ala Glu Glu Asn Cys Thr Ala His Ile Thr Gly
65                  70                  75                  80

Trp Thr Thr Glu Thr Pro Thr Thr Leu Glu Pro Thr Thr Glu Ser Gln
                85                  90                  95

Phe Glu Ala Ile Pro
            100


<210> SEQ ID NO 261
<211> LENGTH: 102
<212> TYPE: PRT
<213> ORGANISM: Ixodes scapularis

<400> SEQUENCE: 261

Ile Arg His Arg Ile Asn Lys Thr Ile Pro Gln Phe Val Lys Leu Ile
 1               5                  10                  15

Cys Asn Phe Thr Val Ala Met Pro Gln Glu Phe Tyr Leu Val Tyr Met
            20                  25                  30

Gly Ser Asp Gly Asn Ser Asp Phe Glu Glu Asp Lys Glu Ser Thr Gly
        35                  40                  45

Thr Asp Glu Asp Ser Asn Thr Gly Ser Ser Ala Ala Ala Lys Val Thr
    50                  55                  60

Glu Ala Leu Ile Ile Glu Ala Glu Glu Asn Cys Thr Ala His Ile Thr
65                  70                  75                  80

Gly Trp Thr Thr Glu Thr Pro Thr Thr Leu Glu Pro Thr Thr Glu Ser
                85                  90                  95

Gln Phe Glu Ala Ile Pro
            100


<210> SEQ ID NO 262
<211> LENGTH: 103
<212> TYPE: PRT
<213> ORGANISM: Ixodes scapularis

<400> SEQUENCE: 262

Gly Ile Arg His Arg Ile Asn Lys Thr Ile Pro Gln Phe Val Lys Leu
 1               5                  10                  15

Ile Cys Asn Phe Thr Val Ala Met Pro Gln Glu Phe Tyr Leu Val Tyr
            20                  25                  30

Met Gly Ser Asp Gly Asn Ser Asp Phe Glu Glu Asp Lys Glu Ser Thr
        35                  40                  45
```

-continued

```
Gly Thr Asp Glu Asp Ser Asn Thr Gly Ser Ser Ala Ala Ala Lys Val
    50                  55                  60

Thr Glu Ala Leu Ile Ile Glu Ala Glu Glu Asn Cys Thr Ala His Ile
65                  70                  75                  80

Thr Gly Trp Thr Thr Glu Thr Pro Thr Thr Leu Glu Pro Thr Thr Glu
                85                  90                  95

Ser Gln Phe Glu Ala Ile Pro
            100


<210> SEQ ID NO 263
<211> LENGTH: 104
<212> TYPE: PRT
<213> ORGANISM: Ixodes scapularis

<400> SEQUENCE: 263

Glu Gly Ile Arg His Arg Ile Asn Lys Thr Ile Pro Gln Phe Val Lys
 1               5                  10                  15

Leu Ile Cys Asn Phe Thr Val Ala Met Pro Gln Glu Phe Tyr Leu Val
            20                  25                  30

Tyr Met Gly Ser Asp Gly Asn Ser Asp Phe Glu Glu Asp Lys Glu Ser
        35                  40                  45

Thr Gly Thr Asp Glu Asp Ser Asn Thr Gly Ser Ser Ala Ala Ala Lys
    50                  55                  60

Val Thr Glu Ala Leu Ile Ile Glu Ala Glu Glu Asn Cys Thr Ala His
65                  70                  75                  80

Ile Thr Gly Trp Thr Thr Glu Thr Pro Thr Thr Leu Glu Pro Thr Thr
                85                  90                  95

Glu Ser Gln Phe Glu Ala Ile Pro
            100


<210> SEQ ID NO 264
<211> LENGTH: 105
<212> TYPE: PRT
<213> ORGANISM: Ixodes scapularis

<400> SEQUENCE: 264

Trp Glu Gly Ile Arg His Arg Ile Asn Lys Thr Ile Pro Gln Phe Val
 1               5                  10                  15

Lys Leu Ile Cys Asn Phe Thr Val Ala Met Pro Gln Glu Phe Tyr Leu
            20                  25                  30

Val Tyr Met Gly Ser Asp Gly Asn Ser Asp Phe Glu Glu Asp Lys Glu
        35                  40                  45

Ser Thr Gly Thr Asp Glu Asp Ser Asn Thr Gly Ser Ser Ala Ala Ala
    50                  55                  60

Lys Val Thr Glu Ala Leu Ile Ile Glu Ala Glu Glu Asn Cys Thr Ala
65                  70                  75                  80

His Ile Thr Gly Trp Thr Thr Glu Thr Pro Thr Thr Leu Glu Pro Thr
                85                  90                  95

Thr Glu Ser Gln Phe Glu Ala Ile Pro
            100                 105


<210> SEQ ID NO 265
<211> LENGTH: 106
<212> TYPE: PRT
<213> ORGANISM: Ixodes scapularis

<400> SEQUENCE: 265
```

-continued

```
Thr Trp Glu Gly Ile Arg His Arg Ile Asn Lys Thr Ile Pro Gln Phe
 1               5                  10                  15

Val Lys Leu Ile Cys Asn Phe Thr Val Ala Met Pro Gln Glu Phe Tyr
            20                  25                  30

Leu Val Tyr Met Gly Ser Asp Gly Asn Ser Asp Phe Glu Glu Asp Lys
        35                  40                  45

Glu Ser Thr Gly Thr Asp Glu Asp Ser Asn Thr Gly Ser Ser Ala Ala
    50                  55                  60

Ala Lys Val Thr Glu Ala Leu Ile Ile Glu Ala Glu Glu Asn Cys Thr
65                  70                  75                  80

Ala His Ile Thr Gly Trp Thr Thr Glu Thr Pro Thr Thr Leu Glu Pro
                85                  90                  95

Thr Thr Glu Ser Gln Phe Glu Ala Ile Pro
            100                 105


<210> SEQ ID NO 266
<211> LENGTH: 107
<212> TYPE: PRT
<213> ORGANISM: Ixodes scapularis

<400> SEQUENCE: 266

Ala Thr Trp Glu Gly Ile Arg His Arg Ile Asn Lys Thr Ile Pro Gln
 1               5                  10                  15

Phe Val Lys Leu Ile Cys Asn Phe Thr Val Ala Met Pro Gln Glu Phe
            20                  25                  30

Tyr Leu Val Tyr Met Gly Ser Asp Gly Asn Ser Asp Phe Glu Glu Asp
        35                  40                  45

Lys Glu Ser Thr Gly Thr Asp Glu Asp Ser Asn Thr Gly Ser Ser Ala
    50                  55                  60

Ala Ala Lys Val Thr Glu Ala Leu Ile Ile Glu Ala Glu Glu Asn Cys
65                  70                  75                  80

Thr Ala His Ile Thr Gly Trp Thr Thr Glu Thr Pro Thr Thr Leu Glu
                85                  90                  95

Pro Thr Thr Glu Ser Gln Phe Glu Ala Ile Pro
            100                 105


<210> SEQ ID NO 267
<211> LENGTH: 108
<212> TYPE: PRT
<213> ORGANISM: Ixodes scapularis

<400> SEQUENCE: 267

Asn Ala Thr Trp Glu Gly Ile Arg His Arg Ile Asn Lys Thr Ile Pro
 1               5                  10                  15

Gln Phe Val Lys Leu Ile Cys Asn Phe Thr Val Ala Met Pro Gln Glu
            20                  25                  30

Phe Tyr Leu Val Tyr Met Gly Ser Asp Gly Asn Ser Asp Phe Glu Glu
        35                  40                  45

Asp Lys Glu Ser Thr Gly Thr Asp Glu Asp Ser Asn Thr Gly Ser Ser
    50                  55                  60

Ala Ala Ala Lys Val Thr Glu Ala Leu Ile Ile Glu Ala Glu Glu Asn
65                  70                  75                  80

Cys Thr Ala His Ile Thr Gly Trp Thr Thr Glu Thr Pro Thr Thr Leu
                85                  90                  95

Glu Pro Thr Thr Glu Ser Gln Phe Glu Ala Ile Pro
            100                 105
```

-continued

<210> SEQ ID NO 268
<211> LENGTH: 109
<212> TYPE: PRT
<213> ORGANISM: Ixodes scapularis

<400> SEQUENCE: 268

```
Val Asn Ala Thr Trp Glu Gly Ile Arg His Arg Ile Asn Lys Thr Ile
 1               5                  10                  15

Pro Gln Phe Val Lys Leu Ile Cys Asn Phe Thr Val Ala Met Pro Gln
            20                  25                  30

Glu Phe Tyr Leu Val Tyr Met Gly Ser Asp Gly Asn Ser Asp Phe Glu
        35                  40                  45

Glu Asp Lys Glu Ser Thr Gly Thr Asp Glu Asp Ser Asn Thr Gly Ser
    50                  55                  60

Ser Ala Ala Ala Lys Val Thr Glu Ala Leu Ile Ile Glu Ala Glu Glu
65                  70                  75                  80

Asn Cys Thr Ala His Ile Thr Gly Trp Thr Thr Glu Thr Pro Thr Thr
                85                  90                  95

Leu Glu Pro Thr Thr Glu Ser Gln Phe Glu Ala Ile Pro
            100                 105
```

<210> SEQ ID NO 269
<211> LENGTH: 110
<212> TYPE: PRT
<213> ORGANISM: Ixodes scapularis

<400> SEQUENCE: 269

```
Val Val Asn Ala Thr Trp Glu Gly Ile Arg His Arg Ile Asn Lys Thr
 1               5                  10                  15

Ile Pro Gln Phe Val Lys Leu Ile Cys Asn Phe Thr Val Ala Met Pro
            20                  25                  30

Gln Glu Phe Tyr Leu Val Tyr Met Gly Ser Asp Gly Asn Ser Asp Phe
        35                  40                  45

Glu Glu Asp Lys Glu Ser Thr Gly Thr Asp Glu Asp Ser Asn Thr Gly
    50                  55                  60

Ser Ser Ala Ala Ala Lys Val Thr Glu Ala Leu Ile Ile Glu Ala Glu
65                  70                  75                  80

Glu Asn Cys Thr Ala His Ile Thr Gly Trp Thr Thr Glu Thr Pro Thr
                85                  90                  95

Thr Leu Glu Pro Thr Thr Glu Ser Gln Phe Glu Ala Ile Pro
            100                 105                 110
```

<210> SEQ ID NO 270
<211> LENGTH: 111
<212> TYPE: PRT
<213> ORGANISM: Ixodes scapularis

<400> SEQUENCE: 270

```
Pro Val Val Asn Ala Thr Trp Glu Gly Ile Arg His Arg Ile Asn Lys
 1               5                  10                  15

Thr Ile Pro Gln Phe Val Lys Leu Ile Cys Asn Phe Thr Val Ala Met
            20                  25                  30

Pro Gln Glu Phe Tyr Leu Val Tyr Met Gly Ser Asp Gly Asn Ser Asp
        35                  40                  45

Phe Glu Glu Asp Lys Glu Ser Thr Gly Thr Asp Glu Asp Ser Asn Thr
    50                  55                  60

Gly Ser Ser Ala Ala Ala Lys Val Thr Glu Ala Leu Ile Ile Glu Ala
```

-continued

```
65                  70                  75                  80

Glu Glu Asn Cys Thr Ala His Ile Thr Gly Trp Thr Thr Glu Thr Pro
                85                  90                  95

Thr Thr Leu Glu Pro Thr Thr Glu Ser Gln Phe Glu Ala Ile Pro
            100                 105                 110


<210> SEQ ID NO 271
<211> LENGTH: 112
<212> TYPE: PRT
<213> ORGANISM: Ixodes scapularis

<400> SEQUENCE: 271

Pro Pro Val Val Asn Ala Thr Trp Glu Gly Ile Arg His Arg Ile Asn
 1               5                  10                  15

Lys Thr Ile Pro Gln Phe Val Lys Leu Ile Cys Asn Phe Thr Val Ala
            20                  25                  30

Met Pro Gln Glu Phe Tyr Leu Val Tyr Met Gly Ser Asp Gly Asn Ser
        35                  40                  45

Asp Phe Glu Glu Asp Lys Glu Ser Thr Gly Thr Asp Glu Asp Ser Asn
    50                  55                  60

Thr Gly Ser Ser Ala Ala Ala Lys Val Thr Glu Ala Leu Ile Ile Glu
65                  70                  75                  80

Ala Glu Glu Asn Cys Thr Ala His Ile Thr Gly Trp Thr Thr Glu Thr
                85                  90                  95

Pro Thr Thr Leu Glu Pro Thr Thr Glu Ser Gln Phe Glu Ala Ile Pro
            100                 105                 110


<210> SEQ ID NO 272
<211> LENGTH: 113
<212> TYPE: PRT
<213> ORGANISM: Ixodes scapularis

<400> SEQUENCE: 272

Leu Pro Pro Val Val Asn Ala Thr Trp Glu Gly Ile Arg His Arg Ile
 1               5                  10                  15

Asn Lys Thr Ile Pro Gln Phe Val Lys Leu Ile Cys Asn Phe Thr Val
            20                  25                  30

Ala Met Pro Gln Glu Phe Tyr Leu Val Tyr Met Gly Ser Asp Gly Asn
        35                  40                  45

Ser Asp Phe Glu Glu Asp Lys Glu Ser Thr Gly Thr Asp Glu Asp Ser
    50                  55                  60

Asn Thr Gly Ser Ser Ala Ala Ala Lys Val Thr Glu Ala Leu Ile Ile
65                  70                  75                  80

Glu Ala Glu Glu Asn Cys Thr Ala His Ile Thr Gly Trp Thr Thr Glu
                85                  90                  95

Thr Pro Thr Thr Leu Glu Pro Thr Thr Glu Ser Gln Phe Glu Ala Ile
            100                 105                 110

Pro


<210> SEQ ID NO 273
<211> LENGTH: 114
<212> TYPE: PRT
<213> ORGANISM: Ixodes scapularis

<400> SEQUENCE: 273

His Leu Pro Pro Val Val Asn Ala Thr Trp Glu Gly Ile Arg His Arg
 1               5                  10                  15
```

-continued

```
Ile Asn Lys Thr Ile Pro Gln Phe Val Lys Leu Ile Cys Asn Phe Thr
            20                  25                  30

Val Ala Met Pro Gln Glu Phe Tyr Leu Val Tyr Met Gly Ser Asp Gly
        35                  40                  45

Asn Ser Asp Phe Glu Glu Asp Lys Glu Ser Thr Gly Thr Asp Glu Asp
    50                  55                  60

Ser Asn Thr Gly Ser Ser Ala Ala Ala Lys Val Thr Glu Ala Leu Ile
65                  70                  75                  80

Ile Glu Ala Glu Glu Asn Cys Thr Ala His Ile Thr Gly Trp Thr Thr
                85                  90                  95

Glu Thr Pro Thr Thr Leu Glu Pro Thr Thr Glu Ser Gln Phe Glu Ala
            100                 105                 110

Ile Pro


<210> SEQ ID NO 274
<211> LENGTH: 115
<212> TYPE: PRT
<213> ORGANISM: Ixodes scapularis

<400> SEQUENCE: 274

Asn His Leu Pro Pro Val Val Asn Ala Thr Trp Glu Gly Ile Arg His
 1               5                  10                  15

Arg Ile Asn Lys Thr Ile Pro Gln Phe Val Lys Leu Ile Cys Asn Phe
            20                  25                  30

Thr Val Ala Met Pro Gln Glu Phe Tyr Leu Val Tyr Met Gly Ser Asp
        35                  40                  45

Gly Asn Ser Asp Phe Glu Glu Asp Lys Glu Ser Thr Gly Thr Asp Glu
    50                  55                  60

Asp Ser Asn Thr Gly Ser Ser Ala Ala Ala Lys Val Thr Glu Ala Leu
65                  70                  75                  80

Ile Ile Glu Ala Glu Glu Asn Cys Thr Ala His Ile Thr Gly Trp Thr
                85                  90                  95

Thr Glu Thr Pro Thr Thr Leu Glu Pro Thr Thr Glu Ser Gln Phe Glu
            100                 105                 110

Ala Ile Pro
        115


<210> SEQ ID NO 275
<211> LENGTH: 116
<212> TYPE: PRT
<213> ORGANISM: Ixodes scapularis

<400> SEQUENCE: 275

Leu Asn His Leu Pro Pro Val Val Asn Ala Thr Trp Glu Gly Ile Arg
 1               5                  10                  15

His Arg Ile Asn Lys Thr Ile Pro Gln Phe Val Lys Leu Ile Cys Asn
            20                  25                  30

Phe Thr Val Ala Met Pro Gln Glu Phe Tyr Leu Val Tyr Met Gly Ser
        35                  40                  45

Asp Gly Asn Ser Asp Phe Glu Glu Asp Lys Glu Ser Thr Gly Thr Asp
    50                  55                  60

Glu Asp Ser Asn Thr Gly Ser Ser Ala Ala Ala Lys Val Thr Glu Ala
65                  70                  75                  80

Leu Ile Ile Glu Ala Glu Glu Asn Cys Thr Ala His Ile Thr Gly Trp
                85                  90                  95

Thr Thr Glu Thr Pro Thr Thr Leu Glu Pro Thr Thr Glu Ser Gln Phe
```

-continued 100 105 110

Glu Ala Ile Pro
115

<210> SEQ ID NO 276
<211> LENGTH: 117
<212> TYPE: PRT
<213> ORGANISM: Ixodes scapularis

<400> SEQUENCE: 276

Thr Leu Asn His Leu Pro Pro Val Val Asn Ala Thr Trp Glu Gly Ile
1 5 10 15

Arg His Arg Ile Asn Lys Thr Ile Pro Gln Phe Val Lys Leu Ile Cys
20 25 30

Asn Phe Thr Val Ala Met Pro Gln Glu Phe Tyr Leu Val Tyr Met Gly
35 40 45

Ser Asp Gly Asn Ser Asp Phe Glu Glu Asp Lys Glu Ser Thr Gly Thr
50 55 60

Asp Glu Asp Ser Asn Thr Gly Ser Ser Ala Ala Ala Lys Val Thr Glu
65 70 75 80

Ala Leu Ile Ile Glu Ala Glu Glu Asn Cys Thr Ala His Ile Thr Gly
85 90 95

Trp Thr Thr Glu Thr Pro Thr Thr Leu Glu Pro Thr Thr Glu Ser Gln
100 105 110

Phe Glu Ala Ile Pro
115

<210> SEQ ID NO 277
<211> LENGTH: 118
<212> TYPE: PRT
<213> ORGANISM: Ixodes scapularis

<400> SEQUENCE: 277

Cys Thr Leu Asn His Leu Pro Pro Val Val Asn Ala Thr Trp Glu Gly
1 5 10 15

Ile Arg His Arg Ile Asn Lys Thr Ile Pro Gln Phe Val Lys Leu Ile
20 25 30

Cys Asn Phe Thr Val Ala Met Pro Gln Glu Phe Tyr Leu Val Tyr Met
35 40 45

Gly Ser Asp Gly Asn Ser Asp Phe Glu Glu Asp Lys Glu Ser Thr Gly
50 55 60

Thr Asp Glu Asp Ser Asn Thr Gly Ser Ser Ala Ala Ala Lys Val Thr
65 70 75 80

Glu Ala Leu Ile Ile Glu Ala Glu Glu Asn Cys Thr Ala His Ile Thr
85 90 95

Gly Trp Thr Thr Glu Thr Pro Thr Thr Leu Glu Pro Thr Thr Glu Ser
100 105 110

Gln Phe Glu Ala Ile Pro
115

<210> SEQ ID NO 278
<211> LENGTH: 119
<212> TYPE: PRT
<213> ORGANISM: Ixodes scapularis

<400> SEQUENCE: 278

Asn Cys Thr Leu Asn His Leu Pro Pro Val Val Asn Ala Thr Trp Glu
1 5 10 15

-continued

```
Gly Ile Arg His Arg Ile Asn Lys Thr Ile Pro Gln Phe Val Lys Leu
            20                  25                  30

Ile Cys Asn Phe Thr Val Ala Met Pro Gln Glu Phe Tyr Leu Val Tyr
        35                  40                  45

Met Gly Ser Asp Gly Asn Ser Asp Phe Glu Glu Asp Lys Glu Ser Thr
    50                  55                  60

Gly Thr Asp Glu Asp Ser Asn Thr Gly Ser Ser Ala Ala Ala Lys Val
65                  70                  75                  80

Thr Glu Ala Leu Ile Ile Glu Ala Glu Glu Asn Cys Thr Ala His Ile
                85                  90                  95

Thr Gly Trp Thr Thr Glu Thr Pro Thr Thr Leu Glu Pro Thr Thr Glu
            100                 105                 110

Ser Gln Phe Glu Ala Ile Pro
        115


<210> SEQ ID NO 279
<211> LENGTH: 120
<212> TYPE: PRT
<213> ORGANISM: Ixodes scapularis

<400> SEQUENCE: 279

Tyr Asn Cys Thr Leu Asn His Leu Pro Pro Val Val Asn Ala Thr Trp
 1               5                  10                  15

Glu Gly Ile Arg His Arg Ile Asn Lys Thr Ile Pro Gln Phe Val Lys
            20                  25                  30

Leu Ile Cys Asn Phe Thr Val Ala Met Pro Gln Glu Phe Tyr Leu Val
        35                  40                  45

Tyr Met Gly Ser Asp Gly Asn Ser Asp Phe Glu Glu Asp Lys Glu Ser
    50                  55                  60

Thr Gly Thr Asp Glu Asp Ser Asn Thr Gly Ser Ser Ala Ala Ala Lys
65                  70                  75                  80

Val Thr Glu Ala Leu Ile Ile Glu Ala Glu Glu Asn Cys Thr Ala His
                85                  90                  95

Ile Thr Gly Trp Thr Thr Glu Thr Pro Thr Thr Leu Glu Pro Thr Thr
            100                 105                 110

Glu Ser Gln Phe Glu Ala Ile Pro
        115                 120


<210> SEQ ID NO 280
<211> LENGTH: 121
<212> TYPE: PRT
<213> ORGANISM: Ixodes scapularis

<400> SEQUENCE: 280

Val Tyr Asn Cys Thr Leu Asn His Leu Pro Pro Val Val Asn Ala Thr
 1               5                  10                  15

Trp Glu Gly Ile Arg His Arg Ile Asn Lys Thr Ile Pro Gln Phe Val
            20                  25                  30

Lys Leu Ile Cys Asn Phe Thr Val Ala Met Pro Gln Glu Phe Tyr Leu
        35                  40                  45

Val Tyr Met Gly Ser Asp Gly Asn Ser Asp Phe Glu Glu Asp Lys Glu
    50                  55                  60

Ser Thr Gly Thr Asp Glu Asp Ser Asn Thr Gly Ser Ser Ala Ala Ala
65                  70                  75                  80

Lys Val Thr Glu Ala Leu Ile Ile Glu Ala Glu Glu Asn Cys Thr Ala
                85                  90                  95
```

```
His Ile Thr Gly Trp Thr Thr Glu Thr Pro Thr Thr Leu Glu Pro Thr
            100                 105                 110

Thr Glu Ser Gln Phe Glu Ala Ile Pro
        115                 120


<210> SEQ ID NO 281
<211> LENGTH: 122
<212> TYPE: PRT
<213> ORGANISM: Ixodes scapularis

<400> SEQUENCE: 281

Ala Val Tyr Asn Cys Thr Leu Asn His Leu Pro Pro Val Val Asn Ala
 1               5                  10                  15

Thr Trp Glu Gly Ile Arg His Arg Ile Asn Lys Thr Ile Pro Gln Phe
            20                  25                  30

Val Lys Leu Ile Cys Asn Phe Thr Val Ala Met Pro Gln Glu Phe Tyr
        35                  40                  45

Leu Val Tyr Met Gly Ser Asp Gly Asn Ser Asp Phe Glu Glu Asp Lys
    50                  55                  60

Glu Ser Thr Gly Thr Asp Glu Asp Ser Asn Thr Gly Ser Ser Ala Ala
65                  70                  75                  80

Ala Lys Val Thr Glu Ala Leu Ile Ile Glu Ala Glu Glu Asn Cys Thr
                85                  90                  95

Ala His Ile Thr Gly Trp Thr Thr Glu Thr Pro Thr Thr Leu Glu Pro
            100                 105                 110

Thr Thr Glu Ser Gln Phe Glu Ala Ile Pro
        115                 120


<210> SEQ ID NO 282
<211> LENGTH: 123
<212> TYPE: PRT
<213> ORGANISM: Ixodes scapularis

<400> SEQUENCE: 282

Glu Ala Val Tyr Asn Cys Thr Leu Asn His Leu Pro Pro Val Val Asn
 1               5                  10                  15

Ala Thr Trp Glu Gly Ile Arg His Arg Ile Asn Lys Thr Ile Pro Gln
            20                  25                  30

Phe Val Lys Leu Ile Cys Asn Phe Thr Val Ala Met Pro Gln Glu Phe
        35                  40                  45

Tyr Leu Val Tyr Met Gly Ser Asp Gly Asn Ser Asp Phe Glu Glu Asp
    50                  55                  60

Lys Glu Ser Thr Gly Thr Asp Glu Asp Ser Asn Thr Gly Ser Ser Ala
65                  70                  75                  80

Ala Ala Lys Val Thr Glu Ala Leu Ile Ile Glu Ala Glu Glu Asn Cys
                85                  90                  95

Thr Ala His Ile Thr Gly Trp Thr Thr Glu Thr Pro Thr Thr Leu Glu
            100                 105                 110

Pro Thr Thr Glu Ser Gln Phe Glu Ala Ile Pro
        115                 120


<210> SEQ ID NO 283
<211> LENGTH: 124
<212> TYPE: PRT
<213> ORGANISM: Ixodes scapularis

<400> SEQUENCE: 283
```

-continued

```
Ala Glu Ala Val Tyr Asn Cys Thr Leu Asn His Leu Pro Pro Val Val
 1              5                  10                  15

Asn Ala Thr Trp Glu Gly Ile Arg His Arg Ile Asn Lys Thr Ile Pro
            20                  25                  30

Gln Phe Val Lys Leu Ile Cys Asn Phe Thr Val Ala Met Pro Gln Glu
        35                  40                  45

Phe Tyr Leu Val Tyr Met Gly Ser Asp Gly Asn Ser Asp Phe Glu Glu
    50                  55                  60

Asp Lys Glu Ser Thr Gly Thr Asp Glu Asp Ser Asn Thr Gly Ser Ser
65                  70                  75                  80

Ala Ala Ala Lys Val Thr Glu Ala Leu Ile Ile Glu Ala Glu Glu Asn
                85                  90                  95

Cys Thr Ala His Ile Thr Gly Trp Thr Thr Glu Thr Pro Thr Thr Leu
            100                 105                 110

Glu Pro Thr Thr Glu Ser Gln Phe Glu Ala Ile Pro
        115                 120


<210> SEQ ID NO 284
<211> LENGTH: 125
<212> TYPE: PRT
<213> ORGANISM: Ixodes scapularis

<400> SEQUENCE: 284

His Ala Glu Ala Val Tyr Asn Cys Thr Leu Asn His Leu Pro Pro Val
 1              5                  10                  15

Val Asn Ala Thr Trp Glu Gly Ile Arg His Arg Ile Asn Lys Thr Ile
            20                  25                  30

Pro Gln Phe Val Lys Leu Ile Cys Asn Phe Thr Val Ala Met Pro Gln
        35                  40                  45

Glu Phe Tyr Leu Val Tyr Met Gly Ser Asp Gly Asn Ser Asp Phe Glu
    50                  55                  60

Glu Asp Lys Glu Ser Thr Gly Thr Asp Glu Asp Ser Asn Thr Gly Ser
65                  70                  75                  80

Ser Ala Ala Ala Lys Val Thr Glu Ala Leu Ile Ile Glu Ala Glu Glu
                85                  90                  95

Asn Cys Thr Ala His Ile Thr Gly Trp Thr Thr Glu Thr Pro Thr Thr
            100                 105                 110

Leu Glu Pro Thr Thr Glu Ser Gln Phe Glu Ala Ile Pro
        115                 120                 125


<210> SEQ ID NO 285
<211> LENGTH: 126
<212> TYPE: PRT
<213> ORGANISM: Ixodes scapularis

<400> SEQUENCE: 285

Ser His Ala Glu Ala Val Tyr Asn Cys Thr Leu Asn His Leu Pro Pro
 1              5                  10                  15

Val Val Asn Ala Thr Trp Glu Gly Ile Arg His Arg Ile Asn Lys Thr
            20                  25                  30

Ile Pro Gln Phe Val Lys Leu Ile Cys Asn Phe Thr Val Ala Met Pro
        35                  40                  45

Gln Glu Phe Tyr Leu Val Tyr Met Gly Ser Asp Gly Asn Ser Asp Phe
    50                  55                  60

Glu Glu Asp Lys Glu Ser Thr Gly Thr Asp Glu Asp Ser Asn Thr Gly
65                  70                  75                  80
```

-continued

```
Ser Ser Ala Ala Ala Lys Val Thr Glu Ala Leu Ile Ile Glu Ala Glu
                85                  90                  95

Glu Asn Cys Thr Ala His Ile Thr Gly Trp Thr Thr Glu Thr Pro Thr
            100                 105                 110

Thr Leu Glu Pro Thr Thr Glu Ser Gln Phe Glu Ala Ile Pro
        115                 120                 125


<210> SEQ ID NO 286
<211> LENGTH: 127
<212> TYPE: PRT
<213> ORGANISM: Ixodes scapularis

<400> SEQUENCE: 286

Ser Ser His Ala Glu Ala Val Tyr Asn Cys Thr Leu Asn His Leu Pro
 1               5                  10                  15

Pro Val Val Asn Ala Thr Trp Glu Gly Ile Arg His Arg Ile Asn Lys
            20                  25                  30

Thr Ile Pro Gln Phe Val Lys Leu Ile Cys Asn Phe Thr Val Ala Met
        35                  40                  45

Pro Gln Glu Phe Tyr Leu Val Tyr Met Gly Ser Asp Gly Asn Ser Asp
    50                  55                  60

Phe Glu Glu Asp Lys Glu Ser Thr Gly Thr Asp Glu Asp Ser Asn Thr
65                  70                  75                  80

Gly Ser Ser Ala Ala Ala Lys Val Thr Glu Ala Leu Ile Ile Glu Ala
                85                  90                  95

Glu Glu Asn Cys Thr Ala His Ile Thr Gly Trp Thr Thr Glu Thr Pro
            100                 105                 110

Thr Thr Leu Glu Pro Thr Thr Glu Ser Gln Phe Glu Ala Ile Pro
        115                 120                 125


<210> SEQ ID NO 287
<211> LENGTH: 128
<212> TYPE: PRT
<213> ORGANISM: Ixodes scapularis

<400> SEQUENCE: 287

Asn Ser Ser His Ala Glu Ala Val Tyr Asn Cys Thr Leu Asn His Leu
 1               5                  10                  15

Pro Pro Val Val Asn Ala Thr Trp Glu Gly Ile Arg His Arg Ile Asn
            20                  25                  30

Lys Thr Ile Pro Gln Phe Val Lys Leu Ile Cys Asn Phe Thr Val Ala
        35                  40                  45

Met Pro Gln Glu Phe Tyr Leu Val Tyr Met Gly Ser Asp Gly Asn Ser
    50                  55                  60

Asp Phe Glu Glu Asp Lys Glu Ser Thr Gly Thr Asp Glu Asp Ser Asn
65                  70                  75                  80

Thr Gly Ser Ser Ala Ala Ala Lys Val Thr Glu Ala Leu Ile Ile Glu
                85                  90                  95

Ala Glu Glu Asn Cys Thr Ala His Ile Thr Gly Trp Thr Thr Glu Thr
            100                 105                 110

Pro Thr Thr Leu Glu Pro Thr Thr Glu Ser Gln Phe Glu Ala Ile Pro
        115                 120                 125


<210> SEQ ID NO 288
<211> LENGTH: 129
<212> TYPE: PRT
<213> ORGANISM: Ixodes scapularis
```

-continued

<400> SEQUENCE: 288

Arg Asn Ser Ser His Ala Glu Ala Val Tyr Asn Cys Thr Leu Asn His
1 5 10 15

Leu Pro Pro Val Val Asn Ala Thr Trp Glu Gly Ile Arg His Arg Ile
20 25 30

Asn Lys Thr Ile Pro Gln Phe Val Lys Leu Ile Cys Asn Phe Thr Val
35 40 45

Ala Met Pro Gln Glu Phe Tyr Leu Val Tyr Met Gly Ser Asp Gly Asn
50 55 60

Ser Asp Phe Glu Glu Asp Lys Glu Ser Thr Gly Thr Asp Glu Asp Ser
65 70 75 80

Asn Thr Gly Ser Ser Ala Ala Ala Lys Val Thr Glu Ala Leu Ile Ile
85 90 95

Glu Ala Glu Glu Asn Cys Thr Ala His Ile Thr Gly Trp Thr Thr Glu
100 105 110

Thr Pro Thr Thr Leu Glu Pro Thr Thr Glu Ser Gln Phe Glu Ala Ile
115 120 125

Pro

<210> SEQ ID NO 289
<211> LENGTH: 130
<212> TYPE: PRT
<213> ORGANISM: Ixodes scapularis

<400> SEQUENCE: 289

Tyr Arg Asn Ser Ser His Ala Glu Ala Val Tyr Asn Cys Thr Leu Asn
1 5 10 15

His Leu Pro Pro Val Val Asn Ala Thr Trp Glu Gly Ile Arg His Arg
20 25 30

Ile Asn Lys Thr Ile Pro Gln Phe Val Lys Leu Ile Cys Asn Phe Thr
35 40 45

Val Ala Met Pro Gln Glu Phe Tyr Leu Val Tyr Met Gly Ser Asp Gly
50 55 60

Asn Ser Asp Phe Glu Glu Asp Lys Glu Ser Thr Gly Thr Asp Glu Asp
65 70 75 80

Ser Asn Thr Gly Ser Ser Ala Ala Ala Lys Val Thr Glu Ala Leu Ile
85 90 95

Ile Glu Ala Glu Glu Asn Cys Thr Ala His Ile Thr Gly Trp Thr Thr
100 105 110

Glu Thr Pro Thr Thr Leu Glu Pro Thr Thr Glu Ser Gln Phe Glu Ala
115 120 125

Ile Pro
130

<210> SEQ ID NO 290
<211> LENGTH: 131
<212> TYPE: PRT
<213> ORGANISM: Ixodes scapularis

<400> SEQUENCE: 290

Gln Tyr Arg Asn Ser Ser His Ala Glu Ala Val Tyr Asn Cys Thr Leu
1 5 10 15

Asn His Leu Pro Pro Val Val Asn Ala Thr Trp Glu Gly Ile Arg His
20 25 30

Arg Ile Asn Lys Thr Ile Pro Gln Phe Val Lys Leu Ile Cys Asn Phe
35 40 45

-continued

```
Thr Val Ala Met Pro Gln Glu Phe Tyr Leu Val Tyr Met Gly Ser Asp
    50                  55                  60

Gly Asn Ser Asp Phe Glu Glu Asp Lys Glu Ser Thr Gly Thr Asp Glu
65                  70                  75                  80

Asp Ser Asn Thr Gly Ser Ser Ala Ala Ala Lys Val Thr Glu Ala Leu
                85                  90                  95

Ile Ile Glu Ala Glu Glu Asn Cys Thr Ala His Ile Thr Gly Trp Thr
            100                 105                 110

Thr Glu Thr Pro Thr Thr Leu Glu Pro Thr Thr Glu Ser Gln Phe Glu
        115                 120                 125

Ala Ile Pro
    130
```

<210> SEQ ID NO 291
<211> LENGTH: 132
<212> TYPE: PRT
<213> ORGANISM: Ixodes scapularis

<400> SEQUENCE: 291

```
Ala Gln Tyr Arg Asn Ser Ser His Ala Glu Ala Val Tyr Asn Cys Thr
 1               5                  10                  15

Leu Asn His Leu Pro Pro Val Val Asn Ala Thr Trp Glu Gly Ile Arg
            20                  25                  30

His Arg Ile Asn Lys Thr Ile Pro Gln Phe Val Lys Leu Ile Cys Asn
        35                  40                  45

Phe Thr Val Ala Met Pro Gln Glu Phe Tyr Leu Val Tyr Met Gly Ser
    50                  55                  60

Asp Gly Asn Ser Asp Phe Glu Glu Asp Lys Glu Ser Thr Gly Thr Asp
65                  70                  75                  80

Glu Asp Ser Asn Thr Gly Ser Ser Ala Ala Ala Lys Val Thr Glu Ala
                85                  90                  95

Leu Ile Ile Glu Ala Glu Glu Asn Cys Thr Ala His Ile Thr Gly Trp
            100                 105                 110

Thr Thr Glu Thr Pro Thr Thr Leu Glu Pro Thr Thr Glu Ser Gln Phe
        115                 120                 125

Glu Ala Ile Pro
    130
```

<210> SEQ ID NO 292
<211> LENGTH: 133
<212> TYPE: PRT
<213> ORGANISM: Ixodes scapularis

<400> SEQUENCE: 292

```
Gly Ala Gln Tyr Arg Asn Ser Ser His Ala Glu Ala Val Tyr Asn Cys
 1               5                  10                  15

Thr Leu Asn His Leu Pro Pro Val Val Asn Ala Thr Trp Glu Gly Ile
            20                  25                  30

Arg His Arg Ile Asn Lys Thr Ile Pro Gln Phe Val Lys Leu Ile Cys
        35                  40                  45

Asn Phe Thr Val Ala Met Pro Gln Glu Phe Tyr Leu Val Tyr Met Gly
    50                  55                  60

Ser Asp Gly Asn Ser Asp Phe Glu Glu Asp Lys Glu Ser Thr Gly Thr
65                  70                  75                  80

Asp Glu Asp Ser Asn Thr Gly Ser Ser Ala Ala Ala Lys Val Thr Glu
                85                  90                  95
```

-continued

```
Ala Leu Ile Ile Glu Ala Glu Glu Asn Cys Thr Ala His Ile Thr Gly
            100                 105                 110

Trp Thr Thr Glu Thr Pro Thr Thr Leu Glu Pro Thr Thr Glu Ser Gln
        115                 120                 125

Phe Glu Ala Ile Pro
    130
```

<210> SEQ ID NO 293
<211> LENGTH: 134
<212> TYPE: PRT
<213> ORGANISM: Ixodes scapularis

<400> SEQUENCE: 293

```
Cys Gly Ala Gln Tyr Arg Asn Ser Ser His Ala Glu Ala Val Tyr Asn
 1               5                  10                  15

Cys Thr Leu Asn His Leu Pro Pro Val Val Asn Ala Thr Trp Glu Gly
            20                  25                  30

Ile Arg His Arg Ile Asn Lys Thr Ile Pro Gln Phe Val Lys Leu Ile
        35                  40                  45

Cys Asn Phe Thr Val Ala Met Pro Gln Glu Phe Tyr Leu Val Tyr Met
    50                  55                  60

Gly Ser Asp Gly Asn Ser Asp Phe Glu Glu Asp Lys Glu Ser Thr Gly
65                  70                  75                  80

Thr Asp Glu Asp Ser Asn Thr Gly Ser Ser Ala Ala Ala Lys Val Thr
                85                  90                  95

Glu Ala Leu Ile Ile Glu Ala Glu Glu Asn Cys Thr Ala His Ile Thr
            100                 105                 110

Gly Trp Thr Thr Glu Thr Pro Thr Thr Leu Glu Pro Thr Thr Glu Ser
        115                 120                 125

Gln Phe Glu Ala Ile Pro
    130
```

<210> SEQ ID NO 294
<211> LENGTH: 135
<212> TYPE: PRT
<213> ORGANISM: Ixodes scapularis

<400> SEQUENCE: 294

```
Leu Cys Gly Ala Gln Tyr Arg Asn Ser Ser His Ala Glu Ala Val Tyr
 1               5                  10                  15

Asn Cys Thr Leu Asn His Leu Pro Pro Val Val Asn Ala Thr Trp Glu
            20                  25                  30

Gly Ile Arg His Arg Ile Asn Lys Thr Ile Pro Gln Phe Val Lys Leu
        35                  40                  45

Ile Cys Asn Phe Thr Val Ala Met Pro Gln Glu Phe Tyr Leu Val Tyr
    50                  55                  60

Met Gly Ser Asp Gly Asn Ser Asp Phe Glu Glu Asp Lys Glu Ser Thr
65                  70                  75                  80

Gly Thr Asp Glu Asp Ser Asn Thr Gly Ser Ser Ala Ala Ala Lys Val
                85                  90                  95

Thr Glu Ala Leu Ile Ile Glu Ala Glu Glu Asn Cys Thr Ala His Ile
            100                 105                 110

Thr Gly Trp Thr Thr Glu Thr Pro Thr Thr Leu Glu Pro Thr Thr Glu
        115                 120                 125

Ser Gln Phe Glu Ala Ile Pro
    130                 135
```

-continued

<210> SEQ ID NO 295
<211> LENGTH: 136
<212> TYPE: PRT
<213> ORGANISM: Ixodes scapularis

<400> SEQUENCE: 295

Gly Leu Cys Gly Ala Gln Tyr Arg Asn Ser Ser His Ala Glu Ala Val
1 5 10 15

Tyr Asn Cys Thr Leu Asn His Leu Pro Pro Val Val Asn Ala Thr Trp
20 25 30

Glu Gly Ile Arg His Arg Ile Asn Lys Thr Ile Pro Gln Phe Val Lys
35 40 45

Leu Ile Cys Asn Phe Thr Val Ala Met Pro Gln Glu Phe Tyr Leu Val
50 55 60

Tyr Met Gly Ser Asp Gly Asn Ser Asp Phe Glu Glu Asp Lys Glu Ser
65 70 75 80

Thr Gly Thr Asp Glu Asp Ser Asn Thr Gly Ser Ser Ala Ala Ala Lys
85 90 95

Val Thr Glu Ala Leu Ile Ile Glu Ala Glu Glu Asn Cys Thr Ala His
100 105 110

Ile Thr Gly Trp Thr Thr Glu Thr Pro Thr Thr Leu Glu Pro Thr Thr
115 120 125

Glu Ser Gln Phe Glu Ala Ile Pro
130 135

<210> SEQ ID NO 296
<211> LENGTH: 137
<212> TYPE: PRT
<213> ORGANISM: Ixodes scapularis

<400> SEQUENCE: 296

Ser Gly Leu Cys Gly Ala Gln Tyr Arg Asn Ser Ser His Ala Glu Ala
1 5 10 15

Val Tyr Asn Cys Thr Leu Asn His Leu Pro Pro Val Val Asn Ala Thr
20 25 30

Trp Glu Gly Ile Arg His Arg Ile Asn Lys Thr Ile Pro Gln Phe Val
35 40 45

Lys Leu Ile Cys Asn Phe Thr Val Ala Met Pro Gln Glu Phe Tyr Leu
50 55 60

Val Tyr Met Gly Ser Asp Gly Asn Ser Asp Phe Glu Glu Asp Lys Glu
65 70 75 80

Ser Thr Gly Thr Asp Glu Asp Ser Asn Thr Gly Ser Ser Ala Ala Ala
85 90 95

Lys Val Thr Glu Ala Leu Ile Ile Glu Ala Glu Glu Asn Cys Thr Ala
100 105 110

His Ile Thr Gly Trp Thr Thr Glu Thr Pro Thr Thr Leu Glu Pro Thr
115 120 125

Thr Glu Ser Gln Phe Glu Ala Ile Pro
130 135

<210> SEQ ID NO 297
<211> LENGTH: 138
<212> TYPE: PRT
<213> ORGANISM: Ixodes scapularis

<400> SEQUENCE: 297

-continued

```
His Ser Gly Leu Cys Gly Ala Gln Tyr Arg Asn Ser Ser His Ala Glu
 1              5                  10                  15

Ala Val Tyr Asn Cys Thr Leu Asn His Leu Pro Pro Val Val Asn Ala
            20                  25                  30

Thr Trp Glu Gly Ile Arg His Arg Ile Asn Lys Thr Ile Pro Gln Phe
        35                  40                  45

Val Lys Leu Ile Cys Asn Phe Thr Val Ala Met Pro Gln Glu Phe Tyr
    50                  55                  60

Leu Val Tyr Met Gly Ser Asp Gly Asn Ser Asp Phe Glu Glu Asp Lys
65                  70                  75                  80

Glu Ser Thr Gly Thr Asp Glu Asp Ser Asn Thr Gly Ser Ser Ala Ala
                85                  90                  95

Ala Lys Val Thr Glu Ala Leu Ile Ile Glu Ala Glu Glu Asn Cys Thr
            100                 105                 110

Ala His Ile Thr Gly Trp Thr Thr Glu Thr Pro Thr Thr Leu Glu Pro
        115                 120                 125

Thr Thr Glu Ser Gln Phe Glu Ala Ile Pro
    130                 135
```

<210> SEQ ID NO 298
<211> LENGTH: 139
<212> TYPE: PRT
<213> ORGANISM: Ixodes scapularis

<400> SEQUENCE: 298

```
Asn His Ser Gly Leu Cys Gly Ala Gln Tyr Arg Asn Ser Ser His Ala
 1              5                  10                  15

Glu Ala Val Tyr Asn Cys Thr Leu Asn His Leu Pro Pro Val Val Asn
            20                  25                  30

Ala Thr Trp Glu Gly Ile Arg His Arg Ile Asn Lys Thr Ile Pro Gln
        35                  40                  45

Phe Val Lys Leu Ile Cys Asn Phe Thr Val Ala Met Pro Gln Glu Phe
    50                  55                  60

Tyr Leu Val Tyr Met Gly Ser Asp Gly Asn Ser Asp Phe Glu Glu Asp
65                  70                  75                  80

Lys Glu Ser Thr Gly Thr Asp Glu Asp Ser Asn Thr Gly Ser Ser Ala
                85                  90                  95

Ala Ala Lys Val Thr Glu Ala Leu Ile Ile Glu Ala Glu Glu Asn Cys
            100                 105                 110

Thr Ala His Ile Thr Gly Trp Thr Thr Glu Thr Pro Thr Thr Leu Glu
        115                 120                 125

Pro Thr Thr Glu Ser Gln Phe Glu Ala Ile Pro
    130                 135
```

<210> SEQ ID NO 299
<211> LENGTH: 140
<212> TYPE: PRT
<213> ORGANISM: Ixodes scapularis

<400> SEQUENCE: 299

```
Arg Asn His Ser Gly Leu Cys Gly Ala Gln Tyr Arg Asn Ser Ser His
 1              5                  10                  15

Ala Glu Ala Val Tyr Asn Cys Thr Leu Asn His Leu Pro Pro Val Val
            20                  25                  30

Asn Ala Thr Trp Glu Gly Ile Arg His Arg Ile Asn Lys Thr Ile Pro
        35                  40                  45
```

-continued

```
Gln Phe Val Lys Leu Ile Cys Asn Phe Thr Val Ala Met Pro Gln Glu
    50                  55                  60

Phe Tyr Leu Val Tyr Met Gly Ser Asp Gly Asn Ser Asp Phe Glu Glu
65                  70                  75                  80

Asp Lys Glu Ser Thr Gly Thr Asp Glu Asp Ser Asn Thr Gly Ser Ser
                85                  90                  95

Ala Ala Ala Lys Val Thr Glu Ala Leu Ile Ile Glu Ala Glu Glu Asn
            100                 105                 110

Cys Thr Ala His Ile Thr Gly Trp Thr Thr Glu Thr Pro Thr Thr Leu
        115                 120                 125

Glu Pro Thr Thr Glu Ser Gln Phe Glu Ala Ile Pro
    130                 135                 140


<210> SEQ ID NO 300
<211> LENGTH: 141
<212> TYPE: PRT
<213> ORGANISM: Ixodes scapularis

<400> SEQUENCE: 300

Tyr Arg Asn His Ser Gly Leu Cys Gly Ala Gln Tyr Arg Asn Ser Ser
 1               5                  10                  15

His Ala Glu Ala Val Tyr Asn Cys Thr Leu Asn His Leu Pro Pro Val
            20                  25                  30

Val Asn Ala Thr Trp Glu Gly Ile Arg His Arg Ile Asn Lys Thr Ile
        35                  40                  45

Pro Gln Phe Val Lys Leu Ile Cys Asn Phe Thr Val Ala Met Pro Gln
    50                  55                  60

Glu Phe Tyr Leu Val Tyr Met Gly Ser Asp Gly Asn Ser Asp Phe Glu
65                  70                  75                  80

Glu Asp Lys Glu Ser Thr Gly Thr Asp Glu Asp Ser Asn Thr Gly Ser
                85                  90                  95

Ser Ala Ala Ala Lys Val Thr Glu Ala Leu Ile Ile Glu Ala Glu Glu
            100                 105                 110

Asn Cys Thr Ala His Ile Thr Gly Trp Thr Thr Glu Thr Pro Thr Thr
        115                 120                 125

Leu Glu Pro Thr Thr Glu Ser Gln Phe Glu Ala Ile Pro
    130                 135                 140


<210> SEQ ID NO 301
<211> LENGTH: 142
<212> TYPE: PRT
<213> ORGANISM: Ixodes scapularis

<400> SEQUENCE: 301

His Tyr Arg Asn His Ser Gly Leu Cys Gly Ala Gln Tyr Arg Asn Ser
 1               5                  10                  15

Ser His Ala Glu Ala Val Tyr Asn Cys Thr Leu Asn His Leu Pro Pro
            20                  25                  30

Val Val Asn Ala Thr Trp Glu Gly Ile Arg His Arg Ile Asn Lys Thr
        35                  40                  45

Ile Pro Gln Phe Val Lys Leu Ile Cys Asn Phe Thr Val Ala Met Pro
    50                  55                  60

Gln Glu Phe Tyr Leu Val Tyr Met Gly Ser Asp Gly Asn Ser Asp Phe
65                  70                  75                  80

Glu Glu Asp Lys Glu Ser Thr Gly Thr Asp Glu Asp Ser Asn Thr Gly
                85                  90                  95
```

-continued

```
Ser Ser Ala Ala Ala Lys Val Thr Glu Ala Leu Ile Ile Glu Ala Glu
            100                 105                 110

Glu Asn Cys Thr Ala His Ile Thr Gly Trp Thr Thr Glu Thr Pro Thr
        115                 120                 125

Thr Leu Glu Pro Thr Thr Glu Ser Gln Phe Glu Ala Ile Pro
    130                 135                 140


<210> SEQ ID NO 302
<211> LENGTH: 143
<212> TYPE: PRT
<213> ORGANISM: Ixodes scapularis

<400> SEQUENCE: 302

Arg His Tyr Arg Asn His Ser Gly Leu Cys Gly Ala Gln Tyr Arg Asn
 1               5                  10                  15

Ser Ser His Ala Glu Ala Val Tyr Asn Cys Thr Leu Asn His Leu Pro
            20                  25                  30

Pro Val Val Asn Ala Thr Trp Glu Gly Ile Arg His Arg Ile Asn Lys
        35                  40                  45

Thr Ile Pro Gln Phe Val Lys Leu Ile Cys Asn Phe Thr Val Ala Met
    50                  55                  60

Pro Gln Glu Phe Tyr Leu Val Tyr Met Gly Ser Asp Gly Asn Ser Asp
65                  70                  75                  80

Phe Glu Glu Asp Lys Glu Ser Thr Gly Thr Asp Glu Asp Ser Asn Thr
                85                  90                  95

Gly Ser Ser Ala Ala Ala Lys Val Thr Glu Ala Leu Ile Ile Glu Ala
            100                 105                 110

Glu Glu Asn Cys Thr Ala His Ile Thr Gly Trp Thr Thr Glu Thr Pro
        115                 120                 125

Thr Thr Leu Glu Pro Thr Thr Glu Ser Gln Phe Glu Ala Ile Pro
    130                 135                 140


<210> SEQ ID NO 303
<211> LENGTH: 144
<212> TYPE: PRT
<213> ORGANISM: Ixodes scapularis

<400> SEQUENCE: 303

Glu Arg His Tyr Arg Asn His Ser Gly Leu Cys Gly Ala Gln Tyr Arg
 1               5                  10                  15

Asn Ser Ser His Ala Glu Ala Val Tyr Asn Cys Thr Leu Asn His Leu
            20                  25                  30

Pro Pro Val Val Asn Ala Thr Trp Glu Gly Ile Arg His Arg Ile Asn
        35                  40                  45

Lys Thr Ile Pro Gln Phe Val Lys Leu Ile Cys Asn Phe Thr Val Ala
    50                  55                  60

Met Pro Gln Glu Phe Tyr Leu Val Tyr Met Gly Ser Asp Gly Asn Ser
65                  70                  75                  80

Asp Phe Glu Glu Asp Lys Glu Ser Thr Gly Thr Asp Glu Asp Ser Asn
                85                  90                  95

Thr Gly Ser Ser Ala Ala Ala Lys Val Thr Glu Ala Leu Ile Ile Glu
            100                 105                 110

Ala Glu Glu Asn Cys Thr Ala His Ile Thr Gly Trp Thr Thr Glu Thr
        115                 120                 125

Pro Thr Thr Leu Glu Pro Thr Thr Glu Ser Gln Phe Glu Ala Ile Pro
    130                 135                 140
```

```
<210> SEQ ID NO 304
<211> LENGTH: 145
<212> TYPE: PRT
<213> ORGANISM: Ixodes scapularis

<400> SEQUENCE: 304

Tyr Glu Arg His Tyr Arg Asn His Ser Gly Leu Cys Gly Ala Gln Tyr
 1               5                  10                  15

Arg Asn Ser Ser His Ala Glu Ala Val Tyr Asn Cys Thr Leu Asn His
            20                  25                  30

Leu Pro Pro Val Val Asn Ala Thr Trp Glu Gly Ile Arg His Arg Ile
        35                  40                  45

Asn Lys Thr Ile Pro Gln Phe Val Lys Leu Ile Cys Asn Phe Thr Val
    50                  55                  60

Ala Met Pro Gln Glu Phe Tyr Leu Val Tyr Met Gly Ser Asp Gly Asn
65                  70                  75                  80

Ser Asp Phe Glu Glu Asp Lys Glu Ser Thr Gly Thr Asp Glu Asp Ser
                85                  90                  95

Asn Thr Gly Ser Ser Ala Ala Ala Lys Val Thr Glu Ala Leu Ile Ile
            100                 105                 110

Glu Ala Glu Glu Asn Cys Thr Ala His Ile Thr Gly Trp Thr Thr Glu
        115                 120                 125

Thr Pro Thr Thr Leu Glu Pro Thr Thr Glu Ser Gln Phe Glu Ala Ile
    130                 135                 140

Pro
145


<210> SEQ ID NO 305
<211> LENGTH: 146
<212> TYPE: PRT
<213> ORGANISM: Ixodes scapularis

<400> SEQUENCE: 305

Leu Tyr Glu Arg His Tyr Arg Asn His Ser Gly Leu Cys Gly Ala Gln
 1               5                  10                  15

Tyr Arg Asn Ser Ser His Ala Glu Ala Val Tyr Asn Cys Thr Leu Asn
            20                  25                  30

His Leu Pro Pro Val Val Asn Ala Thr Trp Glu Gly Ile Arg His Arg
        35                  40                  45

Ile Asn Lys Thr Ile Pro Gln Phe Val Lys Leu Ile Cys Asn Phe Thr
    50                  55                  60

Val Ala Met Pro Gln Glu Phe Tyr Leu Val Tyr Met Gly Ser Asp Gly
65                  70                  75                  80

Asn Ser Asp Phe Glu Glu Asp Lys Glu Ser Thr Gly Thr Asp Glu Asp
                85                  90                  95

Ser Asn Thr Gly Ser Ser Ala Ala Ala Lys Val Thr Glu Ala Leu Ile
            100                 105                 110

Ile Glu Ala Glu Glu Asn Cys Thr Ala His Ile Thr Gly Trp Thr Thr
        115                 120                 125

Glu Thr Pro Thr Thr Leu Glu Pro Thr Thr Glu Ser Gln Phe Glu Ala
    130                 135                 140

Ile Pro
145


<210> SEQ ID NO 306
<211> LENGTH: 147
```

-continued

<212> TYPE: PRT
<213> ORGANISM: Ixodes scapularis

<400> SEQUENCE: 306

```
Asn Leu Tyr Glu Arg His Tyr Arg Asn His Ser Gly Leu Cys Gly Ala
 1              5                  10                  15

Gln Tyr Arg Asn Ser Ser His Ala Glu Ala Val Tyr Asn Cys Thr Leu
            20                  25                  30

Asn His Leu Pro Pro Val Val Asn Ala Thr Trp Glu Gly Ile Arg His
        35                  40                  45

Arg Ile Asn Lys Thr Ile Pro Gln Phe Val Lys Leu Ile Cys Asn Phe
    50                  55                  60

Thr Val Ala Met Pro Gln Glu Phe Tyr Leu Val Tyr Met Gly Ser Asp
65                  70                  75                  80

Gly Asn Ser Asp Phe Glu Glu Asp Lys Glu Ser Thr Gly Thr Asp Glu
                85                  90                  95

Asp Ser Asn Thr Gly Ser Ser Ala Ala Ala Lys Val Thr Glu Ala Leu
            100                 105                 110

Ile Ile Glu Ala Glu Glu Asn Cys Thr Ala His Ile Thr Gly Trp Thr
        115                 120                 125

Thr Glu Thr Pro Thr Thr Leu Glu Pro Thr Thr Glu Ser Gln Phe Glu
    130                 135                 140

Ala Ile Pro
145
```

<210> SEQ ID NO 307
<211> LENGTH: 148
<212> TYPE: PRT
<213> ORGANISM: Ixodes scapularis

<400> SEQUENCE: 307

```
Gln Asn Leu Tyr Glu Arg His Tyr Arg Asn His Ser Gly Leu Cys Gly
 1              5                  10                  15

Ala Gln Tyr Arg Asn Ser Ser His Ala Glu Ala Val Tyr Asn Cys Thr
            20                  25                  30

Leu Asn His Leu Pro Pro Val Val Asn Ala Thr Trp Glu Gly Ile Arg
        35                  40                  45

His Arg Ile Asn Lys Thr Ile Pro Gln Phe Val Lys Leu Ile Cys Asn
    50                  55                  60

Phe Thr Val Ala Met Pro Gln Glu Phe Tyr Leu Val Tyr Met Gly Ser
65                  70                  75                  80

Asp Gly Asn Ser Asp Phe Glu Glu Asp Lys Glu Ser Thr Gly Thr Asp
                85                  90                  95

Glu Asp Ser Asn Thr Gly Ser Ser Ala Ala Ala Lys Val Thr Glu Ala
            100                 105                 110

Leu Ile Ile Glu Ala Glu Glu Asn Cys Thr Ala His Ile Thr Gly Trp
        115                 120                 125

Thr Thr Glu Thr Pro Thr Thr Leu Glu Pro Thr Thr Glu Ser Gln Phe
    130                 135                 140

Glu Ala Ile Pro
145
```

<210> SEQ ID NO 308
<211> LENGTH: 149
<212> TYPE: PRT
<213> ORGANISM: Ixodes scapularis -continued

<400> SEQUENCE: 308

Thr Gln Asn Leu Tyr Glu Arg His Tyr Arg Asn His Ser Gly Leu Cys
1 5 10 15

Gly Ala Gln Tyr Arg Asn Ser Ser His Ala Glu Ala Val Tyr Asn Cys
20 25 30

Thr Leu Asn His Leu Pro Pro Val Val Asn Ala Thr Trp Glu Gly Ile
35 40 45

Arg His Arg Ile Asn Lys Thr Ile Pro Gln Phe Val Lys Leu Ile Cys
50 55 60

Asn Phe Thr Val Ala Met Pro Gln Glu Phe Tyr Leu Val Tyr Met Gly
65 70 75 80

Ser Asp Gly Asn Ser Asp Phe Glu Glu Asp Lys Glu Ser Thr Gly Thr
85 90 95

Asp Glu Asp Ser Asn Thr Gly Ser Ser Ala Ala Ala Lys Val Thr Glu
100 105 110

Ala Leu Ile Ile Glu Ala Glu Glu Asn Cys Thr Ala His Ile Thr Gly
115 120 125

Trp Thr Thr Glu Thr Pro Thr Thr Leu Glu Pro Thr Thr Glu Ser Gln
130 135 140

Phe Glu Ala Ile Pro
145

<210> SEQ ID NO 309
<211> LENGTH: 150
<212> TYPE: PRT
<213> ORGANISM: Ixodes scapularis

<400> SEQUENCE: 309

Thr Thr Gln Asn Leu Tyr Glu Arg His Tyr Arg Asn His Ser Gly Leu
1 5 10 15

Cys Gly Ala Gln Tyr Arg Asn Ser Ser His Ala Glu Ala Val Tyr Asn
20 25 30

Cys Thr Leu Asn His Leu Pro Pro Val Val Asn Ala Thr Trp Glu Gly
35 40 45

Ile Arg His Arg Ile Asn Lys Thr Ile Pro Gln Phe Val Lys Leu Ile
50 55 60

Cys Asn Phe Thr Val Ala Met Pro Gln Glu Phe Tyr Leu Val Tyr Met
65 70 75 80

Gly Ser Asp Gly Asn Ser Asp Phe Glu Glu Asp Lys Glu Ser Thr Gly
85 90 95

Thr Asp Glu Asp Ser Asn Thr Gly Ser Ser Ala Ala Ala Lys Val Thr
100 105 110

Glu Ala Leu Ile Ile Glu Ala Glu Glu Asn Cys Thr Ala His Ile Thr
115 120 125

Gly Trp Thr Thr Glu Thr Pro Thr Thr Leu Glu Pro Thr Thr Glu Ser
130 135 140

Gln Phe Glu Ala Ile Pro
145 150

<210> SEQ ID NO 310
<211> LENGTH: 151
<212> TYPE: PRT
<213> ORGANISM: Ixodes scapularis

<400> SEQUENCE: 310

Thr Thr Thr Gln Asn Leu Tyr Glu Arg His Tyr Arg Asn His Ser Gly

-continued

```
 1               5                   10                  15

Leu Cys Gly Ala Gln Tyr Arg Asn Ser Ser His Ala Glu Ala Val Tyr
            20                  25                  30

Asn Cys Thr Leu Asn His Leu Pro Pro Val Val Asn Ala Thr Trp Glu
        35                  40                  45

Gly Ile Arg His Arg Ile Asn Lys Thr Ile Pro Gln Phe Val Lys Leu
    50                  55                  60

Ile Cys Asn Phe Thr Val Ala Met Pro Gln Glu Phe Tyr Leu Val Tyr
65                  70                  75                  80

Met Gly Ser Asp Gly Asn Ser Asp Phe Glu Glu Asp Lys Glu Ser Thr
                85                  90                  95

Gly Thr Asp Glu Asp Ser Asn Thr Gly Ser Ser Ala Ala Ala Lys Val
            100                 105                 110

Thr Glu Ala Leu Ile Ile Glu Ala Glu Glu Asn Cys Thr Ala His Ile
        115                 120                 125

Thr Gly Trp Thr Thr Glu Thr Pro Thr Thr Leu Glu Pro Thr Thr Glu
    130                 135                 140

Ser Gln Phe Glu Ala Ile Pro
145                 150


<210> SEQ ID NO 311
<211> LENGTH: 152
<212> TYPE: PRT
<213> ORGANISM: Ixodes scapularis

<400> SEQUENCE: 311

Glu Thr Thr Thr Gln Asn Leu Tyr Glu Arg His Tyr Arg Asn His Ser
 1               5                   10                  15

Gly Leu Cys Gly Ala Gln Tyr Arg Asn Ser Ser His Ala Glu Ala Val
            20                  25                  30

Tyr Asn Cys Thr Leu Asn His Leu Pro Pro Val Val Asn Ala Thr Trp
        35                  40                  45

Glu Gly Ile Arg His Arg Ile Asn Lys Thr Ile Pro Gln Phe Val Lys
    50                  55                  60

Leu Ile Cys Asn Phe Thr Val Ala Met Pro Gln Glu Phe Tyr Leu Val
65                  70                  75                  80

Tyr Met Gly Ser Asp Gly Asn Ser Asp Phe Glu Glu Asp Lys Glu Ser
                85                  90                  95

Thr Gly Thr Asp Glu Asp Ser Asn Thr Gly Ser Ser Ala Ala Ala Lys
            100                 105                 110

Val Thr Glu Ala Leu Ile Ile Glu Ala Glu Glu Asn Cys Thr Ala His
        115                 120                 125

Ile Thr Gly Trp Thr Thr Glu Thr Pro Thr Thr Leu Glu Pro Thr Thr
    130                 135                 140

Glu Ser Gln Phe Glu Ala Ile Pro
145                 150


<210> SEQ ID NO 312
<211> LENGTH: 153
<212> TYPE: PRT
<213> ORGANISM: Ixodes scapularis

<400> SEQUENCE: 312

Val Glu Thr Thr Thr Gln Asn Leu Tyr Glu Arg His Tyr Arg Asn His
 1               5                   10                  15

Ser Gly Leu Cys Gly Ala Gln Tyr Arg Asn Ser Ser His Ala Glu Ala
```

-continued

```
            20                  25                  30

Val Tyr Asn Cys Thr Leu Asn His Leu Pro Pro Val Val Asn Ala Thr
        35                  40                  45

Trp Glu Gly Ile Arg His Arg Ile Asn Lys Thr Ile Pro Gln Phe Val
    50                  55                  60

Lys Leu Ile Cys Asn Phe Thr Val Ala Met Pro Gln Glu Phe Tyr Leu
65                  70                  75                  80

Val Tyr Met Gly Ser Asp Gly Asn Ser Asp Phe Glu Glu Asp Lys Glu
                85                  90                  95

Ser Thr Gly Thr Asp Glu Asp Ser Asn Thr Gly Ser Ser Ala Ala Ala
            100                 105                 110

Lys Val Thr Glu Ala Leu Ile Ile Glu Ala Glu Glu Asn Cys Thr Ala
        115                 120                 125

His Ile Thr Gly Trp Thr Thr Glu Thr Pro Thr Thr Leu Glu Pro Thr
    130                 135                 140

Thr Glu Ser Gln Phe Glu Ala Ile Pro
145                 150


<210> SEQ ID NO 313
<211> LENGTH: 154
<212> TYPE: PRT
<213> ORGANISM: Ixodes scapularis

<400> SEQUENCE: 313

Ile Val Glu Thr Thr Thr Gln Asn Leu Tyr Glu Arg His Tyr Arg Asn
 1               5                  10                  15

His Ser Gly Leu Cys Gly Ala Gln Tyr Arg Asn Ser Ser His Ala Glu
            20                  25                  30

Ala Val Tyr Asn Cys Thr Leu Asn His Leu Pro Pro Val Val Asn Ala
        35                  40                  45

Thr Trp Glu Gly Ile Arg His Arg Ile Asn Lys Thr Ile Pro Gln Phe
    50                  55                  60

Val Lys Leu Ile Cys Asn Phe Thr Val Ala Met Pro Gln Glu Phe Tyr
65                  70                  75                  80

Leu Val Tyr Met Gly Ser Asp Gly Asn Ser Asp Phe Glu Glu Asp Lys
                85                  90                  95

Glu Ser Thr Gly Thr Asp Glu Asp Ser Asn Thr Gly Ser Ser Ala Ala
            100                 105                 110

Ala Lys Val Thr Glu Ala Leu Ile Ile Glu Ala Glu Glu Asn Cys Thr
        115                 120                 125

Ala His Ile Thr Gly Trp Thr Thr Glu Thr Pro Thr Thr Leu Glu Pro
    130                 135                 140

Thr Thr Glu Ser Gln Phe Glu Ala Ile Pro
145                 150


<210> SEQ ID NO 314
<211> LENGTH: 155
<212> TYPE: PRT
<213> ORGANISM: Ixodes scapularis

<400> SEQUENCE: 314

Thr Ile Val Glu Thr Thr Thr Gln Asn Leu Tyr Glu Arg His Tyr Arg
 1               5                  10                  15

Asn His Ser Gly Leu Cys Gly Ala Gln Tyr Arg Asn Ser Ser His Ala
            20                  25                  30

Glu Ala Val Tyr Asn Cys Thr Leu Asn His Leu Pro Pro Val Val Asn
```

-continued

```
        35                  40                  45

Ala Thr Trp Glu Gly Ile Arg His Arg Ile Asn Lys Thr Ile Pro Gln
    50                  55                  60

Phe Val Lys Leu Ile Cys Asn Phe Thr Val Ala Met Pro Gln Glu Phe
65                  70                  75                  80

Tyr Leu Val Tyr Met Gly Ser Asp Gly Asn Ser Asp Phe Glu Glu Asp
                85                  90                  95

Lys Glu Ser Thr Gly Thr Asp Glu Asp Ser Asn Thr Gly Ser Ser Ala
            100                 105                 110

Ala Ala Lys Val Thr Glu Ala Leu Ile Ile Glu Ala Glu Glu Asn Cys
        115                 120                 125

Thr Ala His Ile Thr Gly Trp Thr Thr Glu Thr Pro Thr Thr Leu Glu
    130                 135                 140

Pro Thr Thr Glu Ser Gln Phe Glu Ala Ile Pro
145                 150                 155


<210> SEQ ID NO 315
<211> LENGTH: 156
<212> TYPE: PRT
<213> ORGANISM: Ixodes scapularis

<400> SEQUENCE: 315

Asp Thr Ile Val Glu Thr Thr Thr Gln Asn Leu Tyr Glu Arg His Tyr
 1               5                  10                  15

Arg Asn His Ser Gly Leu Cys Gly Ala Gln Tyr Arg Asn Ser Ser His
            20                  25                  30

Ala Glu Ala Val Tyr Asn Cys Thr Leu Asn His Leu Pro Pro Val Val
        35                  40                  45

Asn Ala Thr Trp Glu Gly Ile Arg His Arg Ile Asn Lys Thr Ile Pro
    50                  55                  60

Gln Phe Val Lys Leu Ile Cys Asn Phe Thr Val Ala Met Pro Gln Glu
65                  70                  75                  80

Phe Tyr Leu Val Tyr Met Gly Ser Asp Gly Asn Ser Asp Phe Glu Glu
                85                  90                  95

Asp Lys Glu Ser Thr Gly Thr Asp Glu Asp Ser Asn Thr Gly Ser Ser
            100                 105                 110

Ala Ala Ala Lys Val Thr Glu Ala Leu Ile Ile Glu Ala Glu Glu Asn
        115                 120                 125

Cys Thr Ala His Ile Thr Gly Trp Thr Thr Glu Thr Pro Thr Thr Leu
    130                 135                 140

Glu Pro Thr Thr Glu Ser Gln Phe Glu Ala Ile Pro
145                 150                 155


<210> SEQ ID NO 316
<211> LENGTH: 157
<212> TYPE: PRT
<213> ORGANISM: Ixodes scapularis

<400> SEQUENCE: 316

Gln Asp Thr Ile Val Glu Thr Thr Thr Gln Asn Leu Tyr Glu Arg His
 1               5                  10                  15

Tyr Arg Asn His Ser Gly Leu Cys Gly Ala Gln Tyr Arg Asn Ser Ser
            20                  25                  30

His Ala Glu Ala Val Tyr Asn Cys Thr Leu Asn His Leu Pro Pro Val
        35                  40                  45

Val Asn Ala Thr Trp Glu Gly Ile Arg His Arg Ile Asn Lys Thr Ile
```

-continued

```
    50                  55                  60

Pro Gln Phe Val Lys Leu Ile Cys Asn Phe Thr Val Ala Met Pro Gln
65                  70                  75                  80

Glu Phe Tyr Leu Val Tyr Met Gly Ser Asp Gly Asn Ser Asp Phe Glu
                85                  90                  95

Glu Asp Lys Glu Ser Thr Gly Thr Asp Glu Asp Ser Asn Thr Gly Ser
            100                 105                 110

Ser Ala Ala Ala Lys Val Thr Glu Ala Leu Ile Ile Glu Ala Glu Glu
        115                 120                 125

Asn Cys Thr Ala His Ile Thr Gly Trp Thr Thr Glu Thr Pro Thr Thr
    130                 135                 140

Leu Glu Pro Thr Thr Glu Ser Gln Phe Glu Ala Ile Pro
145                 150                 155


<210> SEQ ID NO 317
<211> LENGTH: 158
<212> TYPE: PRT
<213> ORGANISM: Ixodes scapularis

<400> SEQUENCE: 317

Glu Gln Asp Thr Ile Val Glu Thr Thr Thr Gln Asn Leu Tyr Glu Arg
 1               5                  10                  15

His Tyr Arg Asn His Ser Gly Leu Cys Gly Ala Gln Tyr Arg Asn Ser
            20                  25                  30

Ser His Ala Glu Ala Val Tyr Asn Cys Thr Leu Asn His Leu Pro Pro
        35                  40                  45

Val Val Asn Ala Thr Trp Glu Gly Ile Arg His Arg Ile Asn Lys Thr
    50                  55                  60

Ile Pro Gln Phe Val Lys Leu Ile Cys Asn Phe Thr Val Ala Met Pro
65                  70                  75                  80

Gln Glu Phe Tyr Leu Val Tyr Met Gly Ser Asp Gly Asn Ser Asp Phe
                85                  90                  95

Glu Glu Asp Lys Glu Ser Thr Gly Thr Asp Glu Asp Ser Asn Thr Gly
            100                 105                 110

Ser Ser Ala Ala Ala Lys Val Thr Glu Ala Leu Ile Ile Glu Ala Glu
        115                 120                 125

Glu Asn Cys Thr Ala His Ile Thr Gly Trp Thr Thr Glu Thr Pro Thr
    130                 135                 140

Thr Leu Glu Pro Thr Thr Glu Ser Gln Phe Glu Ala Ile Pro
145                 150                 155


<210> SEQ ID NO 318
<211> LENGTH: 159
<212> TYPE: PRT
<213> ORGANISM: Ixodes scapularis

<400> SEQUENCE: 318

Leu Glu Gln Asp Thr Ile Val Glu Thr Thr Thr Gln Asn Leu Tyr Glu
 1               5                  10                  15

Arg His Tyr Arg Asn His Ser Gly Leu Cys Gly Ala Gln Tyr Arg Asn
            20                  25                  30

Ser Ser His Ala Glu Ala Val Tyr Asn Cys Thr Leu Asn His Leu Pro
        35                  40                  45

Pro Val Val Asn Ala Thr Trp Glu Gly Ile Arg His Arg Ile Asn Lys
    50                  55                  60

Thr Ile Pro Gln Phe Val Lys Leu Ile Cys Asn Phe Thr Val Ala Met
```

-continued

```
65                  70                  75                  80

Pro Gln Glu Phe Tyr Leu Val Tyr Met Gly Ser Asp Gly Asn Ser Asp
                85                  90                  95

Phe Glu Glu Asp Lys Glu Ser Thr Gly Thr Asp Glu Asp Ser Asn Thr
            100                 105                 110

Gly Ser Ser Ala Ala Ala Lys Val Thr Glu Ala Leu Ile Ile Glu Ala
        115                 120                 125

Glu Glu Asn Cys Thr Ala His Ile Thr Gly Trp Thr Thr Glu Thr Pro
    130                 135                 140

Thr Thr Leu Glu Pro Thr Thr Glu Ser Gln Phe Glu Ala Ile Pro
145                 150                 155


<210> SEQ ID NO 319
<211> LENGTH: 160
<212> TYPE: PRT
<213> ORGANISM: Ixodes scapularis

<400> SEQUENCE: 319

Gly Leu Glu Gln Asp Thr Ile Val Glu Thr Thr Thr Gln Asn Leu Tyr
 1               5                  10                  15

Glu Arg His Tyr Arg Asn His Ser Gly Leu Cys Gly Ala Gln Tyr Arg
            20                  25                  30

Asn Ser Ser His Ala Glu Ala Val Tyr Asn Cys Thr Leu Asn His Leu
        35                  40                  45

Pro Pro Val Val Asn Ala Thr Trp Glu Gly Ile Arg His Arg Ile Asn
    50                  55                  60

Lys Thr Ile Pro Gln Phe Val Lys Leu Ile Cys Asn Phe Thr Val Ala
65                  70                  75                  80

Met Pro Gln Glu Phe Tyr Leu Val Tyr Met Gly Ser Asp Gly Asn Ser
                85                  90                  95

Asp Phe Glu Glu Asp Lys Glu Ser Thr Gly Thr Asp Glu Asp Ser Asn
            100                 105                 110

Thr Gly Ser Ser Ala Ala Ala Lys Val Thr Glu Ala Leu Ile Ile Glu
        115                 120                 125

Ala Glu Glu Asn Cys Thr Ala His Ile Thr Gly Trp Thr Thr Glu Thr
    130                 135                 140

Pro Thr Thr Leu Glu Pro Thr Thr Glu Ser Gln Phe Glu Ala Ile Pro
145                 150                 155                 160


<210> SEQ ID NO 320
<211> LENGTH: 161
<212> TYPE: PRT
<213> ORGANISM: Ixodes scapularis

<400> SEQUENCE: 320

Asp Gly Leu Glu Gln Asp Thr Ile Val Glu Thr Thr Thr Gln Asn Leu
 1               5                  10                  15

Tyr Glu Arg His Tyr Arg Asn His Ser Gly Leu Cys Gly Ala Gln Tyr
            20                  25                  30

Arg Asn Ser Ser His Ala Glu Ala Val Tyr Asn Cys Thr Leu Asn His
        35                  40                  45

Leu Pro Pro Val Val Asn Ala Thr Trp Glu Gly Ile Arg His Arg Ile
    50                  55                  60

Asn Lys Thr Ile Pro Gln Phe Val Lys Leu Ile Cys Asn Phe Thr Val
65                  70                  75                  80

Ala Met Pro Gln Glu Phe Tyr Leu Val Tyr Met Gly Ser Asp Gly Asn
```

-continued

```
                85                  90                  95

Ser Asp Phe Glu Glu Asp Lys Glu Ser Thr Gly Thr Asp Glu Asp Ser
            100                 105                 110

Asn Thr Gly Ser Ser Ala Ala Ala Lys Val Thr Glu Ala Leu Ile Ile
        115                 120                 125

Glu Ala Glu Glu Asn Cys Thr Ala His Ile Thr Gly Trp Thr Thr Glu
    130                 135                 140

Thr Pro Thr Thr Leu Glu Pro Thr Thr Glu Ser Gln Phe Glu Ala Ile
145                 150                 155                 160

Pro
```

<210> SEQ ID NO 321
<211> LENGTH: 162
<212> TYPE: PRT
<213> ORGANISM: Ixodes scapularis

<400> SEQUENCE: 321

```
Glu Asp Gly Leu Glu Gln Asp Thr Ile Val Glu Thr Thr Thr Gln Asn
 1               5                  10                  15

Leu Tyr Glu Arg His Tyr Arg Asn His Ser Gly Leu Cys Gly Ala Gln
            20                  25                  30

Tyr Arg Asn Ser Ser His Ala Glu Ala Val Tyr Asn Cys Thr Leu Asn
        35                  40                  45

His Leu Pro Pro Val Val Asn Ala Thr Trp Glu Gly Ile Arg His Arg
    50                  55                  60

Ile Asn Lys Thr Ile Pro Gln Phe Val Lys Leu Ile Cys Asn Phe Thr
65                  70                  75                  80

Val Ala Met Pro Gln Glu Phe Tyr Leu Val Tyr Met Gly Ser Asp Gly
                85                  90                  95

Asn Ser Asp Phe Glu Glu Asp Lys Glu Ser Thr Gly Thr Asp Glu Asp
            100                 105                 110

Ser Asn Thr Gly Ser Ser Ala Ala Ala Lys Val Thr Glu Ala Leu Ile
        115                 120                 125

Ile Glu Ala Glu Glu Asn Cys Thr Ala His Ile Thr Gly Trp Thr Thr
    130                 135                 140

Glu Thr Pro Thr Thr Leu Glu Pro Thr Thr Glu Ser Gln Phe Glu Ala
145                 150                 155                 160

Ile Pro
```

<210> SEQ ID NO 322

<400> SEQUENCE: 322

000

<210> SEQ ID NO 323

<400> SEQUENCE: 323

000

<210> SEQ ID NO 324

<400> SEQUENCE: 324

000

<210> SEQ ID NO 325

-continued

<400> SEQUENCE: 325

000

<210> SEQ ID NO 326

<400> SEQUENCE: 326

000

<210> SEQ ID NO 327

<400> SEQUENCE: 327

000

<210> SEQ ID NO 328

<400> SEQUENCE: 328

000

<210> SEQ ID NO 329

<400> SEQUENCE: 329

000

<210> SEQ ID NO 330

<400> SEQUENCE: 330

000

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

-continued

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

-continued

<210> SEQ ID NO 348

<400> SEQUENCE: 348

000

<210> SEQ ID NO 349

<400> SEQUENCE: 349

000

<210> SEQ ID NO 350

<400> SEQUENCE: 350

000

<210> SEQ ID NO 351

<400> SEQUENCE: 351

000

<210> SEQ ID NO 352

<400> SEQUENCE: 352

000

<210> SEQ ID NO 353

<400> SEQUENCE: 353

000

<210> SEQ ID NO 354

<400> SEQUENCE: 354

000

<210> SEQ ID NO 355

<400> SEQUENCE: 355

000

<210> SEQ ID NO 356

<400> SEQUENCE: 356

000

<210> SEQ ID NO 357

<400> SEQUENCE: 357

000

<210> SEQ ID NO 358

<400> SEQUENCE: 358

000

-continued

<210> SEQ ID NO 359

<400> SEQUENCE: 359

000

<210> SEQ ID NO 360

<400> SEQUENCE: 360

000

<210> SEQ ID NO 361

<400> SEQUENCE: 361

000

<210> SEQ ID NO 362

<400> SEQUENCE: 362

000

<210> SEQ ID NO 363

<400> SEQUENCE: 363

000

<210> SEQ ID NO 364

<400> SEQUENCE: 364

000

<210> SEQ ID NO 365

<400> SEQUENCE: 365

000

<210> SEQ ID NO 366

<400> SEQUENCE: 366

000

<210> SEQ ID NO 367

<400> SEQUENCE: 367

000

<210> SEQ ID NO 368

<400> SEQUENCE: 368

000

<210> SEQ ID NO 369

<400> SEQUENCE: 369

000

<210> SEQ ID NO 370

-continued

<400> SEQUENCE: 370

000

<210> SEQ ID NO 371

<400> SEQUENCE: 371

000

<210> SEQ ID NO 372

<400> SEQUENCE: 372

000

<210> SEQ ID NO 373

<400> SEQUENCE: 373

000

<210> SEQ ID NO 374

<400> SEQUENCE: 374

000

<210> SEQ ID NO 375

<400> SEQUENCE: 375

000

<210> SEQ ID NO 376

<400> SEQUENCE: 376

000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

-continued

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000

<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

-continued

<210> SEQ ID NO 393

<400> SEQUENCE: 393

000

<210> SEQ ID NO 394

<400> SEQUENCE: 394

000

<210> SEQ ID NO 395

<400> SEQUENCE: 395

000

<210> SEQ ID NO 396

<400> SEQUENCE: 396

000

<210> SEQ ID NO 397

<400> SEQUENCE: 397

000

<210> SEQ ID NO 398

<400> SEQUENCE: 398

000

<210> SEQ ID NO 399

<400> SEQUENCE: 399

000

<210> SEQ ID NO 400

<400> SEQUENCE: 400

000

<210> SEQ ID NO 401
<211> LENGTH: 754
<212> TYPE: DNA
<213> ORGANISM: Ixodes scapularis

<400> SEQUENCE: 401
acggttgctc acagcactga ggtttcagag caagggtcta ccagccatga ggactgcgtt 60
tacctgtgct cttttggcga tttcgtttct aggaagcccg tgttcgtcca gcgaagacgg 120
tctcgagcaa gataccatag tggaaactac tacacaaaat ctctacgaac gtcattatag 180
aaatcattct ggattgtgcg gggcacagta taggaattca agccatgcgg aagccgttta 240
caactgcacg ctcaatcatt tgcccccagt cgtgaatgca acctgggaag gaattaggca 300
tcgaattaat aaaaccatac ctcagtttgt aaaattgatt tgcaacttta ctgttgcgat 360
gcctcaagaa ttctacttag tttatatggg gtcagatgga aactcagact ttgaagagga 420
caaagagagc acaggcactg atgaagacag taacacggga tcttctgctg cagctaaagt 480

-continued

```
tacagaagcg ctaataatag aagcagagga aaactgcacg gcgcatataa ctggttggac    540

cactgaaacc ccgaccacgc tggaacctac gacagagtct caatttgagg caattccctg    600

aggcatcgtg tgccgatcta tcacccggtt atttcaccgc gtggttttga tgcccgtgca    660

agcacagttc tgatacgggt ggcgaggtgc tttgccgaga ttgatttaaa taaaattcga    720

taaagaaaaa aaaaaaaaaa aaaaaaaaaa aaaa                                754
```

<210> SEQ ID NO 402
<211> LENGTH: 184
<212> TYPE: PRT
<213> ORGANISM: Ixodes scapularis

<400> SEQUENCE: 402

```
Met Arg Thr Ala Phe Thr Cys Ala Leu Leu Ala Ile Ser Phe Leu Gly
 1               5                  10                  15

Ser Pro Cys Ser Ser Ser Glu Asp Gly Leu Glu Gln Asp Thr Ile Val
            20                  25                  30

Glu Thr Thr Thr Gln Asn Leu Tyr Glu Arg His Tyr Arg Asn His Ser
        35                  40                  45

Gly Leu Cys Gly Ala Gln Tyr Arg Asn Ser Ser His Ala Glu Ala Val
    50                  55                  60

Tyr Asn Cys Thr Leu Asn His Leu Pro Pro Val Val Asn Ala Thr Trp
65                  70                  75                  80

Glu Gly Ile Arg His Arg Ile Asn Lys Thr Ile Pro Gln Phe Val Lys
                85                  90                  95

Leu Ile Cys Asn Phe Thr Val Ala Met Pro Gln Glu Phe Tyr Leu Val
            100                 105                 110

Tyr Met Gly Ser Asp Gly Asn Ser Asp Phe Glu Glu Asp Lys Glu Ser
        115                 120                 125

Thr Gly Thr Asp Glu Asp Ser Asn Thr Gly Ser Ser Ala Ala Ala Lys
    130                 135                 140

Val Thr Glu Ala Leu Ile Ile Glu Ala Glu Glu Asn Cys Thr Ala His
145                 150                 155                 160

Ile Thr Gly Trp Thr Thr Glu Thr Pro Thr Thr Leu Glu Pro Thr Thr
                165                 170                 175

Glu Ser Gln Phe Glu Ala Ile Pro
            180
```

<210> SEQ ID NO 403
<211> LENGTH: 21
<212> TYPE: DNA
<213> ORGANISM: Ixodes scapularis

<400> SEQUENCE: 403

```
aagtactcta gcaattgtga g                                               21
```

<210> SEQ ID NO 404
<211> LENGTH: 21
<212> TYPE: DNA
<213> ORGANISM: Ixodes scapularis

<400> SEQUENCE: 404

```
ctcttcgcta ttacgccagc t                                               21
```